(12) United States Patent
Mikheev et al.

(10) Patent No.: US 11,149,291 B2
(45) Date of Patent: Oct. 19, 2021

(54) PRODUCTION OF CANNABINOIDS IN YEAST

(71) Applicant: BioMediCan, Inc., Fremont, CA (US)

(72) Inventors: Maxim Mikheev, Fremont, CA (US); Difeng Gao, Union City, CA (US)

(73) Assignee: BioMediCan, Inc., Fremont, CA (US)

( * ) Notice: Subject to any disclaimer, the term of this patent is extended or adjusted under 35 U.S.C. 154(b) by 0 days.

(21) Appl. No.: 16/630,051

(22) PCT Filed: Jul. 12, 2018

(86) PCT No.: PCT/US2018/041890
§ 371 (c)(1),
(2) Date: Jan. 10, 2020

(87) PCT Pub. No.: WO2019/014490
PCT Pub. Date: Jan. 17, 2019

(65) Prior Publication Data
US 2020/0165644 A1   May 28, 2020

Related U.S. Application Data

(60) Provisional application No. 62/531,827, filed on Jul. 12, 2017.

(51) Int. Cl.
| | | |
|---|---|---|
| *C12N 9/00* | (2006.01) | |
| *C12P 7/22* | (2006.01) | |
| *C12P 17/06* | (2006.01) | |
| *C12N 9/02* | (2006.01) | |
| *C12N 9/04* | (2006.01) | |
| *C12N 9/10* | (2006.01) | |
| *C12N 9/88* | (2006.01) | |

(52) U.S. Cl.
CPC ............ *C12P 17/06* (2013.01); *C12N 9/0004* (2013.01); *C12N 9/0006* (2013.01); *C12N 9/1029* (2013.01); *C12N 9/1085* (2013.01); *C12N 9/88* (2013.01); *C12N 9/93* (2013.01); *C12Y 101/01034* (2013.01); *C12Y 121/03007* (2015.07); *C12Y 121/03008* (2015.07); *C12Y 203/0102* (2013.01); *C12Y 203/01206* (2015.07); *C12Y 404/01026* (2015.07); *C12Y 604/01002* (2013.01)

(58) Field of Classification Search
CPC ............ C12N 9/004; C12Y 121/03007; C12Y 121/00308; C12Y 103/03; C12Y 402/01017
See application file for complete search history.

(56) References Cited

U.S. PATENT DOCUMENTS

| | | | |
|---|---|---|---|
| 10,563,211 B2 * | 2/2020 | Keasling | ............... C12N 15/70 |
| 2016/0010126 A1 | 1/2016 | Poulos et al. | |
| 2016/0298151 A1 | 10/2016 | Butt et al. | |

FOREIGN PATENT DOCUMENTS

WO    2014134281 A1    9/2014

OTHER PUBLICATIONS

Written Opinion and International Search Report dated Sep. 26, 2018 in PCT/US 18/41890.
Blazeck et al., "Harnessing Yarrowia Lipolytica Lipogenesis to Create a Platform for Lipid and Biofuel Production", Nature Communications, vol. 5, 3131, pp. 1-10 (2014).
Carvalho et al., "Designing Microorganisms for Heterologous Biosynthesis of Cannabinoids", FEMS, vol. 17, No. 4, pp. 1-11 (2017).
Cernak et al., "Engineering Kluyveromyces Marxianus as a Robust Synthetic Biology Platform Host", mBio, vol. 9, Issue 5, pp. 1-16 (2018).
International Preliminary Report of Patentability dated Jan. 23, 2020 and received in PCT /US2018/041890.
European Search Report dated Apr. 13, 2021, received in EP 18 83 2127.7.
Zirple et al., "Engineering Yeasts as Platform Organisms for Cannabinoid Biosynthesis", Journal of Biotechnology, vol. 259, pp. 204-212 (2017).
Zirple et al., "Production of Δ9-Tetrahydrocannabinolic Acid from Cannabigerolic Acid by Whole Cells of Pichia (Komagataella) Pastoris Expressing Δ9-Tetrahydrocannabinolic Acid Synthase from Cannabis Sativa L.", Biotechnology Letters, vol. 37, No. 9, pp. 1869-1875 (2015).

* cited by examiner

*Primary Examiner* — Maryam Monshipouri
(74) *Attorney, Agent, or Firm* — Haley Guiliano, LLP

(57) ABSTRACT

The present disclosure relates to the production of cannabinoids in yeast. In as aspect there is provided a genetically modified yeast comprising: one or more GPP producing genes and optionally, one or more GPP pathway genes; two or more olivetolic acid producing genes; one or more cannabinoid precursor or cannabinoid producing genes; one or more Hexanoyl-CoA producing genes, and at least 5% dry weight of fatty acids or fats.

18 Claims, 4 Drawing Sheets
Specification includes a Sequence Listing.

1. Geranyl-Pyrophosphate – GPP
2. Neryl-Pyrophosphate – NPP
3. Cannabinerolic Acid (Z)-CBGA-C5 A
4. Cannabicyclovarin - CBLV-C3
5. Cannabicylovarinic Acid A – CBLCVA-C3
6. Divarinolic Acid
7. Olivetolic Acid
8. Cannabicyclolic Acid A – CBLA-C5 A
9. Cannabicyclol – CBL-C5
10. Cannabivarichromene – CBCV-C3
11. Cannabichromevarinic Acid A – CBCVA-C3 A
12. Cannabigerovarinic Acid A – CBGVA-C3 A
13. Cannabigerolic Acid A – CBGA-C5 A
14. Cannabichromenic Acid A – CBCA-C5 A
15. Cannabichromene – CBC-C5
16. Cannabidivarin – CBDV-C3
17. Cannabidivarinic Acid – CBDVA-C3
18. Cannabigerovarin – CBGV-C3
19. Cannabigerol – CBG-C5
20. Cannabidiolic Acid – CBDA-C5
21. Cannabidiol – CBD-C5
22. Cannabielsoin – CBE-C3
23. Cannabielsoic Acid B - CBEA-C3 B
24. Δ9-Tetrahydro-Cannabivarinic Acid A – Δ9-THCVA-C3 A
25. Δ9-Tetrahydro-Cannabinolic Acid A – Δ9-THCA-C5 A
26. Cannabielsoic Acid A – CBEA-C5 A
27. Cannabielsoin – CBE-C5
28. Cannabivarin – CBV-C3
29. Δ9-Tetrahydrocannabivarin – Δ9-THCV-C3
30. Δ9-Tetrahydrocannabinol – Δ9-THC-C5
31. Cannabinolic Acid A CBNA-C5 A
32. Cannabinol CBN-C5
33. 11-Hydroxy- Δ9-Tetrahydrocannabinol – 11-OH-THC
34. 11-Nor-9-Carboxy- Δ9-Tetrahydrocannabinol – 11-COOH-THC

Figure 2 cont.

SEQUENCE LISTING

<160> NUMBER OF SEQ ID NOS: 24

<210> SEQ ID NO 1
<211> LENGTH: 352
<212> TYPE: PRT
<213> ORGANISM: Saccharomyces cerevisiae

<400> SEQUENCE: 1

```
Met Ala Ser Glu Lys Glu Ile Arg Arg Glu Arg Phe Leu Asn Val Phe
1               5                   10                  15

Pro Lys Leu Val Glu Glu Leu Asn Ala Ser Leu Leu Ala Tyr Gly Met
            20                  25                  30

Pro Lys Glu Ala Cys Asp Trp Tyr Ala His Ser Leu Asn Tyr Asn Thr
        35                  40                  45

Pro Gly Gly Lys Leu Asn Arg Gly Leu Ser Val Val Asp Thr Tyr Ala
    50                  55                  60

Ile Leu Ser Asn Lys Thr Val Glu Gln Leu Gly Gln Glu Glu Tyr Glu
65                  70                  75                  80

Lys Val Ala Ile Leu Gly Trp Cys Ile Glu Leu Leu Gln Ala Tyr Phe
                85                  90                  95

Leu Val Ala Asp Asp Met Met Asp Lys Ser Ile Thr Arg Arg Gly Gln
                100                 105                 110

Pro Cys Trp Tyr Lys Val Pro Glu Val Gly Glu Ile Ala Ile Asn Asp
            115                 120                 125

Ala Phe Met Leu Glu Ala Ala Ile Tyr Lys Leu Leu Lys Ser His Phe
        130                 135                 140

Arg Asn Glu Lys Tyr Tyr Ile Asp Ile Thr Glu Leu Phe His Glu Val
145                 150                 155                 160

Thr Phe Gln Thr Glu Leu Gly Gln Leu Met Asp Leu Ile Thr Ala Pro
                165                 170                 175

Glu Asp Lys Val Asp Leu Ser Lys Phe Ser Leu Lys Lys His Ser Phe
                180                 185                 190

Ile Val Thr Phe Glu Thr Ala Tyr Tyr Ser Phe Tyr Leu Pro Val Ala
            195                 200                 205

Leu Ala Met Tyr Val Ala Gly Ile Thr Asp Glu Lys Asp Leu Lys Gln
        210                 215                 220

Ala Arg Asp Val Leu Ile Pro Leu Gly Glu Tyr Phe Gln Ile Gln Asp
225                 230                 235                 240

Asp Tyr Leu Asp Cys Phe Gly Thr Pro Glu Gln Ile Gly Lys Ile Gly
                245                 250                 255

Thr Asp Ile Gln Asp Asn Lys Cys Ser Trp Val Ile Asn Lys Ala Leu
                260                 265                 270

Glu Leu Ala Ser Ala Glu Gln Arg Lys Thr Leu Asp Glu Asn Tyr Gly
            275                 280                 285

Lys Lys Asp Ser Val Ala Glu Ala Lys Cys Lys Lys Ile Phe Asn Asp
        290                 295                 300
```

```
Leu Lys Ile Glu Gln Leu Tyr His Glu Tyr Glu Ser Ile Ala Lys
305                 310                 315                 320

Asp Leu Lys Ala Lys Ile Ser Gln Val Asp Glu Ser Arg Gly Phe Lys
            325                 330                 335

Ala Asp Val Leu Thr Ala Phe Leu Asn Lys Val Tyr Lys Arg Ser Lys
        340                 345                 350
```

<210> SEQ ID NO 2
<211> LENGTH: 352
<212> TYPE: PRT
<213> ORGANISM: Saccharomyces cerevisiae

<400> SEQUENCE: 2

```
Met Ala Ser Glu Lys Glu Ile Arg Arg Glu Arg Phe Leu Asn Val Phe
1               5                   10                  15

Pro Lys Leu Val Glu Glu Leu Asn Ala Ser Leu Leu Ala Tyr Gly Met
            20                  25                  30

Pro Lys Glu Ala Cys Asp Trp Tyr Ala His Ser Leu Asn Tyr Asn Thr
        35                  40                  45

Pro Gly Gly Lys Leu Asn Arg Gly Leu Ser Val Asp Thr Tyr Ala
    50                  55                  60

Ile Leu Ser Asn Lys Thr Val Glu Gln Leu Gly Gln Glu Glu Tyr Glu
65              70                  75                  80

Lys Val Ala Ile Leu Gly Trp Cys Ile Glu Leu Leu Gln Ala Tyr Trp
                85                  90                  95

Leu Val Ala Asp Asp Met Met Asp Lys Ser Ile Thr Arg Arg Gly Gln
            100                 105                 110

Pro Cys Trp Tyr Lys Val Pro Glu Val Gly Glu Ile Ala Ile Trp Asp
        115                 120                 125

Ala Phe Met Leu Glu Ala Ala Ile Tyr Lys Leu Leu Lys Ser His Phe
130                 135                 140

Arg Asn Glu Lys Tyr Tyr Ile Asp Ile Thr Glu Leu Phe His Glu Val
145                 150                 155                 160

Thr Phe Gln Thr Glu Leu Gly Gln Leu Met Asp Leu Ile Thr Ala Pro
                165                 170                 175

Glu Asp Lys Val Asp Leu Ser Lys Phe Ser Leu Lys Lys His Ser Phe
            180                 185                 190

Ile Val Thr Phe Lys Thr Ala Tyr Tyr Ser Phe Tyr Leu Pro Val Ala
        195                 200                 205

Leu Ala Met Tyr Val Ala Gly Ile Thr Asp Glu Lys Asp Leu Lys Gln
    210                 215                 220

Ala Arg Asp Val Leu Ile Pro Leu Gly Glu Tyr Phe Gln Ile Gln Asp
225                 230                 235                 240

Asp Tyr Leu Asp Cys Phe Gly Thr Pro Glu Gln Ile Gly Lys Ile Gly
                245                 250                 255

Thr Asp Ile Gln Asp Asn Lys Cys Ser Trp Val Ile Asn Lys Ala Leu
            260                 265                 270

Glu Leu Ala Ser Ala Glu Gln Arg Lys Thr Leu Asp Glu Asn Tyr Gly
        275                 280                 285

Lys Lys Asp Ser Val Ala Glu Ala Lys Cys Lys Lys Ile Phe Asn Asp
    290                 295                 300

Leu Lys Ile Glu Gln Leu Tyr His Glu Tyr Glu Glu Ser Ile Ala Lys
305                 310                 315                 320

Asp Leu Lys Ala Lys Ile Ser Gln Val Asp Glu Ser Arg Gly Phe Lys
```

```
                        325                 330                 335
Ala Asp Val Leu Thr Ala Phe Leu Asn Lys Val Tyr Lys Arg Ser Lys
                340                 345                 350

<210> SEQ ID NO 3
<211> LENGTH: 344
<212> TYPE: PRT
<213> ORGANISM: Yarrowia lipolytica

<400> SEQUENCE: 3

Met Ser Lys Ala Lys Phe Glu Ser Val Phe Pro Arg Ile Ser Glu Glu
  1               5                  10                  15

Leu Val Gln Leu Leu Arg Asp Glu Gly Leu Pro Gln Asp Ala Val Gln
                 20                  25                  30

Trp Phe Ser Asp Ser Leu Gln Tyr Asn Cys Val Gly Gly Lys Leu Asn
             35                  40                  45

Arg Gly Leu Ser Val Val Asp Thr Tyr Gln Leu Leu Thr Gly Lys Lys
         50                  55                  60

Glu Leu Asp Asp Glu Glu Tyr Tyr Arg Leu Ala Leu Gly Trp Leu
 65                  70                  75                  80

Ile Glu Leu Leu Gln Ala Phe Phe Leu Val Ser Asp Asp Ile Met Asp
                 85                  90                  95

Glu Ser Lys Thr Arg Arg Gly Gln Pro Cys Trp Tyr Leu Lys Pro Lys
                100                 105                 110

Val Gly Met Ile Ala Ile Asn Asp Ala Phe Met Leu Glu Ser Gly Ile
            115                 120                 125

Tyr Ile Leu Leu Lys Lys His Phe Arg Gln Glu Lys Tyr Tyr Ile Asp
        130                 135                 140

Leu Val Glu Leu Phe His Asp Ile Ser Phe Lys Thr Glu Leu Gly Gln
145                 150                 155                 160

Leu Val Asp Leu Leu Thr Ala Pro Glu Asp Glu Val Asp Leu Asn Arg
                165                 170                 175

Phe Ser Leu Asp Lys His Ser Phe Ile Val Arg Tyr Glu Thr Ala Tyr
            180                 185                 190

Tyr Ser Phe Tyr Leu Pro Val Val Leu Ala Met Tyr Val Ala Gly Ile
        195                 200                 205

Thr Asn Pro Lys Asp Leu Gln Gln Ala Met Asp Val Leu Ile Pro Leu
    210                 215                 220

Gly Glu Tyr Phe Gln Val Gln Asp Asp Tyr Leu Asp Asn Phe Gly Asp
225                 230                 235                 240

Pro Glu Phe Ile Gly Lys Ile Gly Thr Asp Ile Gln Asp Asn Lys Cys
                245                 250                 255

Ser Trp Leu Val Asn Lys Ala Leu Gln Lys Ala Thr Pro Glu Gln Arg
            260                 265                 270

Gln Ile Leu Glu Asp Asn Tyr Gly Val Lys Asp Lys Ser Lys Glu Leu
        275                 280                 285

Val Ile Lys Lys Leu Tyr Asp Asp Met Lys Ile Glu Gln Asp Tyr Leu
    290                 295                 300

Asp Tyr Glu Glu Glu Val Val Gly Asp Ile Lys Lys Ile Glu Gln
305                 310                 315                 320

Val Asp Glu Ser Arg Gly Phe Lys Lys Glu Val Leu Asn Ala Phe Leu
                325                 330                 335

Ala Lys Ile Tyr Lys Arg Gln Lys
            340
```

<210> SEQ ID NO 4
<211> LENGTH: 344
<212> TYPE: PRT
<213> ORGANISM: Yarrowia lipolytica

<400> SEQUENCE: 4

Ala Ser Lys Ala Lys Phe Glu Ser Val Phe Pro Arg Ile Ser Glu Glu
1               5                   10                  15

Leu Val Gln Leu Leu Arg Asp Glu Gly Leu Pro Gln Asp Ala Val Gln
            20                  25                  30

Trp Phe Ser Asp Ser Leu Gln Tyr Asn Cys Val Gly Gly Lys Leu Asn
        35                  40                  45

Arg Gly Leu Ser Val Val Asp Thr Tyr Gln Leu Leu Thr Gly Lys Lys
    50                  55                  60

Glu Leu Asp Asp Glu Gly Tyr Tyr Arg Leu Ala Leu Leu Gly Trp Leu
65                  70                  75                  80

Ile Glu Leu Leu Gln Ala Phe Trp Leu Val Ser Asp Asp Ile Met Asp
                85                  90                  95

Glu Ser Lys Thr Arg Arg Gly Gln Pro Cys Trp Tyr Leu Lys Pro Lys
            100                 105                 110

Val Gly Met Ile Ala Ile Trp Asp Ala Phe Met Leu Glu Ser Gly Ile
        115                 120                 125

Tyr Ile Leu Leu Lys Lys His Phe Arg Gln Lys Tyr Tyr Ile Asp
130                 135                 140

Leu Val Glu Leu Phe His Asp Ile Ser Phe Lys Thr Glu Leu Gly Gln
145                 150                 155                 160

Leu Val Asp Leu Leu Thr Ala Pro Glu Asp Glu Val Asp Leu Asn Arg
                165                 170                 175

Phe Ser Leu Asp Lys His Ser Phe Ile Val Arg Tyr Lys Thr Ala Tyr
            180                 185                 190

Tyr Ser Phe Tyr Leu Pro Val Val Leu Ala Met Tyr Val Ala Gly Ile
        195                 200                 205

Thr Asn Pro Lys Asp Leu Gln Gln Ala Met Asp Val Leu Ile Pro Leu
    210                 215                 220

Gly Glu Tyr Phe Gln Val Gln Asp Asp Tyr Leu Asp Asn Phe Gly Asp
225                 230                 235                 240

Pro Glu Phe Ile Gly Lys Ile Gly Thr Asp Ile Gln Asp Asn Lys Cys
                245                 250                 255

Ser Trp Leu Val Asn Lys Ala Leu Gln Lys Ala Thr Pro Glu Gln Arg
            260                 265                 270

Gln Ile Leu Glu Asp Asn Tyr Gly Val Lys Asp Lys Ser Lys Glu Leu
        275                 280                 285

Val Ile Lys Lys Leu Tyr Asp Asp Met Lys Ile Glu Gln Asp Tyr Leu
    290                 295                 300

Asp Tyr Glu Glu Glu Val Val Gly Asp Ile Lys Lys Ile Glu Gln
305                 310                 315                 320

Val Asp Glu Ser Arg Gly Phe Lys Lys Glu Val Leu Asn Ala Phe Leu
                325                 330                 335

Ala Lys Ile Tyr Lys Arg Gln Lys
            340

<210> SEQ ID NO 5
<211> LENGTH: 999
<212> TYPE: PRT
<213> ORGANISM: Yarrowia lipolytica

```
<400> SEQUENCE: 5

Met Leu Gln Ala Ala Ile Gly Lys Ile Val Gly Phe Ala Val Asn Arg
1               5                   10                  15

Pro Ile His Thr Val Val Leu Thr Ser Ile Val Ala Ser Thr Ala Tyr
            20                  25                  30

Leu Ala Ile Leu Asp Ile Ala Ile Pro Gly Phe Glu Gly Thr Gln Pro
        35                  40                  45

Ile Ser Tyr Tyr His Pro Ala Lys Ser Tyr Asp Asn Pro Ala Asp
    50                  55                  60

Trp Thr His Ile Ala Glu Ala Asp Ile Pro Ser Asp Ala Tyr Arg Leu
65                  70                  75                  80

Ala Phe Ala Gln Ile Arg Val Ser Asp Val Gln Gly Gly Glu Ala Pro
                85                  90                  95

Thr Ile Pro Gly Ala Val Ala Val Ser Asp Leu Asp His Arg Ile Val
            100                 105                 110

Met Asp Tyr Lys Gln Trp Ala Pro Trp Thr Ala Ser Asn Glu Gln Ile
        115                 120                 125

Ala Ser Glu Asn His Ile Trp Lys His Ser Phe Lys Asp His Val Ala
130                 135                 140

Phe Ser Trp Ile Lys Trp Phe Arg Trp Ala Tyr Leu Arg Leu Ser Thr
145                 150                 155                 160

Leu Ile Gln Gly Ala Asp Asn Phe Asp Ile Ala Val Val Ala Leu Gly
                165                 170                 175

Tyr Leu Ala Met His Tyr Thr Phe Phe Ser Leu Phe Arg Ser Met Arg
            180                 185                 190

Lys Val Gly Ser His Phe Trp Leu Ala Ser Met Ala Leu Val Ser Ser
        195                 200                 205

Thr Phe Ala Phe Leu Leu Ala Val Ala Ser Ser Ser Leu Gly Tyr
210                 215                 220

Arg Pro Ser Met Ile Thr Met Ser Glu Gly Leu Pro Phe Leu Val Val
225                 230                 235                 240

Ala Ile Gly Phe Asp Arg Lys Val Asn Leu Ala Ser Glu Val Leu Thr
                245                 250                 255

Ser Lys Ser Ser Gln Leu Ala Pro Met Val Gln Val Ile Thr Lys Ile
            260                 265                 270

Ala Ser Lys Ala Leu Phe Glu Tyr Ser Leu Glu Val Ala Ala Leu Phe
        275                 280                 285

Ala Gly Ala Tyr Thr Gly Val Pro Arg Leu Ser Gln Phe Cys Phe Leu
        290                 295                 300

Ser Ala Trp Ile Leu Ile Phe Asp Tyr Met Phe Leu Leu Thr Phe Tyr
305                 310                 315                 320

Ser Ala Val Leu Ala Ile Lys Phe Glu Ile Asn His Ile Lys Arg Asn
                325                 330                 335

Arg Met Ile Gln Asp Ala Leu Lys Glu Asp Gly Val Ser Ala Ala Val
            340                 345                 350

Ala Glu Lys Val Ala Asp Ser Ser Pro Asp Ala Lys Leu Asp Arg Lys
        355                 360                 365

Ser Asp Val Ser Leu Phe Gly Ala Ser Gly Ala Ile Ala Val Phe Lys
        370                 375                 380

Ile Phe Met Val Leu Gly Phe Leu Gly Leu Asn Leu Ile Asn Leu Thr
385                 390                 395                 400

Ala Ile Pro His Leu Gly Lys Ala Ala Ala Ala Ala Gln Ser Val Thr
```

-continued

```
               405                 410                 415
Pro Ile Thr Leu Ser Pro Glu Leu Leu His Ala Ile Pro Ala Ser Val
                420                 425                 430
Pro Val Val Thr Phe Val Pro Ser Val Val Tyr Glu His Ser Gln
            435                 440                 445
Leu Ile Leu Gln Leu Glu Asp Ala Leu Thr Thr Phe Leu Ala Ala Cys
            450                 455                 460
Ser Lys Thr Ile Gly Asp Pro Val Ile Ser Lys Tyr Ile Phe Leu Cys
465                 470                 475                 480
Leu Met Val Ser Thr Ala Leu Asn Val Tyr Leu Phe Gly Ala Thr Arg
                485                 490                 495
Glu Val Val Arg Thr Gln Ser Val Lys Val Glu Lys His Val Pro
            500                 505                 510
Ile Val Ile Glu Lys Pro Ser Glu Lys Glu Asp Thr Ser Ser Glu
            515                 520                 525
Asp Ser Ile Glu Leu Thr Val Gly Lys Gln Pro Lys Pro Val Thr Glu
            530                 535                 540
Thr Arg Ser Leu Asp Asp Leu Glu Ala Ile Met Lys Ala Gly Lys Thr
545                 550                 555                 560
Lys Leu Leu Glu Asp His Glu Val Val Lys Leu Ser Leu Glu Gly Lys
                565                 570                 575
Leu Pro Leu Tyr Ala Leu Glu Lys Gln Leu Gly Asp Asn Thr Arg Ala
                580                 585                 590
Val Gly Ile Arg Arg Ser Ile Ile Ser Gln Gln Ser Asn Thr Lys Thr
            595                 600                 605
Leu Glu Thr Ser Lys Leu Pro Tyr Leu His Tyr Asp Tyr Asp Arg Val
            610                 615                 620
Phe Gly Ala Cys Cys Glu Asn Val Ile Gly Tyr Met Pro Leu Pro Val
625                 630                 635                 640
Gly Val Ala Gly Pro Met Asn Ile Asp Gly Lys Asn Tyr His Ile Pro
                645                 650                 655
Met Ala Thr Thr Glu Gly Cys Leu Val Ala Ser Thr Met Arg Gly Cys
                660                 665                 670
Lys Ala Ile Asn Ala Gly Gly Gly Val Thr Thr Val Leu Thr Gln Asp
            675                 680                 685
Gly Met Thr Arg Gly Pro Cys Val Ser Phe Pro Ser Leu Lys Arg Ala
            690                 695                 700
Gly Ala Ala Lys Ile Trp Leu Asp Ser Glu Glu Gly Leu Lys Ser Met
705                 710                 715                 720
Arg Lys Ala Phe Asn Ser Thr Ser Arg Phe Ala Arg Leu Gln Ser Leu
                725                 730                 735
His Ser Thr Leu Ala Gly Asn Leu Leu Phe Ile Arg Phe Arg Thr Thr
            740                 745                 750
Thr Gly Asp Ala Met Gly Met Asn Met Ile Ser Lys Gly Val Glu His
            755                 760                 765
Ser Leu Ala Val Met Val Lys Glu Tyr Gly Phe Pro Asp Met Asp Ile
            770                 775                 780
Val Ser Val Ser Gly Asn Tyr Cys Thr Asp Lys Lys Pro Ala Ala Ile
785                 790                 795                 800
Asn Trp Ile Glu Gly Arg Gly Lys Ser Val Val Ala Glu Ala Thr Ile
                805                 810                 815
Pro Ala His Ile Val Lys Ser Val Leu Lys Ser Glu Val Asp Ala Leu
            820                 825                 830
```

```
Val Glu Leu Asn Ile Ser Lys Asn Leu Ile Gly Ser Ala Met Ala Gly
        835                 840                 845

Ser Val Gly Gly Phe Asn Ala His Ala Ala Asn Leu Val Thr Ala Ile
    850                 855                 860

Tyr Leu Ala Thr Gly Gln Asp Pro Ala Gln Asn Val Glu Ser Ser Asn
865                 870                 875                 880

Cys Ile Thr Leu Met Ser Asn Val Asp Gly Asn Leu Leu Ile Ser Val
                885                 890                 895

Ser Met Pro Ser Ile Glu Val Gly Thr Ile Gly Gly Gly Thr Ile Leu
            900                 905                 910

Glu Pro Gln Gly Ala Met Leu Glu Met Leu Gly Val Arg Gly Pro His
        915                 920                 925

Ile Glu Thr Pro Gly Ala Asn Ala Gln Gln Leu Ala Arg Ile Ile Ala
    930                 935                 940

Ser Gly Val Leu Ala Ala Glu Leu Ser Leu Cys Ser Ala Leu Ala Ala
945                 950                 955                 960

Gly His Leu Val Gln Ser His Met Thr His Asn Arg Ser Gln Ala Pro
                965                 970                 975

Thr Pro Ala Lys Gln Ser Gln Ala Asp Leu Gln Arg Leu Gln Asn Gly
            980                 985                 990

Ser Asn Ile Cys Ile Arg Ser
        995

<210> SEQ ID NO 6
<211> LENGTH: 499
<212> TYPE: PRT
<213> ORGANISM: Yarrowia lipolytica

<400> SEQUENCE: 6

Thr Gln Ser Val Lys Val Val Glu Lys His Val Pro Ile Val Ile Glu
1               5                   10                  15

Lys Pro Ser Glu Lys Glu Glu Asp Thr Ser Ser Glu Asp Ser Ile Glu
            20                  25                  30

Leu Thr Val Gly Lys Gln Pro Lys Pro Val Thr Glu Thr Arg Ser Leu
        35                  40                  45

Asp Asp Leu Glu Ala Ile Met Lys Ala Gly Lys Thr Lys Leu Leu Glu
    50                  55                  60

Asp His Glu Val Val Lys Leu Ser Leu Glu Gly Lys Leu Pro Leu Tyr
65                  70                  75                  80

Ala Leu Glu Lys Gln Leu Gly Asp Asn Thr Arg Ala Val Gly Ile Arg
                85                  90                  95

Arg Ser Ile Ile Ser Gln Gln Ser Asn Thr Lys Thr Leu Glu Thr Ser
            100                 105                 110

Lys Leu Pro Tyr Leu His Tyr Asp Tyr Asp Arg Val Phe Gly Ala Cys
        115                 120                 125

Cys Glu Asn Val Ile Gly Tyr Met Pro Leu Pro Val Gly Val Ala Gly
    130                 135                 140

Pro Met Asn Ile Asp Gly Lys Asn Tyr His Ile Pro Met Ala Thr Thr
145                 150                 155                 160

Glu Gly Cys Leu Val Ala Ser Thr Met Arg Gly Cys Lys Ala Ile Asn
                165                 170                 175

Ala Gly Gly Gly Val Thr Thr Val Leu Thr Gln Asp Gly Met Thr Arg
            180                 185                 190

Gly Pro Cys Val Ser Phe Pro Ser Leu Lys Arg Ala Gly Ala Ala Lys
```

```
            195                 200                 205
Ile Trp Leu Asp Ser Glu Glu Gly Leu Lys Ser Met Arg Lys Ala Phe
210                 215                 220

Asn Ser Thr Ser Arg Phe Ala Arg Leu Gln Ser Leu His Ser Thr Leu
225                 230                 235                 240

Ala Gly Asn Leu Leu Phe Ile Arg Phe Arg Thr Thr Thr Gly Asp Ala
                245                 250                 255

Met Gly Met Asn Met Ile Ser Lys Gly Val Glu His Ser Leu Ala Val
                260                 265                 270

Met Val Lys Glu Tyr Gly Phe Pro Asp Met Asp Ile Val Ser Val Ser
                275                 280                 285

Gly Asn Tyr Cys Thr Asp Lys Lys Pro Ala Ala Ile Asn Trp Ile Glu
290                 295                 300

Gly Arg Gly Lys Ser Val Val Ala Glu Ala Thr Ile Pro Ala His Ile
305                 310                 315                 320

Val Lys Ser Val Leu Lys Ser Glu Val Asp Ala Leu Val Glu Leu Asn
                325                 330                 335

Ile Ser Lys Asn Leu Ile Gly Ser Ala Met Ala Gly Ser Val Gly Gly
                340                 345                 350

Phe Asn Ala His Ala Ala Asn Leu Val Thr Ala Ile Tyr Leu Ala Thr
                355                 360                 365

Gly Gln Asp Pro Ala Gln Asn Val Glu Ser Ser Asn Cys Ile Thr Leu
                370                 375                 380

Met Ser Asn Val Asp Gly Asn Leu Leu Ile Ser Val Ser Met Pro Ser
385                 390                 395                 400

Ile Glu Val Gly Thr Ile Gly Gly Thr Ile Leu Glu Pro Gln Gly
                    405                 410                 415

Ala Met Leu Glu Met Leu Gly Val Arg Gly Pro His Ile Glu Thr Pro
                420                 425                 430

Gly Ala Asn Ala Gln Gln Leu Ala Arg Ile Ile Ala Ser Gly Val Leu
                435                 440                 445

Ala Ala Glu Leu Ser Leu Cys Ser Ala Leu Ala Ala Gly His Leu Val
                450                 455                 460

Gln Ser His Met Thr His Asn Arg Ser Gln Ala Pro Thr Pro Ala Lys
465                 470                 475                 480

Gln Ser Gln Ala Asp Leu Gln Arg Leu Gln Asn Gly Ser Asn Ile Cys
                485                 490                 495

Ile Arg Ser

<210> SEQ ID NO 7
<211> LENGTH: 385
<212> TYPE: PRT
<213> ORGANISM: Cannabis sativa

<400> SEQUENCE: 7

Met Asn His Leu Arg Ala Glu Gly Pro Ala Ser Val Leu Ala Ile Gly
1               5                   10                  15

Thr Ala Asn Pro Glu Asn Ile Leu Leu Gln Asp Glu Phe Pro Asp Tyr
                20                  25                  30

Tyr Phe Arg Val Thr Lys Ser Glu His Met Thr Gln Leu Lys Glu Lys
                35                  40                  45

Phe Arg Lys Ile Cys Asp Lys Ser Met Ile Arg Lys Arg Asn Cys Phe
            50                  55                  60

Leu Asn Glu Glu His Leu Lys Gln Asn Pro Arg Leu Val Glu His Glu
```

```
            65                  70                  75                  80
        Met Gln Thr Leu Asp Ala Arg Gln Asp Met Leu Val Val Glu Val Pro
                            85                  90                  95

Lys Leu Gly Lys Asp Ala Cys Ala Lys Ala Ile Lys Glu Trp Gly Gln
                        100                 105                 110

Pro Lys Ser Lys Ile Thr His Leu Ile Phe Thr Ser Ala Ser Thr Thr
                    115                 120                 125

Asp Met Pro Gly Ala Asp Tyr His Cys Ala Lys Leu Leu Gly Leu Ser
                130                 135                 140

Pro Ser Val Lys Arg Val Met Met Tyr Gln Leu Gly Cys Tyr Gly Gly
        145                 150                 155                 160

Gly Thr Val Leu Arg Ile Ala Lys Asp Ile Ala Glu Asn Asn Lys Gly
                            165                 170                 175

Ala Arg Val Leu Ala Val Cys Cys Asp Ile Met Ala Cys Leu Phe Arg
                        180                 185                 190

Gly Pro Ser Glu Ser Asp Leu Glu Leu Leu Val Gly Gln Ala Ile Phe
                    195                 200                 205

Gly Asp Gly Ala Ala Ala Val Ile Val Gly Ala Glu Pro Asp Glu Ser
                210                 215                 220

Val Gly Glu Arg Pro Ile Phe Glu Leu Val Ser Thr Gly Gln Thr Ile
        225                 230                 235                 240

Leu Pro Asn Ser Glu Gly Thr Ile Gly Gly His Ile Arg Glu Ala Gly
                            245                 250                 255

Leu Ile Phe Asp Leu His Lys Asp Val Pro Met Leu Ile Ser Asn Asn
                        260                 265                 270

Ile Glu Lys Cys Leu Ile Glu Ala Phe Thr Pro Ile Gly Ile Ser Asp
                    275                 280                 285

Trp Asn Ser Ile Phe Trp Ile Thr His Pro Gly Gly Lys Ala Ile Leu
                290                 295                 300

Asp Lys Val Glu Glu Lys Leu His Leu Lys Ser Asp Lys Phe Val Asp
        305                 310                 315                 320

Ser Arg His Val Leu Ser Glu His Gly Asn Met Ser Ser Ser Thr Val
                            325                 330                 335

Leu Phe Val Met Asp Glu Leu Arg Lys Arg Ser Leu Glu Glu Gly Lys
                        340                 345                 350

Ser Thr Thr Gly Asp Gly Phe Glu Trp Gly Val Leu Phe Gly Phe Gly
                    355                 360                 365

Pro Gly Leu Thr Val Glu Arg Val Val Arg Ser Val Pro Ile Lys
                370                 375                 380

Tyr
        385

<210> SEQ ID NO 8
<211> LENGTH: 101
<212> TYPE: PRT
<213> ORGANISM: Cannabis sativa

<400> SEQUENCE: 8

Met Ala Val Lys His Leu Ile Val Leu Lys Phe Lys Asp Glu Ile Thr
        1               5                   10                  15

Glu Ala Gln Lys Glu Glu Phe Phe Lys Thr Tyr Val Asn Leu Val Asn
                        20                  25                  30

Ile Ile Pro Ala Met Lys Asp Val Tyr Trp Gly Lys Asp Val Thr Gln
                    35                  40                  45
```

```
Lys Asn Lys Glu Glu Gly Tyr Thr His Ile Val Glu Val Thr Phe Glu
 50                  55                  60

Ser Val Glu Thr Ile Gln Asp Tyr Ile Ile His Pro Ala His Val Gly
 65                  70                  75                  80

Phe Gly Asp Val Tyr Arg Ser Phe Trp Glu Lys Leu Leu Ile Phe Asp
                 85                  90                  95

Tyr Thr Pro Arg Lys
                100

<210> SEQ ID NO 9
<211> LENGTH: 395
<212> TYPE: PRT
<213> ORGANISM: Cannabis sativa

<400> SEQUENCE: 9

Met Gly Leu Ser Ser Val Cys Thr Phe Ser Phe Gln Thr Asn Tyr His
  1               5                  10                  15

Thr Leu Leu Asn Pro His Asn Asn Pro Lys Thr Ser Leu Leu Cys
                 20                  25                  30

Tyr Arg His Pro Lys Thr Pro Ile Lys Tyr Ser Tyr Asn Asn Phe Pro
                 35                  40                  45

Ser Lys His Cys Ser Thr Lys Ser Phe His Leu Gln Asn Lys Cys Ser
 50                  55                  60

Glu Ser Leu Ser Ile Ala Lys Asn Ser Ile Arg Ala Ala Thr Thr Asn
 65                  70                  75                  80

Gln Thr Glu Pro Pro Glu Ser Asp Asn His Ser Val Ala Thr Lys Ile
                 85                  90                  95

Leu Asn Phe Gly Lys Ala Cys Trp Lys Leu Gln Arg Pro Tyr Thr Ile
                100                 105                 110

Ile Ala Phe Thr Ser Cys Ala Cys Gly Leu Phe Gly Lys Glu Leu Leu
                115                 120                 125

His Asn Thr Asn Leu Ile Ser Trp Ser Leu Met Phe Lys Ala Phe Phe
                130                 135                 140

Phe Leu Val Ala Ile Leu Cys Ile Ala Ser Phe Thr Thr Ile Asn
145                 150                 155                 160

Gln Ile Tyr Asp Leu His Ile Asp Arg Ile Asn Lys Pro Asp Leu Pro
                165                 170                 175

Leu Ala Ser Gly Glu Ile Ser Val Asn Thr Ala Trp Ile Met Ser Ile
                180                 185                 190

Ile Val Ala Leu Phe Gly Leu Ile Ile Thr Ile Lys Met Lys Gly Gly
                195                 200                 205

Pro Leu Tyr Ile Phe Gly Tyr Cys Phe Gly Ile Phe Gly Gly Ile Val
                210                 215                 220

Tyr Ser Val Pro Pro Phe Arg Trp Lys Gln Asn Pro Ser Thr Ala Phe
225                 230                 235                 240

Leu Leu Asn Phe Leu Ala His Ile Ile Thr Asn Phe Thr Phe Tyr Tyr
                245                 250                 255

Ala Ser Arg Ala Ala Leu Gly Leu Pro Phe Glu Leu Arg Pro Ser Phe
                260                 265                 270

Thr Phe Leu Leu Ala Phe Met Lys Ser Met Gly Ser Ala Leu Ala Leu
                275                 280                 285

Ile Lys Asp Ala Ser Asp Val Glu Gly Asp Thr Lys Phe Gly Ile Ser
                290                 295                 300

Thr Leu Ala Ser Lys Tyr Gly Ser Arg Asn Leu Thr Leu Phe Cys Ser
305                 310                 315                 320
```

Gly Ile Val Leu Leu Ser Tyr Val Ala Ala Ile Leu Ala Gly Ile Ile
            325                 330                 335

Trp Pro Gln Ala Phe Asn Ser Asn Val Met Leu Leu Ser His Ala Ile
            340                 345                 350

Leu Ala Phe Trp Leu Ile Leu Gln Thr Arg Asp Phe Ala Leu Thr Asn
        355                 360                 365

Tyr Asp Pro Glu Ala Gly Arg Arg Phe Tyr Glu Phe Met Trp Lys Leu
    370                 375                 380

Tyr Tyr Ala Glu Tyr Leu Val Tyr Val Phe Ile
385                 390                 395

<210> SEQ ID NO 10
<211> LENGTH: 398
<212> TYPE: PRT
<213> ORGANISM: Cannabis sativa

<400> SEQUENCE: 10

Met Gly Leu Ser Leu Val Cys Thr Phe Ser Phe Gln Thr Asn Tyr His
1               5                   10                  15

Thr Leu Leu Asn Pro His Asn Lys Asn Pro Lys Asn Ser Leu Leu Ser
            20                  25                  30

Tyr Gln His Pro Lys Thr Pro Ile Ile Lys Ser Ser Tyr Asp Asn Phe
        35                  40                  45

Pro Ser Lys Tyr Cys Leu Thr Lys Asn Phe His Leu Leu Gly Leu Asn
    50                  55                  60

Ser His Asn Arg Ile Ser Ser Gln Ser Arg Ser Ile Arg Ala Gly Ser
65                  70                  75                  80

Asp Gln Ile Glu Gly Ser Pro His His Glu Ser Asp Asn Ser Ile Ala
                85                  90                  95

Thr Lys Ile Leu Asn Phe Gly His Thr Cys Trp Lys Leu Gln Arg Pro
            100                 105                 110

Tyr Val Val Lys Gly Met Ile Ser Ile Ala Cys Gly Leu Phe Gly Arg
        115                 120                 125

Glu Leu Phe Asn Asn Arg His Leu Phe Ser Trp Gly Leu Met Trp Lys
    130                 135                 140

Ala Phe Phe Ala Leu Val Pro Ile Leu Ser Phe Asn Phe Ala Ala
145                 150                 155                 160

Ile Met Asn Gln Ile Tyr Asp Val Asp Ile Asp Arg Ile Asn Lys Pro
                165                 170                 175

Asp Leu Pro Leu Val Ser Gly Glu Met Ser Ile Glu Thr Ala Trp Ile
            180                 185                 190

Leu Ser Ile Ile Val Ala Leu Thr Gly Leu Ile Val Thr Ile Lys Leu
        195                 200                 205

Lys Ser Ala Pro Leu Phe Val Phe Ile Tyr Ile Phe Gly Ile Phe Ala
    210                 215                 220

Gly Phe Ala Tyr Ser Val Pro Pro Ile Arg Trp Lys Gln Tyr Pro Phe
225                 230                 235                 240

Thr Asn Phe Leu Ile Thr Ile Ser Ser His Val Gly Leu Ala Phe Thr
                245                 250                 255

Ser Tyr Ser Ala Thr Thr Ser Ala Leu Gly Leu Pro Phe Val Trp Arg
            260                 265                 270

Pro Ala Phe Ser Phe Ile Ile Ala Phe Met Thr Val Met Gly Met Thr
        275                 280                 285

Ile Ala Phe Ala Lys Asp Ile Ser Asp Ile Glu Gly Asp Ala Lys Tyr

```
                290                 295                 300
Gly Val Ser Thr Val Ala Thr Lys Leu Gly Ala Arg Asn Met Thr Phe
305                 310                 315                 320

Val Val Ser Gly Val Leu Leu Leu Asn Tyr Leu Val Ser Ile Ser Ile
                325                 330                 335

Gly Ile Ile Trp Pro Gln Val Phe Lys Ser Asn Ile Met Ile Leu Ser
                340                 345                 350

His Ala Ile Leu Ala Phe Cys Leu Ile Phe Gln Thr Arg Glu Leu Ala
                355                 360                 365

Leu Ala Asn Tyr Ala Ser Ala Pro Ser Arg Gln Phe Phe Glu Phe Ile
                370                 375                 380

Trp Leu Leu Tyr Tyr Ala Glu Tyr Phe Val Tyr Val Phe Ile
385                 390                 395

<210> SEQ ID NO 11
<211> LENGTH: 400
<212> TYPE: PRT
<213> ORGANISM: Cannabis sativa

<400> SEQUENCE: 11

Met Val Phe Ser Ser Val Cys Ser Phe Pro Ser Ser Leu Gly Thr Asn
1               5                   10                  15

Phe Lys Leu Val Pro Arg Ser Asn Phe Lys Ala Ser Ser Ser His Tyr
                20                  25                  30

His Glu Ile Asn Asn Phe Ile Asn Asn Lys Pro Ile Lys Phe Ser Tyr
                35                  40                  45

Phe Ser Ser Arg Leu Tyr Cys Ser Ala Lys Pro Ile Val His Arg Glu
                50                  55                  60

Asn Lys Phe Thr Lys Ser Phe Ser Leu Ser His Leu Gln Arg Lys Ser
65              70                  75                  80

Ser Ile Lys Ala His Gly Glu Ile Glu Ala Asp Gly Ser Asn Gly Thr
                85                  90                  95

Ser Glu Phe Asn Val Met Lys Ser Gly Asn Ala Ile Trp Arg Phe Val
                100                 105                 110

Arg Pro Tyr Ala Ala Lys Gly Val Leu Phe Asn Ser Ala Ala Met Phe
                115                 120                 125

Ala Lys Glu Leu Val Gly Asn Leu Asn Leu Phe Ser Trp Pro Leu Met
                130                 135                 140

Phe Lys Ile Leu Ser Phe Thr Leu Val Ile Leu Cys Ile Phe Val Ser
145             150                 155                 160

Thr Ser Gly Ile Asn Gln Ile Tyr Asp Leu Asp Ile Asp Arg Leu Asn
                165                 170                 175

Lys Pro Asn Leu Pro Val Ala Ser Gly Glu Ile Ser Val Glu Leu Ala
                180                 185                 190

Trp Leu Leu Thr Ile Val Cys Thr Ile Ser Gly Leu Thr Leu Thr Ile
                195                 200                 205

Ile Thr Asn Ser Gly Pro Phe Phe Pro Phe Leu Tyr Ser Ala Ser Ile
                210                 215                 220

Phe Phe Gly Phe Leu Tyr Ser Ala Pro Pro Phe Arg Trp Lys Lys Asn
225                 230                 235                 240

Pro Phe Thr Ala Cys Phe Cys Asn Val Met Leu Tyr Val Gly Thr Ser
                245                 250                 255

Val Gly Val Tyr Tyr Ala Cys Lys Ala Ser Leu Gly Leu Pro Ala Asn
                260                 265                 270
```

```
Trp Ser Pro Ala Phe Cys Leu Leu Phe Trp Phe Ile Ser Leu Leu Ser
            275                 280                 285

Ile Pro Ile Ser Ile Ala Lys Asp Leu Ser Asp Ile Glu Gly Asp Arg
    290                 295                 300

Lys Phe Gly Ile Ile Thr Phe Ser Thr Lys Phe Gly Ala Lys Pro Ile
305                 310                 315                 320

Ala Tyr Ile Cys His Gly Leu Met Leu Leu Asn Tyr Val Ser Val Met
                325                 330                 335

Ala Ala Ala Ile Ile Trp Pro Gln Phe Phe Asn Ser Ser Val Ile Leu
            340                 345                 350

Leu Ser His Ala Phe Met Ala Ile Trp Val Leu Tyr Gln Ala Trp Ile
    355                 360                 365

Leu Glu Lys Ser Asn Tyr Ala Thr Glu Thr Cys Gln Lys Tyr Tyr Ile
370                 375                 380

Phe Leu Trp Ile Ile Phe Ser Leu Glu His Ala Phe Tyr Leu Phe Met
385                 390                 395                 400

<210> SEQ ID NO 12
<211> LENGTH: 307
<212> TYPE: PRT
<213> ORGANISM: Streptomyces sp. CL190

<400> SEQUENCE: 12

Met Ser Glu Ala Ala Asp Val Glu Arg Val Tyr Ala Ala Met Glu Glu
1               5                   10                  15

Ala Ala Gly Leu Leu Gly Val Ala Cys Ala Arg Asp Lys Ile Tyr Pro
            20                  25                  30

Leu Leu Ser Thr Phe Gln Asp Thr Leu Val Glu Gly Gly Ser Val Val
        35                  40                  45

Val Phe Ser Met Ala Ser Gly Arg His Ser Thr Glu Leu Asp Phe Ser
    50                  55                  60

Ile Ser Val Pro Thr Ser His Gly Asp Pro Tyr Ala Thr Val Val Glu
65                  70                  75                  80

Lys Gly Leu Phe Pro Ala Thr Gly His Pro Val Asp Asp Leu Leu Ala
                85                  90                  95

Asp Thr Gln Lys His Leu Pro Val Ser Met Phe Ala Ile Asp Gly Glu
            100                 105                 110

Val Thr Gly Gly Phe Lys Lys Thr Tyr Ala Phe Phe Pro Thr Asp Asn
        115                 120                 125

Met Pro Gly Val Ala Glu Leu Ser Ala Ile Pro Ser Met Pro Pro Ala
    130                 135                 140

Val Ala Glu Asn Ala Glu Leu Phe Ala Arg Tyr Gly Leu Asp Lys Val
145                 150                 155                 160

Ala Met Thr Ser Met Asp Tyr Lys Lys Arg Gln Val Asn Leu Tyr Phe
                165                 170                 175

Ser Glu Leu Ser Ala Gln Thr Leu Glu Ala Glu Ser Val Leu Ala Leu
            180                 185                 190

Val Arg Glu Leu Gly Leu His Val Pro Asn Glu Leu Gly Leu Lys Phe
        195                 200                 205

Cys Lys Arg Ser Phe Ser Val Tyr Pro Thr Leu Asn Trp Glu Thr Gly
    210                 215                 220

Lys Ile Asp Arg Leu Cys Phe Ala Val Ile Ser Asn Asp Pro Thr Leu
225                 230                 235                 240

Val Pro Ser Ser Asp Glu Gly Asp Ile Glu Lys Phe His Asn Tyr Ala
                245                 250                 255
```

Thr Lys Ala Pro Tyr Ala Tyr Val Gly Glu Lys Arg Thr Leu Val Tyr
                260                 265                 270

Gly Leu Thr Leu Ser Pro Lys Glu Glu Tyr Tyr Lys Leu Gly Ala Tyr
            275                 280                 285

Tyr His Ile Thr Asp Val Gln Arg Gly Leu Leu Lys Ala Phe Asp Ser
290                 295                 300

Leu Glu Asp
305

<210> SEQ ID NO 13
<211> LENGTH: 517
<212> TYPE: PRT
<213> ORGANISM: Cannabis sativa

<400> SEQUENCE: 13

Asn Pro Arg Glu Asn Phe Leu Lys Cys Phe Ser Lys His Ile Pro Asn
1               5                   10                  15

Asn Val Ala Asn Pro Lys Leu Val Tyr Thr Gln His Asp Gln Leu Tyr
            20                  25                  30

Met Ser Ile Leu Asn Ser Thr Ile Gln Asn Leu Arg Phe Ile Ser Asp
        35                  40                  45

Thr Thr Pro Lys Pro Leu Val Ile Val Thr Pro Ser Asn Asn Ser His
    50                  55                  60

Ile Gln Ala Thr Ile Leu Cys Ser Lys Lys Val Gly Leu Gln Ile Arg
65                  70                  75                  80

Thr Arg Ser Gly Gly His Asp Ala Glu Gly Met Ser Tyr Ile Ser Gln
                85                  90                  95

Val Pro Phe Val Val Val Asp Leu Arg Asn Met His Ser Ile Lys Ile
            100                 105                 110

Asp Val His Ser Gln Thr Ala Trp Val Glu Ala Gly Ala Thr Leu Gly
        115                 120                 125

Glu Val Tyr Tyr Trp Ile Asn Glu Lys Asn Glu Asn Leu Ser Phe Pro
    130                 135                 140

Gly Gly Tyr Cys Pro Thr Val Gly Val Gly Gly His Phe Ser Gly Gly
145                 150                 155                 160

Gly Tyr Gly Ala Leu Met Arg Asn Tyr Gly Leu Ala Ala Asp Asn Ile
                165                 170                 175

Ile Asp Ala His Leu Val Asn Val Asp Gly Lys Val Leu Asp Arg Lys
            180                 185                 190

Ser Met Gly Glu Asp Leu Phe Trp Ala Ile Arg Gly Gly Gly Gly Glu
        195                 200                 205

Asn Phe Gly Ile Ile Ala Ala Trp Lys Ile Lys Leu Val Ala Val Pro
    210                 215                 220

Ser Lys Ser Thr Ile Phe Ser Val Lys Lys Asn Met Glu Ile His Gly
225                 230                 235                 240

Leu Val Lys Leu Phe Asn Lys Trp Gln Asn Ile Ala Tyr Lys Tyr Asp
                245                 250                 255

Lys Asp Leu Val Leu Met Thr His Phe Ile Thr Lys Asn Ile Thr Asp
            260                 265                 270

Asn His Gly Lys Asn Lys Thr Val His Gly Tyr Phe Ser Ser Ile
        275                 280                 285

Phe His Gly Gly Val Asp Ser Leu Val Asp Leu Met Asn Lys Ser Phe
    290                 295                 300

Pro Glu Leu Gly Ile Lys Lys Thr Asp Cys Lys Glu Phe Ser Trp Ile

```
            305                 310                 315                 320
        Asp Thr Thr Ile Phe Tyr Ser Gly Val Val Asn Phe Asn Thr Ala Asn
                        325                 330                 335
        Phe Lys Lys Glu Ile Leu Leu Asp Arg Ser Ala Gly Lys Lys Thr Ala
                        340                 345                 350
        Phe Ser Ile Lys Leu Asp Tyr Val Lys Lys Pro Ile Pro Glu Thr Ala
                        355                 360                 365
        Met Val Lys Ile Leu Glu Lys Leu Tyr Glu Glu Asp Val Gly Ala Gly
                        370                 375                 380
        Met Tyr Val Leu Tyr Pro Tyr Gly Gly Ile Met Glu Glu Ile Ser Glu
        385                 390                 395                 400
        Ser Ala Ile Pro Phe Pro His Arg Ala Gly Ile Met Tyr Glu Leu Trp
                        405                 410                 415
        Tyr Thr Ala Ser Trp Glu Lys Gln Glu Asp Asn Glu Lys His Ile Asn
                        420                 425                 430
        Trp Val Arg Ser Val Tyr Asn Phe Thr Thr Pro Tyr Val Ser Gln Asn
                        435                 440                 445
        Pro Arg Leu Ala Tyr Leu Asn Tyr Arg Asp Leu Asp Leu Gly Lys Thr
                        450                 455                 460
        Asn His Ala Ser Pro Asn Asn Tyr Thr Gln Ala Arg Ile Trp Gly Glu
        465                 470                 475                 480
        Lys Tyr Phe Gly Lys Asn Phe Asn Arg Leu Val Lys Val Lys Thr Lys
                        485                 490                 495
        Val Asp Pro Asn Asn Phe Phe Arg Asn Glu Gln Ser Ile Pro Pro Leu
                        500                 505                 510
        Pro Pro His His His
                        515

<210> SEQ ID NO 14
<211> LENGTH: 516
<212> TYPE: PRT
<213> ORGANISM: Cannabis sativa

<400> SEQUENCE: 14

Asn Pro Arg Glu Asn Phe Leu Lys Cys Phe Ser Gln Tyr Ile Pro Asn
        1               5                   10                  15
        Asn Ala Thr Asn Leu Lys Leu Val Tyr Thr Gln Asn Asn Pro Leu Tyr
                        20                  25                  30
        Met Ser Val Leu Asn Ser Thr Ile His Asn Leu Arg Phe Thr Ser Asp
                        35                  40                  45
        Thr Thr Pro Lys Pro Leu Val Ile Val Thr Pro Ser His Val Ser His
                        50                  55                  60
        Ile Gln Gly Thr Ile Leu Cys Ser Lys Lys Val Gly Leu Gln Ile Arg
        65                  70                  75                  80
        Thr Arg Ser Gly Gly His Asp Ser Glu Gly Met Ser Tyr Ile Ser Gln
                        85                  90                  95
        Val Pro Phe Val Ile Val Asp Leu Arg Asn Met Arg Ser Ile Lys Ile
                        100                 105                 110
        Asp Val His Ser Gln Thr Ala Trp Val Glu Ala Gly Ala Thr Leu Gly
                        115                 120                 125
        Glu Val Tyr Tyr Trp Val Asn Glu Lys Asn Glu Asn Leu Ser Leu Ala
                        130                 135                 140
        Ala Gly Tyr Cys Pro Thr Val Cys Ala Gly Gly His Phe Gly Gly Gly
        145                 150                 155                 160
```

```
Gly Tyr Gly Pro Leu Met Arg Asn Tyr Gly Leu Ala Ala Asp Asn Ile
                165                 170                 175

Ile Asp Ala His Leu Val Asn Val His Gly Lys Val Leu Asp Arg Lys
            180                 185                 190

Ser Met Gly Glu Asp Leu Phe Trp Ala Leu Arg Gly Gly Ala Glu
        195                 200                 205

Ser Phe Gly Ile Ile Val Ala Trp Lys Ile Arg Leu Ala Val Pro
    210                 215                 220

Lys Ser Thr Met Phe Ser Val Lys Lys Ile Met Glu Ile His Glu Leu
225                 230                 235                 240

Val Lys Leu Val Asn Lys Trp Gln Asn Ile Ala Tyr Lys Tyr Asp Lys
                245                 250                 255

Asp Leu Leu Met Thr His Phe Ile Thr Arg Asn Ile Thr Asp Asn
            260                 265                 270

Gln Gly Lys Asn Lys Thr Ala Ile His Thr Tyr Phe Ser Ser Val Phe
                275                 280                 285

Leu Gly Gly Val Asp Ser Leu Val Asp Leu Met Asn Lys Ser Phe Pro
        290                 295                 300

Glu Leu Gly Ile Lys Lys Thr Asp Cys Arg Gln Leu Ser Trp Ile Asp
305                 310                 315                 320

Thr Ile Ile Phe Tyr Ser Gly Val Val Asn Tyr Asp Thr Asp Asn Phe
                325                 330                 335

Asn Lys Glu Ile Leu Leu Asp Arg Ser Ala Gly Gln Asn Gly Ala Phe
                340                 345                 350

Lys Ile Lys Leu Asp Tyr Val Lys Lys Pro Ile Pro Glu Ser Val Phe
            355                 360                 365

Val Gln Ile Leu Glu Lys Leu Tyr Glu Glu Asp Ile Gly Ala Gly Met
        370                 375                 380

Tyr Ala Leu Tyr Pro Tyr Gly Gly Ile Met Asp Glu Ile Ser Glu Ser
385                 390                 395                 400

Ala Ile Pro Phe Pro His Arg Ala Gly Ile Leu Tyr Glu Leu Trp Tyr
                405                 410                 415

Ile Cys Ser Trp Glu Lys Gln Glu Asp Asn Glu Lys His Leu Asn Trp
            420                 425                 430

Ile Arg Asn Ile Tyr Asn Phe Met Thr Pro Tyr Val Ser Lys Asn Pro
        435                 440                 445

Arg Leu Ala Tyr Leu Asn Tyr Arg Asp Leu Asp Ile Gly Ile Asn Asp
    450                 455                 460

Pro Lys Asn Pro Asn Asn Tyr Thr Gln Ala Arg Ile Trp Gly Glu Lys
465                 470                 475                 480

Tyr Phe Gly Lys Asn Phe Asp Arg Leu Val Lys Val Lys Thr Leu Val
                485                 490                 495

Asp Pro Asn Asn Phe Phe Arg Asn Glu Gln Ser Ile Pro Pro Leu Pro
            500                 505                 510

Arg His Arg His
        515

<210> SEQ ID NO 15
<211> LENGTH: 517
<212> TYPE: PRT
<213> ORGANISM: Cannabis sativa

<400> SEQUENCE: 15

Asn Pro Gln Glu Asn Phe Leu Lys Cys Phe Ser Glu Tyr Ile Pro Asn
1               5                   10                  15
```

Asn Pro Ala Asn Pro Lys Phe Ile Tyr Thr Gln His Asp Gln Leu Tyr
            20                  25                  30

Met Ser Val Leu Asn Ser Thr Ile Gln Asn Leu Arg Phe Thr Ser Asp
        35                  40                  45

Thr Thr Pro Lys Pro Leu Val Ile Val Thr Pro Ser Asn Val Ser His
    50                  55                  60

Ile Gln Ala Ser Ile Leu Cys Ser Lys Lys Val Gly Leu Gln Ile Arg
65                  70                  75                  80

Thr Arg Ser Gly Gly His Asp Ala Glu Gly Leu Ser Tyr Ile Ser Gln
                85                  90                  95

Val Pro Phe Ala Ile Val Asp Leu Arg Asn Met His Thr Val Lys Val
            100                 105                 110

Asp Ile His Ser Gln Thr Ala Trp Val Glu Ala Gly Ala Thr Leu Gly
        115                 120                 125

Glu Val Tyr Tyr Trp Ile Asn Glu Met Asn Glu Asn Phe Ser Phe Pro
    130                 135                 140

Gly Gly Tyr Cys Pro Thr Val Gly Val Gly Gly His Phe Ser Gly Gly
145                 150                 155                 160

Gly Tyr Gly Ala Leu Met Arg Asn Tyr Gly Leu Ala Ala Asp Asn Ile
                165                 170                 175

Ile Asp Ala His Leu Val Asn Val Asp Gly Lys Val Leu Asp Arg Lys
            180                 185                 190

Ser Met Gly Glu Asp Leu Phe Trp Ala Ile Arg Gly Gly Gly Gly Glu
        195                 200                 205

Asn Phe Gly Ile Ile Ala Ala Trp Lys Ile Lys Leu Val Val Val Pro
    210                 215                 220

Ser Lys Ala Thr Ile Phe Ser Val Lys Lys Asn Met Glu Ile His Gly
225                 230                 235                 240

Leu Val Lys Leu Phe Asn Lys Trp Gln Asn Ile Ala Tyr Lys Tyr Asp
                245                 250                 255

Lys Asp Leu Met Leu Thr Thr His Phe Arg Thr Arg Asn Ile Thr Asp
            260                 265                 270

Asn His Gly Lys Asn Lys Thr Thr Val His Gly Tyr Phe Ser Ser Ile
        275                 280                 285

Phe Leu Gly Gly Val Asp Ser Leu Val Asp Leu Met Asn Lys Ser Phe
    290                 295                 300

Pro Glu Leu Gly Ile Lys Lys Thr Asp Cys Lys Glu Leu Ser Trp Ile
305                 310                 315                 320

Asp Thr Thr Ile Phe Tyr Ser Gly Val Val Asn Tyr Asn Thr Ala Asn
                325                 330                 335

Phe Lys Lys Glu Ile Leu Leu Asp Arg Ser Ala Gly Lys Lys Thr Ala
            340                 345                 350

Phe Ser Ile Lys Leu Asp Tyr Val Lys Lys Leu Ile Pro Glu Thr Ala
        355                 360                 365

Met Val Lys Ile Leu Glu Lys Leu Tyr Glu Glu Val Gly Val Gly
    370                 375                 380

Met Tyr Val Leu Tyr Pro Tyr Gly Gly Ile Met Asp Glu Ile Ser Glu
385                 390                 395                 400

Ser Ala Ile Pro Phe Pro His Arg Ala Gly Ile Met Tyr Glu Leu Trp
                405                 410                 415

Tyr Thr Ala Thr Trp Glu Lys Gln Glu Asp Asn Glu Lys His Ile Asn
            420                 425                 430

```
Trp Val Arg Ser Val Tyr Asn Phe Thr Thr Pro Tyr Val Ser Gln Asn
            435                 440                 445

Pro Arg Leu Ala Tyr Leu Asn Tyr Arg Asp Leu Asp Leu Gly Lys Thr
450                 455                 460

Asn Pro Glu Ser Pro Asn Asn Tyr Thr Gln Ala Arg Ile Trp Gly Glu
465                 470                 475                 480

Lys Tyr Phe Gly Lys Asn Phe Asn Arg Leu Val Lys Val Lys Thr Lys
            485                 490                 495

Ala Asp Pro Asn Asn Phe Phe Arg Asn Glu Gln Ser Ile Pro Pro Leu
                500                 505                 510

Pro Pro Arg His His
            515

<210> SEQ ID NO 16
<211> LENGTH: 1671
<212> TYPE: PRT
<213> ORGANISM: Aspergillus parasiticus

<400> SEQUENCE: 16

Met Val Ile Gln Gly Lys Arg Leu Ala Ala Ser Ser Ile Gln Leu Leu
1               5                   10                  15

Ala Ser Ser Leu Asp Ala Lys Lys Leu Cys Tyr Glu Tyr Asp Glu Arg
                20                  25                  30

Gln Ala Pro Gly Val Thr Gln Ile Thr Glu Glu Ala Pro Thr Glu Gln
            35                  40                  45

Pro Pro Leu Ser Thr Pro Pro Ser Leu Pro Gln Thr Pro Asn Ile Ser
50                  55                  60

Pro Ile Ser Ala Ser Lys Ile Val Ile Asp Asp Val Ala Leu Ser Arg
65                  70                  75                  80

Val Gln Ile Val Gln Ala Leu Val Ala Arg Lys Leu Lys Thr Ala Ile
                85                  90                  95

Ala Gln Leu Pro Thr Ser Lys Ser Ile Lys Glu Leu Ser Gly Gly Arg
            100                 105                 110

Ser Ser Leu Gln Asn Glu Leu Val Gly Asp Ile His Asn Glu Phe Ser
        115                 120                 125

Ser Ile Pro Asp Ala Pro Glu Gln Ile Leu Leu Arg Asp Phe Gly Asp
    130                 135                 140

Ala Asn Pro Thr Val Gln Leu Gly Lys Thr Ser Ser Ala Ala Val Ala
145                 150                 155                 160

Lys Leu Ile Ser Ser Lys Met Pro Ser Asp Phe Asn Ala Asn Ala Ile
                165                 170                 175

Arg Ala His Leu Ala Asn Lys Trp Gly Leu Gly Pro Leu Arg Gln Thr
            180                 185                 190

Ala Val Leu Leu Tyr Ala Ile Ala Ser Glu Pro Pro Ser Arg Leu Ala
        195                 200                 205

Ser Ser Ser Ala Ala Glu Glu Tyr Trp Asp Asn Val Ser Ser Met Tyr
    210                 215                 220

Ala Glu Ser Cys Gly Ile Thr Leu Arg Pro Arg Gln Asp Thr Met Asn
225                 230                 235                 240

Glu Asp Ala Met Ala Ser Ser Ile Asp Pro Ala Val Val Ala Glu
                245                 250                 255

Phe Ser Lys Gly His Arg Arg Leu Gly Val Gln Gln Phe Gln Ala Leu
            260                 265                 270

Ala Glu Tyr Leu Gln Ile Asp Leu Ser Gly Ser Gln Ala Ser Gln Ser
        275                 280                 285
```

```
Asp Ala Leu Val Ala Glu Leu Gln Gln Lys Val Asp Leu Trp Thr Ala
    290                 295                 300

Glu Met Thr Pro Glu Phe Leu Ala Gly Ile Ser Pro Met Leu Asp Val
305                 310                 315                 320

Lys Lys Ser Arg Arg Tyr Gly Ser Trp Trp Asn Met Ala Arg Gln Asp
                325                 330                 335

Val Leu Ala Phe Tyr Arg Arg Pro Ser Tyr Ser Glu Phe Val Asp Asp
                340                 345                 350

Ala Leu Ala Phe Lys Val Phe Leu Asn Arg Leu Cys Asn Arg Ala Asp
                355                 360                 365

Glu Ala Leu Leu Asn Met Val Arg Ser Leu Ser Cys Asp Ala Tyr Phe
    370                 375                 380

Lys Gln Gly Ser Leu Pro Gly Tyr His Ala Ala Ser Arg Leu Leu Glu
385                 390                 395                 400

Gln Ala Ile Thr Ser Thr Val Ala Asp Cys Pro Lys Ala Arg Leu Ile
                405                 410                 415

Leu Pro Ala Val Gly Pro His Thr Thr Ile Thr Lys Asp Gly Thr Ile
                420                 425                 430

Glu Tyr Ala Glu Ala Pro Arg Gln Gly Val Ser Gly Pro Thr Ala Tyr
    435                 440                 445

Ile Gln Ser Leu Arg Gln Gly Ala Ser Phe Ile Gly Leu Lys Ser Ala
    450                 455                 460

Asp Val Asp Thr Gln Ser Asn Leu Thr Asp Ala Leu Leu Asp Ala Met
465                 470                 475                 480

Cys Leu Ala Leu His Asn Gly Ile Ser Phe Val Gly Lys Thr Phe Leu
                485                 490                 495

Val Thr Gly Ala Gly Gln Gly Ser Ile Gly Ala Gly Val Val Arg Leu
                500                 505                 510

Leu Leu Glu Gly Gly Ala Arg Val Leu Val Thr Thr Ser Arg Glu Pro
    515                 520                 525

Ala Thr Thr Ser Arg Tyr Phe Gln Gln Met Tyr Asp Asn His Gly Ala
    530                 535                 540

Lys Phe Ser Glu Leu Arg Val Val Pro Cys Asn Leu Ala Ser Ala Gln
545                 550                 555                 560

Asp Cys Glu Gly Leu Ile Arg His Val Tyr Asp Pro Arg Gly Leu Asn
                565                 570                 575

Trp Asp Leu Asp Ala Ile Leu Pro Phe Ala Ala Ser Asp Tyr Ser
                580                 585                 590

Thr Glu Met His Asp Ile Arg Gly Gln Ser Glu Leu Gly His Arg Leu
    595                 600                 605

Met Leu Val Asn Val Phe Arg Val Leu Gly His Ile Val His Cys Lys
    610                 615                 620

Arg Asp Ala Gly Val Asp Cys His Pro Thr Gln Val Leu Leu Pro Leu
625                 630                 635                 640

Ser Pro Asn His Gly Ile Phe Gly Gly Asp Gly Met Tyr Pro Glu Ser
                645                 650                 655

Lys Leu Ala Leu Glu Ser Leu Phe His Arg Ile Arg Ser Glu Ser Trp
                660                 665                 670

Ser Asp Gln Leu Ser Ile Cys Gly Val Arg Ile Gly Trp Thr Arg Ser
    675                 680                 685

Thr Gly Leu Met Thr Ala His Asp Ile Ile Ala Glu Thr Val Glu Glu
    690                 695                 700
```

-continued

```
His Gly Ile Arg Thr Phe Ser Val Ala Glu Met Ala Leu Asn Ile Ala
705                 710                 715                 720

Met Leu Leu Thr Pro Asp Phe Val Ala His Cys Glu Asp Gly Pro Leu
            725                 730                 735

Asp Ala Asp Phe Thr Gly Ser Leu Gly Thr Leu Gly Ser Ile Pro Gly
                740                 745                 750

Phe Leu Ala Gln Leu His Gln Lys Val Gln Leu Ala Ala Glu Val Ile
                755                 760                 765

Arg Ala Val Gln Ala Glu Asp Glu His Glu Arg Phe Leu Ser Pro Gly
770                 775                 780

Thr Lys Pro Thr Leu Gln Ala Pro Val Ala Pro Met His Pro Arg Ser
785                 790                 795                 800

Ser Leu Arg Val Gly Tyr Pro Arg Leu Pro Asp Tyr Glu Gln Glu Ile
                805                 810                 815

Arg Pro Leu Ser Pro Arg Leu Glu Arg Leu Gln Asp Pro Ala Asn Ala
                820                 825                 830

Val Val Val Val Gly Tyr Ser Glu Leu Gly Pro Trp Gly Ser Ala Arg
                835                 840                 845

Leu Arg Trp Glu Ile Glu Ser Gln Gly Gln Trp Thr Ser Ala Gly Tyr
850                 855                 860

Val Glu Leu Ala Trp Leu Met Asn Leu Ile Arg His Val Asn Asp Glu
865                 870                 875                 880

Ser Tyr Val Gly Trp Val Asp Thr Gln Thr Gly Lys Pro Val Arg Asp
                885                 890                 895

Gly Glu Ile Gln Ala Leu Tyr Gly Asp His Ile Asp Asn His Thr Gly
                900                 905                 910

Ile Arg Pro Ile Gln Ser Thr Ser Tyr Asn Pro Glu Arg Met Glu Val
                915                 920                 925

Leu Gln Glu Val Ala Val Glu Glu Asp Leu Pro Glu Phe Glu Val Ser
930                 935                 940

Gln Leu Thr Ala Asp Ala Met Arg Leu Arg His Gly Ala Asn Val Ser
945                 950                 955                 960

Ile Arg Pro Ser Gly Asn Pro Asp Ala Cys His Val Lys Leu Lys Arg
                965                 970                 975

Gly Ala Val Ile Leu Val Pro Lys Thr Val Pro Phe Val Trp Gly Ser
                980                 985                 990

Cys Ala Gly Glu Leu Pro Lys Gly Trp Thr Pro Ala Lys Tyr Gly Ile
                995                 1000                1005

Pro Glu Asn Leu Ile His Gln Val Asp Pro Val Thr Leu Tyr Thr
    1010                1015                1020

Ile Cys Cys Val Ala Glu Ala Phe Tyr Ser Ala Gly Ile Thr His
    1025                1030                1035

Pro Leu Glu Val Phe Arg His Ile His Leu Ser Glu Leu Gly Asn
    1040                1045                1050

Phe Ile Gly Ser Ser Met Gly Gly Pro Thr Lys Thr Arg Gln Leu
    1055                1060                1065

Tyr Arg Asp Val Tyr Phe Asp His Glu Ile Pro Ser Asp Val Leu
    1070                1075                1080

Gln Asp Thr Tyr Leu Asn Thr Pro Ala Ala Trp Val Asn Met Leu
    1085                1090                1095

Leu Leu Gly Cys Thr Gly Pro Ile Lys Thr Pro Val Gly Ala Cys
    1100                1105                1110

Ala Thr Gly Val Glu Ser Ile Asp Ser Gly Tyr Glu Ser Ile Met
```

```
            1115                1120                1125

Ala Gly Lys Thr Lys Met Cys Leu Val Gly Gly Tyr Asp Asp Leu
            1130                1135                1140

Gln Glu Glu Ala Ser Tyr Gly Phe Ala Gln Leu Lys Ala Thr Val
            1145                1150                1155

Asn Val Glu Glu Glu Ile Ala Cys Gly Arg Gln Pro Ser Glu Met
            1160                1165                1170

Ser Arg Pro Met Ala Glu Ser Arg Ala Gly Phe Val Glu Ala His
            1175                1180                1185

Gly Cys Gly Val Gln Leu Leu Cys Arg Gly Asp Ile Ala Leu Gln
            1190                1195                1200

Met Gly Leu Pro Ile Tyr Ala Val Ile Ala Ser Ser Ala Met Ala
            1205                1210                1215

Ala Asp Lys Ile Gly Ser Ser Val Pro Ala Pro Gly Gln Gly Ile
            1220                1225                1230

Leu Ser Phe Ser Arg Glu Arg Ala Arg Ser Ser Met Ile Ser Val
            1235                1240                1245

Thr Ser Arg Pro Ser Ser Arg Ser Ser Thr Ser Ser Glu Val Ser
            1250                1255                1260

Asp Lys Ser Ser Leu Thr Ser Ile Thr Ser Ile Ser Asn Pro Ala
            1265                1270                1275

Pro Arg Ala Gln Arg Ala Arg Ser Thr Thr Asp Met Ala Pro Leu
            1280                1285                1290

Arg Ala Ala Leu Ala Thr Trp Gly Leu Thr Ile Asp Asp Leu Asp
            1295                1300                1305

Val Ala Ser Leu His Gly Thr Ser Thr Arg Gly Asn Asp Leu Asn
            1310                1315                1320

Glu Pro Glu Val Ile Glu Thr Gln Met Arg His Leu Gly Arg Thr
            1325                1330                1335

Pro Gly Arg Pro Leu Trp Ala Ile Cys Gln Lys Ser Val Thr Gly
            1340                1345                1350

His Pro Lys Ala Pro Ala Ala Trp Met Leu Asn Gly Cys Leu
            1355                1360                1365

Gln Val Leu Asp Ser Gly Leu Val Pro Gly Asn Arg Asn Leu Asp
            1370                1375                1380

Thr Leu Asp Glu Ala Leu Arg Ser Ala Ser His Leu Cys Phe Pro
            1385                1390                1395

Thr Arg Thr Val Gln Leu Arg Glu Val Lys Ala Phe Leu Leu Thr
            1400                1405                1410

Ser Phe Gly Phe Gly Gln Lys Gly Gly Gln Val Val Gly Val Ala
            1415                1420                1425

Pro Lys Tyr Phe Phe Ala Thr Leu Pro Arg Pro Glu Val Glu Gly
            1430                1435                1440

Tyr Tyr Arg Lys Val Arg Val Arg Thr Glu Ala Gly Asp Arg Ala
            1445                1450                1455

Tyr Ala Ala Ala Val Met Ser Gln Ala Val Val Lys Ile Gln Thr
            1460                1465                1470

Gln Asn Pro Tyr Asp Glu Pro Asp Ala Pro Arg Ile Phe Leu Asp
            1475                1480                1485

Pro Leu Ala Arg Ile Ser Gln Asp Pro Ser Thr Gly Gln Tyr Arg
            1490                1495                1500

Phe Arg Ser Asp Ala Thr Pro Ala Leu Asp Asp Ala Leu Pro
            1505                1510                1515
```

-continued

```
Pro Pro Gly Glu Pro Thr Glu Leu Val Lys Gly Ile Ser Ser Ala
    1520            1525                1530

Trp Ile Glu Glu Lys Val Arg Pro His Met Ser Pro Gly Gly Thr
    1535            1540                1545

Val Gly Val Asp Leu Val Pro Leu Ala Ser Phe Asp Ala Tyr Lys
    1550            1555                1560

Asn Ala Ile Phe Val Glu Arg Asn Tyr Thr Val Arg Glu Arg Asp
    1565            1570                1575

Trp Ala Glu Lys Ser Ala Asp Val Arg Ala Ala Tyr Ala Ser Arg
    1580            1585                1590

Trp Cys Ala Lys Glu Ala Val Phe Lys Cys Leu Gln Thr His Ser
    1595            1600                1605

Gln Gly Ala Gly Ala Ala Met Lys Glu Ile Glu Ile Glu His Gly
    1610            1615                1620

Gly Asn Gly Ala Pro Lys Val Lys Leu Arg Gly Ala Ala Gln Thr
    1625            1630                1635

Ala Ala Arg Gln Arg Gly Leu Glu Gly Val Gln Leu Ser Ile Ser
    1640            1645                1650

Tyr Gly Asp Asp Ala Val Ile Ala Val Ala Leu Gly Leu Met Ser
    1655            1660                1665

Gly Ala Ser
    1670

<210> SEQ ID NO 17
<211> LENGTH: 1888
<212> TYPE: PRT
<213> ORGANISM: Aspergillus parasiticus

<400> SEQUENCE: 17

Met Gly Ser Val Ser Arg Glu His Glu Ser Ile Pro Ile Gln Ala Ala
1               5                   10                  15

Gln Arg Gly Ala Ala Arg Ile Cys Ala Ala Phe Gly Gly Gln Gly Ser
            20                  25                  30

Asn Asn Leu Asp Val Leu Lys Gly Leu Leu Glu Leu Tyr Lys Arg Tyr
        35                  40                  45

Gly Pro Asp Leu Asp Glu Leu Leu Asp Val Ala Ser Asn Thr Leu Ser
    50                  55                  60

Gln Leu Ala Ser Ser Pro Ala Ala Ile Asp Val His Glu Pro Trp Gly
65                  70                  75                  80

Phe Asp Leu Arg Gln Trp Leu Thr Thr Pro Glu Val Ala Pro Ser Lys
                85                  90                  95

Glu Ile Leu Ala Leu Pro Pro Arg Ser Phe Pro Leu Asn Thr Leu Leu
            100                 105                 110

Ser Leu Ala Leu Tyr Cys Ala Thr Cys Arg Glu Leu Glu Leu Asp Pro
        115                 120                 125

Gly Gln Phe Arg Ser Leu Leu His Ser Ser Thr Gly His Ser Gln Gly
    130                 135                 140

Ile Leu Ala Ala Val Ala Ile Thr Gln Ala Glu Ser Trp Pro Thr Phe
145                 150                 155                 160

Tyr Asp Ala Cys Arg Thr Val Leu Gln Ile Ser Phe Trp Ile Gly Leu
                165                 170                 175

Glu Ala Tyr Leu Phe Thr Pro Ser Ser Ala Ala Ser Asp Ala Met Ile
            180                 185                 190

Gln Asp Cys Ile Glu His Gly Glu Gly Leu Leu Ser Ser Met Leu Ser
```

```
            195                 200                 205
Val Ser Gly Leu Ser Arg Ser Gln Val Glu Arg Val Ile Glu His Val
210                 215                 220
Asn Lys Gly Leu Gly Glu Cys Asn Arg Trp Val His Leu Ala Leu Val
225                 230                 235                 240
Asn Ser His Glu Lys Phe Val Leu Ala Gly Pro Gln Ser Leu Trp
                245                 250                 255
Ala Val Cys Leu His Val Arg Arg Ile Arg Ala Asp Asn Asp Leu Asp
                260                 265                 270
Gln Ser Arg Ile Leu Phe Arg Asn Arg Lys Pro Ile Val Asp Ile Leu
                275                 280                 285
Phe Leu Pro Ile Ser Ala Pro Phe His Thr Pro Tyr Leu Asp Gly Val
                290                 295                 300
Gln Asp Arg Val Ile Glu Ala Leu Ser Ser Ala Ser Leu Ala Leu His
305                 310                 315                 320
Ser Ile Lys Ile Pro Leu Tyr His Thr Gly Thr Gly Ser Asn Leu Gln
                325                 330                 335
Glu Leu Gln Pro His Gln Leu Ile Pro Thr Leu Ile Arg Ala Ile Thr
                340                 345                 350
Val Asp Gln Leu Asp Trp Pro Leu Val Cys Arg Gly Leu Asn Ala Thr
                355                 360                 365
His Val Leu Asp Phe Gly Pro Gly Gln Thr Cys Ser Leu Ile Gln Glu
                370                 375                 380
Leu Thr Gln Gly Thr Gly Val Ser Val Ile Gln Leu Thr Thr Gln Ser
385                 390                 395                 400
Gly Pro Lys Pro Val Gly Gly His Leu Ala Ala Val Asn Trp Glu Ala
                405                 410                 415
Glu Phe Gly Leu Arg Leu His Ala Asn Val His Gly Ala Ala Lys Leu
                420                 425                 430
His Asn Arg Met Thr Thr Leu Leu Gly Lys Pro Pro Val Met Val Ala
                435                 440                 445
Gly Met Thr Pro Thr Thr Val Arg Trp Asp Phe Val Ala Ala Val Ala
                450                 455                 460
Gln Ala Gly Tyr His Val Glu Leu Ala Gly Gly Tyr His Ala Glu
465                 470                 475                 480
Arg Gln Phe Glu Ala Glu Ile Arg Arg Leu Ala Thr Ala Ile Pro Ala
                485                 490                 495
Asp His Gly Ile Thr Cys Asn Leu Leu Tyr Ala Lys Pro Thr Thr Phe
                500                 505                 510
Ser Trp Gln Ile Ser Val Ile Lys Asp Leu Val Arg Gln Gly Val Pro
                515                 520                 525
Val Glu Gly Ile Thr Ile Gly Ala Gly Ile Pro Ser Pro Glu Val Val
                530                 535                 540
Gln Glu Cys Val Gln Ser Ile Gly Leu Lys His Ile Ser Phe Lys Pro
545                 550                 555                 560
Gly Ser Phe Glu Ala Ile His Gln Val Ile Gln Ile Ala Arg Thr His
                565                 570                 575
Pro Asn Phe Leu Ile Gly Leu Gln Trp Thr Ala Gly Arg Gly Gly Gly
                580                 585                 590
His His Ser Trp Glu Asp Phe His Gly Pro Ile Leu Ala Thr Tyr Ala
                595                 600                 605
Gln Ile Arg Ser Cys Pro Asn Ile Leu Leu Val Val Gly Ser Gly Phe
                610                 615                 620
```

Gly Gly Gly Pro Asp Thr Phe Pro Tyr Leu Thr Gln Trp Ala Gln
625                 630                 635                 640

Ala Phe Gly Tyr Pro Cys Met Pro Phe Asp Gly Val Leu Leu Gly Ser
            645                 650                 655

Arg Met Met Val Ala Arg Glu Ala His Thr Ser Ala Gln Ala Lys Arg
        660                 665                 670

Leu Ile Ile Asp Ala Gln Gly Val Gly Asp Ala Asp Trp His Lys Ser
    675                 680                 685

Phe Asp Glu Pro Thr Gly Gly Val Val Thr Val Asn Ser Glu Phe Gly
690                 695                 700

Gln Pro Ile His Val Leu Ala Thr Arg Gly Val Met Leu Trp Lys Glu
705                 710                 715                 720

Leu Asp Asn Arg Val Phe Ser Ile Lys Asp Thr Ser Lys Arg Leu Glu
                725                 730                 735

Tyr Leu Arg Asn His Arg Gln Glu Ile Val Ser Arg Leu Asn Ala Asp
            740                 745                 750

Phe Ala Arg Pro Trp Phe Ala Val Asp Gly His Gly Gln Asn Val Glu
        755                 760                 765

Leu Glu Asp Met Thr Tyr Leu Glu Val Leu Arg Arg Leu Cys Asp Leu
    770                 775                 780

Thr Tyr Val Ser His Gln Lys Arg Trp Val Asp Pro Ser Tyr Arg Ile
785                 790                 795                 800

Leu Leu Leu Asp Phe Val His Leu Leu Arg Glu Arg Phe Gln Cys Ala
                805                 810                 815

Ile Asp Asn Pro Gly Glu Tyr Pro Leu Asp Ile Ile Val Arg Val Glu
            820                 825                 830

Glu Ser Leu Lys Asp Lys Ala Tyr Arg Thr Leu Tyr Pro Glu Asp Val
        835                 840                 845

Ser Leu Leu Met His Leu Phe Ser Arg Asp Ile Lys Pro Val Pro
    850                 855                 860

Phe Ile Pro Arg Leu Asp Glu Arg Phe Glu Thr Trp Phe Lys Lys Asp
865                 870                 875                 880

Ser Leu Trp Gln Ser Glu Asp Val Glu Ala Val Ile Gly Gln Asp Val
                885                 890                 895

Gln Arg Ile Phe Ile Ile Gln Gly Pro Met Ala Val Gln Tyr Ser Ile
            900                 905                 910

Ser Asp Asp Glu Ser Val Lys Asp Ile Leu His Asn Ile Cys Asn His
        915                 920                 925

Tyr Val Glu Ala Leu Gln Ala Asp Ser Arg Glu Thr Ser Ile Gly Asp
    930                 935                 940

Val His Ser Ile Thr Gln Lys Pro Leu Ser Ala Phe Pro Gly Leu Lys
945                 950                 955                 960

Val Thr Thr Asn Arg Val Gln Gly Leu Tyr Lys Phe Glu Lys Val Gly
                965                 970                 975

Ala Val Pro Glu Met Asp Val Leu Phe Glu His Ile Val Gly Leu Ser
            980                 985                 990

Lys Ser Trp Ala Arg Thr Cys Leu Met Ser Lys Ser Val Phe Arg Asp
        995                 1000                1005

Gly Ser Arg Leu His Asn Pro Ile Arg Ala Ala Leu Gln Leu Gln
    1010                1015                1020

Arg Gly Asp Thr Ile Glu Val Leu Leu Thr Ala Asp Ser Glu Ile
    1025                1030                1035

```
Arg Lys Ile Arg Leu Ile Ser Pro Thr Gly Asp Gly Gly Ser Thr
    1040                1045                1050

Ser Lys Val Val Leu Glu Ile Val Ser Asn Asp Gly Gln Arg Val
    1055                1060                1065

Phe Ala Thr Leu Ala Pro Asn Ile Pro Leu Ser Pro Glu Pro Ser
    1070                1075                1080

Val Val Phe Cys Phe Lys Val Asp Gln Lys Pro Asn Glu Trp Thr
    1085                1090                1095

Leu Glu Glu Asp Ala Ser Gly Arg Ala Glu Arg Ile Lys Ala Leu
    1100                1105                1110

Tyr Met Ser Leu Trp Asn Leu Gly Phe Pro Asn Lys Ala Ser Val
    1115                1120                1125

Leu Gly Leu Asn Ser Gln Phe Thr Gly Glu Glu Leu Met Ile Thr
    1130                1135                1140

Thr Asp Lys Ile Arg Asp Phe Glu Arg Val Leu Arg Gln Thr Ser
    1145                1150                1155

Pro Leu Gln Leu Gln Ser Trp Asn Pro Gln Gly Cys Val Pro Ile
    1160                1165                1170

Asp Tyr Cys Val Val Ile Ala Trp Ser Ala Leu Thr Lys Pro Leu
    1175                1180                1185

Met Val Ser Ser Leu Lys Cys Asp Leu Leu Asp Leu Leu His Ser
    1190                1195                1200

Ala Ile Ser Phe His Tyr Ala Pro Ser Val Lys Pro Leu Arg Val
    1205                1210                1215

Gly Asp Ile Val Lys Thr Ser Ser Arg Ile Leu Ala Val Ser Val
    1220                1225                1230

Arg Pro Arg Gly Thr Met Leu Thr Val Ser Ala Asp Ile Gln Arg
    1235                1240                1245

Gln Gly Gln His Val Val Thr Val Lys Ser Asp Phe Phe Leu Gly
    1250                1255                1260

Gly Pro Val Leu Ala Cys Glu Thr Pro Phe Glu Leu Thr Glu Glu
    1265                1270                1275

Pro Glu Met Val Val His Val Asp Ser Glu Val Arg Arg Ala Ile
    1280                1285                1290

Leu His Ser Arg Lys Trp Leu Met Arg Glu Asp Arg Ala Leu Asp
    1295                1300                1305

Leu Leu Gly Arg Gln Leu Leu Phe Arg Leu Lys Ser Glu Lys Leu
    1310                1315                1320

Phe Arg Pro Asp Gly Gln Leu Ala Leu Leu Gln Val Thr Gly Ser
    1325                1330                1335

Val Phe Ser Tyr Ser Pro Asp Gly Ser Thr Thr Ala Phe Gly Arg
    1340                1345                1350

Val Tyr Phe Glu Ser Glu Ser Cys Thr Gly Asn Val Val Met Asp
    1355                1360                1365

Phe Leu His Arg Tyr Gly Ala Pro Arg Ala Gln Leu Leu Glu Leu
    1370                1375                1380

Gln His Pro Gly Trp Thr Gly Thr Ser Thr Val Ala Val Arg Gly
    1385                1390                1395

Pro Arg Arg Ser Gln Ser Tyr Ala Arg Val Ser Leu Asp His Asn
    1400                1405                1410

Pro Ile His Val Cys Pro Ala Phe Ala Arg Tyr Ala Gly Leu Ser
    1415                1420                1425

Gly Pro Ile Val His Gly Met Glu Thr Ser Ala Met Met Arg Arg
```

```
            1430                1435                1440

Ile  Ala  Glu  Trp  Ala  Ile  Gly  Asp  Ala  Asp  Arg  Ser  Arg  Phe  Arg
     1445                1450                1455

Ser  Trp  His  Ile  Thr  Leu  Gln  Ala  Pro  Val  His  Pro  Asn  Asp  Pro
     1460                1465                1470

Leu  Arg  Val  Glu  Leu  Gln  His  Lys  Ala  Met  Glu  Asp  Gly  Glu  Met
     1475                1480                1485

Val  Leu  Lys  Val  Gln  Ala  Phe  Asn  Glu  Arg  Thr  Glu  Glu  Arg  Val
     1490                1495                1500

Ala  Glu  Ala  Asp  Ala  His  Val  Glu  Gln  Glu  Thr  Thr  Ala  Tyr  Val
     1505                1510                1515

Phe  Cys  Gly  Gln  Gly  Ser  Gln  Arg  Gln  Gly  Met  Gly  Met  Asp  Leu
     1520                1525                1530

Tyr  Val  Asn  Cys  Pro  Glu  Ala  Lys  Ala  Leu  Trp  Ala  Arg  Ala  Asp
     1535                1540                1545

Lys  His  Leu  Trp  Glu  Lys  Tyr  Gly  Phe  Ser  Ile  Leu  His  Ile  Val
     1550                1555                1560

Gln  Asn  Asn  Pro  Pro  Ala  Leu  Thr  Val  His  Phe  Gly  Ser  Gln  Arg
     1565                1570                1575

Gly  Arg  Arg  Ile  Arg  Ala  Asn  Tyr  Leu  Arg  Met  Met  Gly  Gln  Pro
     1580                1585                1590

Pro  Ile  Asp  Gly  Arg  His  Pro  Pro  Ile  Leu  Lys  Gly  Leu  Thr  Arg
     1595                1600                1605

Asn  Ser  Thr  Ser  Tyr  Thr  Phe  Ser  Tyr  Ser  Gln  Gly  Leu  Leu  Met
     1610                1615                1620

Ser  Thr  Gln  Phe  Ala  Gln  Pro  Ala  Leu  Ala  Leu  Met  Glu  Met  Ala
     1625                1630                1635

Gln  Phe  Glu  Trp  Leu  Lys  Ala  Gln  Gly  Val  Val  Gln  Lys  Gly  Ala
     1640                1645                1650

Arg  Phe  Ala  Gly  His  Ser  Leu  Gly  Glu  Tyr  Ala  Ala  Leu  Gly  Ala
     1655                1660                1665

Cys  Ala  Ser  Phe  Leu  Ser  Phe  Glu  Asp  Leu  Ile  Ser  Leu  Ile  Phe
     1670                1675                1680

Tyr  Arg  Gly  Leu  Lys  Met  Gln  Asn  Ala  Leu  Pro  Arg  Asp  Ala  Asn
     1685                1690                1695

Gly  His  Thr  Asp  Tyr  Gly  Met  Leu  Ala  Ala  Asp  Pro  Ser  Arg  Ile
     1700                1705                1710

Gly  Lys  Gly  Phe  Glu  Glu  Ala  Ser  Leu  Lys  Cys  Leu  Val  His  Ile
     1715                1720                1725

Ile  Gln  Gln  Glu  Thr  Gly  Trp  Phe  Val  Glu  Val  Val  Asn  Tyr  Asn
     1730                1735                1740

Ile  Asn  Ser  Gln  Gln  Tyr  Val  Cys  Ala  Gly  His  Phe  Arg  Ala  Leu
     1745                1750                1755

Trp  Met  Leu  Gly  Lys  Ile  Cys  Asp  Asp  Leu  Ser  Cys  His  Pro  Gln
     1760                1765                1770

Pro  Glu  Thr  Val  Glu  Gly  Gln  Glu  Leu  Arg  Ala  Met  Val  Trp  Lys
     1775                1780                1785

His  Val  Pro  Thr  Val  Glu  Gln  Val  Pro  Arg  Glu  Asp  Arg  Met  Glu
     1790                1795                1800

Arg  Gly  Arg  Ala  Thr  Ile  Pro  Leu  Pro  Gly  Ile  Asp  Ile  Pro  Tyr
     1805                1810                1815

His  Ser  Thr  Met  Leu  Arg  Gly  Glu  Ile  Glu  Pro  Tyr  Arg  Glu  Tyr
     1820                1825                1830
```

```
Leu Ser Glu Arg Ile Lys Val Gly Asp Val Lys Pro Cys Glu Leu
    1835            1840                1845

Val Gly Arg Trp Ile Pro Asn Val Val Gly Gln Pro Phe Ser Val
    1850            1855                1860

Asp Lys Ser Tyr Val Gln Leu Val His Gly Ile Thr Gly Ser Pro
    1865            1870                1875

Arg Leu His Ser Leu Leu Gln Gln Met Ala
    1880            1885

<210> SEQ ID NO 18
<211> LENGTH: 1559
<212> TYPE: PRT
<213> ORGANISM: Aspergillus nidulans

<400> SEQUENCE: 18

Met Thr Gln Lys Thr Ile Gln Val Pro Arg Gln Gly Leu Glu Leu
1               5                   10                  15

Leu Ala Ser Thr Gln Asp Leu Ala Gln Leu Cys Tyr Ile Tyr Gly Glu
            20                  25                  30

Pro Ala Glu Gly Glu Asp Ser Thr Ala Asp Glu Ser Ile Ile Asn Thr
            35                  40                  45

Pro Gln Cys Ser Thr Ile Pro Glu Val Ala Val Glu Pro Glu Val Gln
    50                  55                  60

Pro Ile Pro Asp Thr Pro Leu Thr Ala Ile Phe Ile Ile Arg Ala Leu
65                  70                  75                  80

Val Ala Arg Lys Leu Arg Arg Ser Glu Thr Glu Ile Asp Pro Ser Arg
                85                  90                  95

Ser Ile Lys Glu Leu Cys Gly Gly Lys Ser Thr Leu Gln Asn Glu Leu
            100                 105                 110

Ile Gly Glu Leu Gly Asn Glu Phe Gln Thr Ser Leu Pro Asp Arg Ala
        115                 120                 125

Glu Asp Val Ser Leu Ala Asp Leu Asp Ala Ala Leu Gly Glu Val Ser
    130                 135                 140

Leu Gly Pro Thr Ser Val Ser Leu Leu Gln Arg Val Phe Thr Ala Lys
145                 150                 155                 160

Met Pro Ala Arg Met Thr Val Ser Asn Val Arg Glu Arg Leu Ala Glu
                165                 170                 175

Ile Trp Gly Leu Gly Phe His Arg Gln Thr Ala Val Leu Val Ala Ala
            180                 185                 190

Leu Ala Ala Glu Pro His Ser Arg Leu Thr Ser Leu Glu Ala Ala Tyr
        195                 200                 205

Gln Tyr Trp Asp Gly Leu Asn Glu Ala Tyr Gly Gln Ser Leu Gly Leu
    210                 215                 220

Phe Leu Arg Lys Ala Ile Ser Gln Gln Ala Ala Arg Ser Asp Asp Gln
225                 230                 235                 240

Gly Ala Gln Ala Ile Ala Pro Asp Ser Leu Gly Ser Lys Asp Leu
                245                 250                 255

Ala Arg Lys Gln Tyr Glu Ala Leu Arg Glu Tyr Leu Gly Ile Arg Thr
            260                 265                 270

Pro Thr Thr Lys Gln Asp Gly Leu Asp Leu Ala Asp Leu Gln Gln Lys
        275                 280                 285

Leu Asp Cys Trp Thr Ala Glu Phe Ser Asp Phe Leu Ser Gln Ile
    290                 295                 300

Ser Arg Arg Phe Asp Ala Arg Lys Thr Arg Trp Tyr Arg Asp Trp Trp
```

```
            305                 310                 315                 320
Asn Ser Ala Arg Gln Glu Leu Leu Thr Ile Cys Gln Asn Ser Asn Val
                325                 330                 335

Gln Trp Thr Asp Lys Met Arg Glu His Phe Val Gln Arg Ala Glu Glu
                340                 345                 350

Gly Leu Val Glu Ile Ala Arg Ala His Ser Leu Ala Lys Pro Leu Val
                355                 360                 365

Pro Asp Leu Ile Gln Ala Ile Ser Leu Pro Pro Val Val Arg Leu Gly
                370                 375                 380

Arg Leu Ala Thr Met Met Pro Arg Thr Val Val Thr Leu Lys Gly Glu
385                 390                 395                 400

Ile Gln Cys Glu Glu His Glu Arg Glu Pro Ser Cys Phe Val Glu Phe
                405                 410                 415

Phe Ser Ser Trp Ile Gln Ala Asn Asn Ile Arg Cys Thr Ile Gln Ser
                420                 425                 430

Asn Gly Glu Asp Leu Thr Ser Val Phe Ile Asn Ser Leu Val His Ala
                435                 440                 445

Ser Gln Gln Gly Val Ser Phe Pro Asn His Thr Tyr Leu Ile Thr Gly
                450                 455                 460

Ala Gly Pro Gly Ser Ile Gly Gln His Ile Val Arg Arg Leu Leu Thr
465                 470                 475                 480

Gly Gly Ala Arg Val Ile Val Thr Thr Ser Arg Glu Pro Leu Pro Ala
                485                 490                 495

Ala Ala Phe Phe Lys Glu Leu Tyr Ser Lys Cys Gly Asn Arg Gly Ser
                500                 505                 510

Gln Leu His Leu Val Pro Phe Asn Gln Ala Ser Val Val Asp Cys Glu
                515                 520                 525

Arg Leu Ile Gly Tyr Ile Tyr Asp Asp Leu Gly Leu Asp Leu Asp Ala
                530                 535                 540

Ile Leu Pro Phe Ala Ala Thr Ser Gln Val Gly Ala Glu Ile Asp Gly
545                 550                 555                 560

Leu Asp Ala Ser Asn Glu Ala Ala Phe Arg Leu Met Leu Val Asn Val
                565                 570                 575

Leu Arg Leu Val Gly Phe Val Val Ser Gln Lys Arg Arg Gly Ile
                580                 585                 590

Ser Cys Arg Pro Thr Gln Val Val Leu Pro Leu Ser Pro Asn His Gly
                595                 600                 605

Ile Leu Gly Gly Asp Gly Leu Tyr Ala Glu Ser Lys Arg Gly Leu Glu
                610                 615                 620

Thr Leu Ile Gln Arg Phe His Ser Glu Ser Trp Lys Glu Leu Ser
625                 630                 635                 640

Ile Cys Gly Val Ser Ile Gly Trp Thr Arg Ser Thr Gly Leu Met Ala
                645                 650                 655

Ala Asn Asp Leu Val Ala Glu Thr Ala Glu Lys Gln Gly Arg Val Leu
                660                 665                 670

Thr Phe Ser Val Asp Glu Met Gly Asp Leu Ile Ser Leu Leu Leu Thr
                675                 680                 685

Pro Gln Leu Ala Thr Arg Cys Glu Asp Ala Pro Val Met Ala Asp Phe
                690                 695                 700

Ser Gly Asn Leu Ser Cys Trp Arg Asp Ala Ser Ala Gln Leu Ala Ala
705                 710                 715                 720

Ala Arg Ala Ser Leu Arg Glu Arg Ala Asp Thr Ala Arg Ala Leu Ala
                725                 730                 735
```

```
Gln Glu Asp Glu Arg Glu Tyr Arg Cys Arg Arg Ala Gly Ser Thr Gln
            740                 745                 750

Glu Pro Val Asp Gln Arg Val Ser Leu His Leu Gly Phe Pro Ser Leu
            755                 760                 765

Pro Glu Tyr Asp Pro Leu Leu His Pro Asp Leu Val Pro Ala Asp Ala
            770                 775                 780

Val Val Val Val Gly Phe Ala Glu Leu Gly Pro Trp Gly Ser Ala Arg
785                 790                 795                 800

Ile Arg Trp Glu Met Glu Ser Arg Gly Cys Leu Ser Pro Ala Gly Tyr
                805                 810                 815

Val Glu Thr Ala Trp Leu Met Asn Leu Ile Arg His Val Asp Asn Val
                820                 825                 830

Asn Tyr Val Gly Trp Val Asp Gly Glu Asp Gly Lys Pro Val Ala Asp
                835                 840                 845

Ala Asp Ile Pro Lys Arg Tyr Gly Glu Arg Ile Leu Ser Asn Ala Gly
                850                 855                 860

Ile Arg Ser Leu Pro Ser Asp Asn Arg Glu Val Phe Gln Glu Ile Val
865                 870                 875                 880

Leu Glu Gln Asp Leu Pro Ser Phe Glu Thr Thr Arg Glu Asn Ala Glu
                885                 890                 895

Ala Leu Gln Gln Arg His Gly Asp Met Val Gln Val Ser Thr Leu Lys
                900                 905                 910

Asn Gly Leu Cys Leu Val Gln Leu Gln His Gly Ala Thr Ile Arg Val
                915                 920                 925

Pro Lys Ser Ile Met Ser Pro Gly Val Ala Gly Gln Leu Pro Thr
                930                 935                 940

Gly Trp Ser Pro Glu Arg Tyr Gly Ile Pro Ala Glu Ile Val Gln Gln
945                 950                 955                 960

Val Asp Pro Val Ala Leu Val Leu Cys Cys Val Ala Glu Ala Phe
                965                 970                 975

Tyr Ser Ala Gly Ile Ser Asp Pro Met Glu Ile Phe Glu His Ile His
                980                 985                 990

Leu Ser Glu Leu Gly Asn Phe Val Gly Ser Ser Met Gly Gly Val Val
                995                 1000                1005

Asn Thr Arg Ala Leu Tyr His Asp Val Cys Leu Asp Lys Asp Val
            1010                1015                1020

Gln Ser Asp Ala Leu Gln Glu Thr Tyr Leu Asn Thr Ala Pro Ala
            1025                1030                1035

Trp Val Asn Met Leu Tyr Leu Gly Ala Ala Gly Pro Ile Lys Thr
            1040                1045                1050

Pro Val Gly Ala Cys Ala Thr Ala Leu Glu Ser Val Asp Ser Ala
            1055                1060                1065

Val Glu Ser Ile Lys Ala Gly Gln Thr Lys Ile Cys Leu Val Gly
            1070                1075                1080

Gly Tyr Asp Asp Leu Gln Pro Glu Glu Ser Ala Gly Phe Ala Arg
            1085                1090                1095

Met Lys Ala Thr Val Ser Val Arg Asp Glu Gln Ala Arg Gly Arg
            1100                1105                1110

Glu Pro Gly Glu Met Ser Arg Pro Thr Ala Ala Ser Arg Ser Gly
            1115                1120                1125

Phe Val Glu Ser Gln Gly Cys Gly Val Gln Leu Leu Cys Arg Gly
            1130                1135                1140
```

-continued

```
Asp Val Ala Leu Ala Met Gly Leu Pro Ile Tyr Gly Ile Ile Ala
1145                1150                1155

Gly Thr Gly Met Ala Ser Asp Gly Ile Gly Arg Ser Val Pro Ala
1160                1165                1170

Pro Gly Gln Gly Ile Leu Thr Phe Ala Gln Glu Asp Ala Gln Asn
1175                1180                1185

Pro Ala Pro Ser Arg Thr Ala Leu Ala Arg Trp Gly Leu Gly Ile
1190                1195                1200

Asp Asp Ile Thr Val Ala Ser Leu His Ala Thr Ser Thr Pro Ala
1205                1210                1215

Asn Asp Thr Asn Glu Pro Leu Val Ile Gln Arg Glu Met Thr His
1220                1225                1230

Leu Gly Arg Thr Ser Gly Arg Pro Leu Trp Ala Ile Cys Gln Lys
1235                1240                1245

Phe Val Thr Gly His Pro Lys Ala Pro Ala Ala Ala Trp Met Leu
1250                1255                1260

Asn Gly Cys Leu Gln Val Leu Asp Thr Gly Leu Val Pro Gly Asn
1265                1270                1275

Arg Asn Ala Asp Asp Val Asp Pro Ala Leu Arg Ser Phe Ser His
1280                1285                1290

Leu Cys Phe Pro Ile Arg Ser Ile Gln Thr Asp Gly Ile Lys Ala
1295                1300                1305

Phe Leu Leu Asn Ser Cys Gly Phe Gly Gln Lys Glu Ala Gln Leu
1310                1315                1320

Val Gly Val His Pro Arg Tyr Phe Leu Gly Leu Leu Ser Glu Pro
1325                1330                1335

Glu Phe Glu Glu Tyr Arg Thr Arg Arg Gln Leu Arg Ile Ala Gly
1340                1345                1350

Ala Glu Arg Ala Tyr Ile Ser Ala Met Met Thr Asn Ser Ile Val
1355                1360                1365

Cys Val Gln Ser His Pro Pro Phe Gly Pro Ala Glu Met His Ser
1370                1375                1380

Ile Leu Leu Asp Pro Ser Ala Arg Ile Cys Leu Asp Ser Ser Thr
1385                1390                1395

Asn Ser Tyr Arg Val Thr Lys Ala Ser Thr Pro Val Tyr Thr Gly
1400                1405                1410

Phe Gln Arg Pro His Asp Lys Arg Glu Asp Pro Arg Pro Ser Thr
1415                1420                1425

Ile Gly Val Asp Thr Val Thr Leu Ser Ser Phe Asn Ala His Glu
1430                1435                1440

Asn Ala Ile Phe Leu Gln Arg Asn Tyr Thr Glu Arg Glu Arg Gln
1445                1450                1455

Ser Leu Gln Leu Gln Ser His Arg Ser Phe Arg Ser Ala Val Ala
1460                1465                1470

Ser Gly Trp Cys Ala Lys Glu Ala Val Phe Lys Cys Leu Gln Thr
1475                1480                1485

Val Ser Lys Gly Ala Gly Ala Ala Met Ser Glu Ile Glu Ile Val
1490                1495                1500

Arg Val Gln Gly Ala Pro Ser Val Leu His Gly Asp Ala Leu Ala
1505                1510                1515

Ala Ala Gln Lys Ala Gly Leu Asp Asn Ile Gln Leu Ser Leu Ser
1520                1525                1530

Tyr Gly Asp Asp Cys Val Val Ala Val Ala Leu Gly Val Arg Lys
```

-continued

```
            1535                1540                1545

Trp Cys Leu Trp Pro Leu Ala Ser Ile Ile Arg
        1550                1555

<210> SEQ ID NO 19
<211> LENGTH: 1914
<212> TYPE: PRT
<213> ORGANISM: Aspergillus nidulans

<400> SEQUENCE: 19

Met Thr Pro Ser Pro Phe Leu Asp Ala Val Asp Ala Gly Leu Ser Arg
1               5                   10                  15

Leu Tyr Ala Cys Phe Gly Gly Gln Gly Pro Ser Asn Trp Ala Gly Leu
            20                  25                  30

Asp Glu Leu Val His Leu Ser His Ala Tyr Ala Asp Cys Ala Pro Ile
        35                  40                  45

Gln Asp Leu Leu Asp Ser Ser Ala Arg Arg Leu Glu Ser Gln Gln Arg
    50                  55                  60

Ser His Thr Asp Arg His Phe Leu Leu Gly Ala Gly Ser Asn Tyr Arg
65                  70                  75                  80

Pro Gly Ser Thr Thr Leu Leu His Pro His His Leu Pro Glu Asp Leu
                85                  90                  95

Ala Leu Ser Pro Tyr Ser Phe Pro Ile Asn Thr Leu Ser Leu Leu
            100                 105                 110

His Tyr Ala Ile Thr Ala Tyr Ser Leu Gln Leu Asp Pro Gly Gln Leu
        115                 120                 125

Arg Gln Lys Leu Gln Gly Ala Ile Gly His Ser Gln Gly Val Phe Val
    130                 135                 140

Ala Ala Ala Ile Ala Ile Ser His Thr Asp His Gly Trp Pro Ser Phe
145                 150                 155                 160

Tyr Arg Ala Ala Asp Leu Ala Leu Gln Leu Ser Phe Trp Val Gly Leu
                165                 170                 175

Glu Ser His His Ala Ser Pro Arg Ser Ile Leu Cys Ala Asn Glu Val
            180                 185                 190

Ile Asp Cys Leu Glu Asn Gly Glu Gly Ala Pro Ser His Leu Leu Ser
        195                 200                 205

Val Thr Gly Leu Asp Ile Asn His Leu Glu Arg Leu Val Arg Lys Leu
    210                 215                 220

Asn Asp Gln Gly Gly Asp Ser Leu Tyr Ile Ser Leu Ile Asn Gly His
225                 230                 235                 240

Asn Lys Phe Val Leu Ala Gly Ala Pro His Ala Leu Arg Gly Val Cys
                245                 250                 255

Ile Ala Leu Arg Ser Val Lys Ala Ser Pro Glu Leu Asp Gln Ser Arg
            260                 265                 270

Val Pro Phe Pro Leu Arg Arg Ser Val Val Asp Val Gln Phe Leu Pro
        275                 280                 285

Val Ser Ala Pro Tyr His Ser Ser Leu Leu Ser Ser Val Glu Leu Arg
    290                 295                 300

Val Thr Asp Ala Ile Gly Gly Leu Arg Leu Arg Gly Asn Asp Leu Ala
305                 310                 315                 320

Ile Pro Val Tyr Cys Gln Ala Asn Gly Ser Leu Arg Asn Leu Gln Asp
                325                 330                 335

Tyr Gly Thr His Asp Ile Leu Leu Thr Leu Ile Gln Ser Val Thr Val
            340                 345                 350
```

```
Glu Arg Val Asn Trp Pro Ala Leu Cys Trp Ala Met Asn Asp Ala Thr
            355                 360                 365
His Val Leu Ser Phe Gly Pro Ala Val Gly Ser Leu Val Gln Asp
    370                 375                 380
Val Leu Glu Gly Thr Gly Met Asn Val Val Asn Leu Ser Gly Gln Ser
385                 390                 395                 400
Met Ala Ser Asn Leu Ser Leu Asn Leu Ser Ala Phe Ala Leu Pro
                405                 410                 415
Leu Gly Lys Asp Trp Gly Arg Lys Tyr Arg Pro Arg Leu Arg Lys Ala
            420                 425                 430
Ala Glu Gly Ser Ala His Ala Ser Ile Glu Thr Lys Met Thr Arg Leu
                435                 440                 445
Leu Gly Thr Pro His Val Met Val Ala Gly Met Thr Pro Thr Thr Cys
        450                 455                 460
Ser Pro Glu Leu Val Ala Ala Ile Ile Gln Ala Asp Tyr His Val Glu
465                 470                 475                 480
Phe Ala Cys Gly Gly Tyr Tyr Asn Arg Ala Thr Leu Glu Thr Ala Leu
                485                 490                 495
Arg Gln Leu Ser Arg Ser Ile Pro Pro His Arg Ser Ile Thr Cys Asn
            500                 505                 510
Val Ile Tyr Ala Ser Pro Lys Ala Leu Ser Trp Gln Thr Gln Val Leu
    515                 520                 525
Arg Arg Leu Ile Met Glu Glu Gly Leu Pro Ile Asp Gly Ile Thr Val
530                 535                 540
Gly Ala Gly Ile Pro Ser Pro Glu Val Val Lys Glu Trp Ile Asp Met
545                 550                 555                 560
Leu Ala Ile Ser His Ile Trp Phe Lys Pro Gly Ser Val Asp Ala Ile
                565                 570                 575
Asp Arg Val Leu Thr Ile Ala Arg Gln Tyr Pro Thr Leu Pro Val Gly
            580                 585                 590
Ile Gln Trp Thr Gly Gly Arg Ala Gly Gly His His Ser Cys Glu Asp
        595                 600                 605
Phe His Leu Pro Ile Leu Asp Cys Tyr Ala Arg Ile Arg Asn Cys Glu
    610                 615                 620
Asn Val Ile Leu Val Ala Gly Ser Gly Phe Gly Gly Ala Glu Asp Thr
625                 630                 635                 640
Trp Pro Tyr Met Asn Gly Ser Trp Ser Cys Lys Leu Gly Tyr Ala Pro
                645                 650                 655
Met Pro Phe Asp Gly Ile Leu Leu Gly Ser Arg Met Met Val Ala Arg
            660                 665                 670
Glu Ala Lys Thr Ser Phe Ala Val Lys Gln Leu Ile Val Glu Ala Pro
        675                 680                 685
Gly Val Lys Asp Asp Gly Asn Asp Asn Gly Ala Trp Ala Lys Cys Glu
    690                 695                 700
His Asp Ala Val Gly Gly Val Ile Ser Val Thr Ser Glu Met Gly Gln
705                 710                 715                 720
Pro Ile His Val Leu Ala Thr Arg Ala Met Arg Leu Trp Lys Glu Phe
                725                 730                 735
Asp Asp Arg Phe Phe Ser Ile Arg Asp Pro Lys Arg Leu Lys Ala Ala
            740                 745                 750
Leu Lys Gln His Arg Val Glu Ile Ile Asn Arg Leu Asn Asn Asp Phe
        755                 760                 765
Ala Arg Pro Trp Phe Ala Gln Thr Asp Ser Ser Lys Pro Thr Glu Ile
```

```
                  770                 775                 780
Glu Glu Leu Ser Tyr Arg Gln Val Leu Arg Arg Leu Cys Gln Leu Thr
785                 790                 795                 800

Tyr Val Gln His Gln Ala Arg Trp Ile Asp Ser Ser Tyr Leu Ser Leu
                805                 810                 815

Val His Asp Phe Leu Arg Leu Ala Gln Gly Arg Leu Gly Ser Gly Ser
                820                 825                 830

Glu Ala Glu Leu Arg Phe Leu Ser Cys Asn Thr Pro Ile Glu Leu Glu
            835                 840                 845

Ala Ser Phe Asp Ala Ala Tyr Gly Val Gln Gly Asp Gln Ile Leu Tyr
        850                 855                 860

Pro Glu Asp Val Ser Leu Leu Ile Asn Leu Phe Arg Arg Gln Gly Gln
865                 870                 875                 880

Lys Pro Val Pro Phe Ile Pro Arg Leu Asp Ala Asp Phe Gln Thr Trp
                885                 890                 895

Phe Lys Lys Asp Ser Leu Trp Gln Ser Glu Asp Val Asp Ala Val Val
                900                 905                 910

Asp Gln Asp Ala Gln Arg Val Cys Ile Ile Gln Gly Pro Val Ala Val
            915                 920                 925

Arg His Ser Arg Val Cys Asp Glu Pro Val Lys Asp Ile Leu Asp Gly
        930                 935                 940

Ile Thr Glu Ala His Leu Lys Met Met Leu Lys Glu Ala Ala Ser Asp
945                 950                 955                 960

Asn Gly Tyr Thr Trp Ala Asn Gln Arg Asp Glu Lys Gly Asn Arg Leu
                965                 970                 975

Pro Gly Ile Glu Thr Ser Gln Glu Gly Ser Leu Cys Arg Tyr Tyr Leu
            980                 985                 990

Val Gly Pro Thr Leu Pro Ser Thr  Glu Ala Ile Val Glu  His Leu Val
        995                 1000                1005

Gly Glu  Cys Ala Trp Gly Tyr  Ala Ala Leu Ser Gln  Lys Lys Val
    1010                1015                1020

Val Phe  Gly Gln Asn Arg Ala  Pro Asn Pro Ile Arg  Asp Ala Phe
    1025                1030                1035

Lys Pro  Asp Ile Gly Asp Val  Ile Glu Ala Lys Tyr  Met Asp Gly
    1040                1045                1050

Cys Leu  Arg Glu Ile Thr Leu  Tyr His Ser Leu Arg  Arg Gln Gly
    1055                1060                1065

Asp Pro  Arg Ala Ile Arg Ala  Ala Leu Gly Leu Ile  His Leu Asp
    1070                1075                1080

Gly Asn  Lys Val Ser Val Thr  Leu Leu Thr Arg Ser  Lys Gly Lys
    1085                1090                1095

Arg Pro  Ala Leu Glu Phe Lys  Met Glu Leu Leu Gly  Gly Thr Met
    1100                1105                1110

Gly Pro  Leu Ile Leu Lys Met  His Arg Thr Asp Tyr  Leu Asp Ser
    1115                1120                1125

Val Arg  Arg Leu Tyr Thr Asp  Leu Trp Ile Gly Arg  Asp Leu Pro
    1130                1135                1140

Ser Pro  Thr Ser Val Gly Leu  Asn Ser Glu Phe Thr  Gly Asp Arg
    1145                1150                1155

Val Thr  Ile Thr Ala Glu Asp  Val Asn Thr Phe Leu  Ala Ile Val
    1160                1165                1170

Gly Gln  Ala Gly Pro Ala Arg  Cys Arg Ala Trp Gly  Thr Arg Gly
    1175                1180                1185
```

```
Pro Val Val Pro Ile Asp Tyr Ala Val Ile Ala Trp Thr Ala
    1190            1195            1200

Leu Thr Lys Pro Ile Leu Leu Glu Ala Leu Asp Ala Asp Pro Leu
    1205            1210            1215

Arg Leu Leu His Gln Ser Ala Ser Thr Arg Phe Val Pro Gly Ile
    1220            1225            1230

Arg Pro Leu His Val Gly Asp Thr Val Thr Thr Ser Ser Arg Ile
    1235            1240            1245

Thr Glu Arg Thr Ile Thr Thr Ile Gly Gln Arg Val Glu Ile Ser
    1250            1255            1260

Ala Glu Leu Leu Arg Glu Gly Lys Pro Val Val Arg Leu Gln Thr
    1265            1270            1275

Thr Phe Ile Ile Gln Arg Arg Pro Glu Glu Ser Val Ser Gln Gln
    1280            1285            1290

Gln Phe Arg Cys Val Glu Glu Pro Asp Met Val Ile Arg Val Asp
    1295            1300            1305

Ser His Thr Lys Leu Arg Val Leu Met Ser Arg Lys Trp Phe Leu
    1310            1315            1320

Leu Asp Gly Pro Cys Ser Asp Leu Ile Gly Lys Ile Leu Ile Phe
    1325            1330            1335

Gln Leu His Ser Gln Thr Val Phe Asp Ala Ala Gly Ala Pro Ala
    1340            1345            1350

Ser Leu Gln Val Ser Gly Ser Val Ser Leu Ala Pro Ser Asp Thr
    1355            1360            1365

Ser Val Val Cys Val Ser Ser Val Gly Thr Arg Ile Gly Arg Val
    1370            1375            1380

Tyr Met Glu Glu Gly Phe Gly Ala Asn Pro Val Met Asp Phe
    1385            1390            1395

Leu Asn Arg His Gly Ala Pro Arg Val Gln Arg Gln Pro Leu Pro
    1400            1405            1410

Arg Ala Gly Trp Thr Gly Asp Asp Ala Ala Ser Ile Ser Phe Thr
    1415            1420            1425

Ala Pro Ala Gln Ser Glu Gly Tyr Ala Met Val Ser Gly Asp Thr
    1430            1435            1440

Asn Pro Ile His Val Cys Pro Leu Phe Ser Arg Phe Ala Gly Leu
    1445            1450            1455

Gly Gln Pro Val Val His Gly Leu His Leu Ser Ala Thr Val Arg
    1460            1465            1470

Arg Ile Leu Glu Trp Ile Ile Gly Asp Asn Glu Arg Thr Arg Phe
    1475            1480            1485

Cys Ser Trp Ala Pro Ser Phe Asp Gly Leu Val Arg Ala Asn Asp
    1490            1495            1500

Arg Leu Arg Met Glu Ile Gln His Phe Ala Met Ala Asp Gly Cys
    1505            1510            1515

Met Val Val His Val Arg Val Leu Lys Glu Ser Thr Gly Glu Gln
    1520            1525            1530

Val Met His Ala Glu Ala Val Leu Glu Gln Ala Gln Thr Thr Tyr
    1535            1540            1545

Val Phe Thr Gly Gln Gly Thr Gln Glu Arg Gly Met Gly Met Ala
    1550            1555            1560

Leu Tyr Asp Thr Asn Ala Ala Ala Arg Ala Val Trp Asp Arg Ala
    1565            1570            1575
```

| | | | | | | | | | | | | |
|---|---|---|---|---|---|---|---|---|---|---|---|---|
| Glu | Arg 1580 | His | Phe | Arg | Ser 1585 | Gln | Tyr | Gly | Ile | Ser 1590 | Leu | Leu His Ile |

Val Arg Glu Asn Pro Thr Ser Leu Thr Val Asn Phe Gly Ser Arg
　　1595　　　　　　　　　1600　　　　　　　　　1605

Arg Gly Arg Gln Ile Arg Asp Ile Tyr Leu Ser Met Ser Asp Ser
　　1610　　　　　　　　　1615　　　　　　　　　1620

Asp Pro Ser Met Leu Pro Gly Leu Thr Arg Asp Ser Arg Ser Tyr
　　1625　　　　　　　　　1630　　　　　　　　　1635

Thr Phe Asn Tyr Pro Ser Gly Leu Leu Met Ser Thr Gln Phe Ala
　　1640　　　　　　　　　1645　　　　　　　　　1650

Gln Pro Ala Leu Ala Val Met Glu Ile Ala Glu Tyr Ala His Leu
　　1655　　　　　　　　　1660　　　　　　　　　1665

Gln Ala Gln Gly Val Val Gln Thr Gln Ala Ile Phe Ala Gly His
　　1670　　　　　　　　　1675　　　　　　　　　1680

Ser Leu Gly Glu Tyr Ser Ser Leu Gly Ala Cys Thr Thr Ile Met
　　1685　　　　　　　　　1690　　　　　　　　　1695

Pro Phe Glu Ser Leu Leu Ser Leu Ile Leu Tyr Arg Gly Leu Lys
　　1700　　　　　　　　　1705　　　　　　　　　1710

Met Gln Asn Thr Leu Pro Arg Asn Ala Asn Gly Arg Thr Asp Tyr
　　1715　　　　　　　　　1720　　　　　　　　　1725

Gly Met Val Ala Ala Asp Pro Ser Arg Ile Arg Ser Asp Phe Thr
　　1730　　　　　　　　　1735　　　　　　　　　1740

Glu Asp Arg Leu Ile Glu Leu Val Arg Leu Val Ser Gln Ala Thr
　　1745　　　　　　　　　1750　　　　　　　　　1755

Gly Val Leu Leu Glu Val Val Asn Tyr Asn Val His Ser Arg Gln
　　1760　　　　　　　　　1765　　　　　　　　　1770

Tyr Val Cys Ala Gly His Val Arg Ser Leu Trp Val Leu Ser His
　　1775　　　　　　　　　1780　　　　　　　　　1785

Ala Cys Asp Asp Leu Ser Arg Ser Thr Ser Pro Asn Ser Pro Gln
　　1790　　　　　　　　　1795　　　　　　　　　1800

Thr Met Ser Glu Cys Ile Ala His His Ile Pro Ser Ser Cys Ser
　　1805　　　　　　　　　1810　　　　　　　　　1815

Val Thr Asn Glu Thr Glu Leu Ser Arg Gly Arg Ala Thr Ile Pro
　　1820　　　　　　　　　1825　　　　　　　　　1830

Leu Ala Gly Val Asp Ile Pro Phe His Ser Gln Met Leu Arg Gly
　　1835　　　　　　　　　1840　　　　　　　　　1845

His Ile Asp Gly Tyr Arg Gln Tyr Leu Arg His His Leu Arg Val
　　1850　　　　　　　　　1855　　　　　　　　　1860

Ser Asp Ile Lys Pro Glu Glu Leu Val Gly Arg Trp Ile Pro Asn
　　1865　　　　　　　　　1870　　　　　　　　　1875

Val Thr Gly Lys Pro Phe Ala Leu Asp Ala Pro Tyr Ile Arg Leu
　　1880　　　　　　　　　1885　　　　　　　　　1890

Val Gln Gly Val Thr Gln Ser Arg Pro Leu Leu Glu Leu Leu Arg
　　1895　　　　　　　　　1900　　　　　　　　　1905

Arg Val Glu Glu Asn Arg
　　1910

<210> SEQ ID NO 20
<211> LENGTH: 1858
<212> TYPE: PRT
<213> ORGANISM: Yarrowia lipolytica

<400> SEQUENCE: 20

Met Arg Pro Glu Ile Glu Gln Glu Leu Ala His Thr Leu Leu Val Glu
1　　　　　　　5　　　　　　　　　10　　　　　　　　　15

```
Leu Leu Ala Tyr Gln Phe Ala Ser Pro Val Arg Trp Ile Glu Thr Gln
         20                  25                  30

Asp Val Ile Leu Ala Glu Lys Arg Thr Glu Arg Ile Val Glu Ile Gly
             35                  40                  45

Pro Ala Asp Thr Leu Gly Gly Met Ala Arg Arg Thr Leu Ala Ser Lys
         50                  55                  60

Tyr Glu Ala Tyr Asp Ala Ala Thr Ser Val Gln Arg Gln Ile Leu Cys
65                  70                  75                  80

Tyr Asn Lys Asp Ala Lys Glu Ile Tyr Tyr Asp Val Asp Pro Val Glu
                 85                  90                  95

Glu Glu Thr Glu Ser Ala Pro Glu Ala Ala Ala Pro Pro Thr Ser
             100                 105                 110

Ala Ala Pro Ala Ala Val Val Ala Ala Pro Ala Pro Ala Ala Ser
             115                 120                 125

Ala Pro Ser Ala Gly Pro Ala Ala Pro Val Glu Asp Ala Pro Val Thr
130                 135                 140

Ala Leu Asp Ile Val Arg Thr Leu Val Ala Gln Lys Leu Lys Lys Ala
145                 150                 155                 160

Leu Ser Asp Val Pro Leu Asn Lys Ala Ile Lys Asp Leu Val Gly Gly
                 165                 170                 175

Lys Ser Thr Leu Gln Asn Glu Ile Leu Gly Asp Leu Gly Lys Glu Phe
             180                 185                 190

Gly Ser Thr Pro Glu Lys Pro Glu Asp Thr Pro Leu Asp Glu Leu Gly
         195                 200                 205

Ala Ser Met Gln Ala Thr Phe Asn Gly Gln Leu Gly Lys Gln Ser Ser
         210                 215                 220

Ser Leu Ile Ala Arg Leu Val Ser Ser Lys Met Pro Gly Gly Phe Asn
225                 230                 235                 240

Ile Thr Ala Val Arg Lys Tyr Leu Glu Thr Arg Trp Gly Leu Gly Pro
                 245                 250                 255

Gly Arg Gln Asp Gly Val Leu Leu Leu Ala Leu Thr Met Glu Pro Ala
             260                 265                 270

Ser Arg Ile Gly Ser Glu Pro Asp Ala Lys Val Phe Leu Asp Asp Val
         275                 280                 285

Ala Asn Lys Tyr Ala Ala Asn Ser Gly Ile Ser Leu Asn Val Pro Thr
         290                 295                 300

Ala Ser Gly Asp Gly Gly Ala Ser Ala Gly Gly Met Leu Met Asp Pro
305                 310                 315                 320

Ala Ala Ile Asp Ala Leu Thr Lys Asp Gln Arg Ala Leu Phe Lys Gln
                 325                 330                 335

Gln Leu Glu Ile Ile Ala Arg Tyr Leu Lys Met Asp Leu Arg Asp Gly
             340                 345                 350

Gln Lys Ala Phe Val Ala Ser Gln Glu Thr Gln Lys Thr Leu Gln Ala
         355                 360                 365

Gln Leu Asp Leu Trp Gln Ala Glu His Gly Asp Phe Tyr Ala Ser Gly
         370                 375                 380

Ile Glu Pro Ser Phe Asp Pro Leu Lys Ala Arg Val Tyr Asp Ser Ser
385                 390                 395                 400

Trp Asn Trp Ala Arg Gln Asp Ala Leu Ser Met Tyr Tyr Asp Ile Ile
                 405                 410                 415

Phe Gly Arg Leu Lys Val Val Asp Arg Glu Ile Val Ser Gln Cys Ile
             420                 425                 430
```

```
Arg Ile Met Asn Arg Ser Asn Pro Leu Leu Glu Phe Met Gln Tyr
            435                 440                 445
His Ile Asp Asn Cys Pro Thr Glu Arg Gly Glu Thr Tyr Gln Leu Ala
    450                 455                 460
Lys Glu Leu Gly Glu Gln Leu Ile Glu Asn Cys Lys Glu Val Leu Gly
465                 470                 475                 480
Val Ser Pro Val Tyr Lys Asp Val Ala Val Pro Thr Gly Pro Gln Thr
                485                 490                 495
Thr Ile Asp Ala Arg Gly Asn Ile Glu Tyr Gln Glu Val Pro Arg Ala
            500                 505                 510
Ser Ala Arg Lys Leu Glu His Tyr Val Lys Gln Met Ala Glu Gly Gly
        515                 520                 525
Pro Ile Ser Glu Tyr Ser Asn Arg Ala Lys Val Gln Asn Asp Leu Arg
        530                 535                 540
Ser Val Tyr Lys Leu Ile Arg Arg Gln His Arg Leu Ser Lys Ser Ser
545                 550                 555                 560
Gln Leu Gln Phe Asn Ala Leu Tyr Lys Asp Val Val Arg Ala Leu Ser
                565                 570                 575
Met Asn Glu Asn Gln Ile Met Pro Gln Glu Asn Gly Ser Thr Lys Lys
            580                 585                 590
Pro Gly Arg Asn Gly Ser Val Arg Asn Gly Ser Pro Arg Ala Gly Lys
        595                 600                 605
Val Glu Thr Ile Pro Phe Leu His Leu Lys Lys Asn Glu His Gly
        610                 615                 620
Trp Asp Tyr Ser Lys Lys Leu Thr Gly Ile Tyr Leu Asp Val Leu Glu
625                 630                 635                 640
Ser Ala Ala Arg Ser Gly Leu Thr Phe Gln Gly Lys Asn Val Leu Met
                645                 650                 655
Thr Gly Ala Gly Ala Gly Ser Ile Gly Ala Glu Val Leu Gln Gly Leu
            660                 665                 670
Ile Ser Gly Gly Ala Lys Val Ile Val Thr Thr Ser Arg Tyr Ser Arg
        675                 680                 685
Glu Val Thr Glu Tyr Tyr Gln Ala Met Tyr Ala Arg Tyr Gly Ala Arg
        690                 695                 700
Gly Ser Gln Leu Val Val Pro Phe Asn Gln Gly Ser Lys Gln Asp
705                 710                 715                 720
Val Glu Ala Leu Val Asp Tyr Ile Tyr Asp Thr Lys Lys Gly Leu Gly
                725                 730                 735
Trp Asp Leu Asp Phe Ile Val Pro Phe Ala Ala Ile Pro Glu Asn Gly
            740                 745                 750
Arg Glu Ile Asp Ser Ile Asp Ser Lys Ser Glu Leu Ala His Arg Ile
        755                 760                 765
Met Leu Thr Asn Leu Leu Arg Leu Leu Gly Ser Val Lys Ala Gln Lys
        770                 775                 780
Gln Ala Asn Gly Phe Glu Thr Arg Pro Ala Gln Val Ile Leu Pro Leu
785                 790                 795                 800
Ser Pro Asn His Gly Thr Phe Gly Asn Asp Gly Leu Tyr Ser Glu Ser
                805                 810                 815
Lys Leu Ala Leu Glu Thr Leu Phe Asn Arg Trp Tyr Ser Glu Asn Trp
            820                 825                 830
Ser Asn Tyr Leu Thr Ile Cys Gly Ala Val Ile Gly Trp Thr Arg Gly
        835                 840                 845
Thr Gly Leu Met Ser Gly Asn Asn Met Val Ala Glu Gly Val Glu Lys
```

-continued

```
            850                 855                 860
Leu Gly Val Arg Thr Phe Ser Gln Gln Glu Met Ala Phe Asn Leu Leu
865                 870                 875                 880

Gly Leu Met Ala Pro Ala Ile Val Asn Leu Cys Gln Leu Asp Pro Val
                    885                 890                 895

Trp Ala Asp Leu Asn Gly Gly Leu Gln Phe Ile Pro Asp Leu Lys Asp
                900                 905                 910

Leu Met Thr Arg Leu Arg Thr Glu Ile Met Glu Thr Ser Asp Val Arg
                915                 920                 925

Arg Ala Val Ile Lys Glu Thr Ala Ile Glu Asn Lys Val Val Asn Gly
            930                 935                 940

Glu Asp Ser Glu Val Leu Tyr Lys Lys Val Ile Ala Glu Pro Arg Ala
945                 950                 955                 960

Asn Ile Lys Phe Gln Phe Pro Asn Leu Pro Trp Asp Glu Asp Ile
                965                 970                 975

Lys Pro Leu Asn Glu Asn Leu Lys Gly Met Val Asn Leu Asp Lys Val
                980                 985                 990

Val Val Val Thr Gly Phe Ser Glu Val Gly Pro Trp Gly Asn Ser Arg
                995                 1000                1005

Thr Arg Trp Glu Met Glu Ala Ser Gly Lys Phe Ser Leu Glu Gly
    1010                1015                1020

Cys Val Glu Met Ala Trp Ile Met Gly Leu Ile Arg His His Asn
    1025                1030                1035

Gly Pro Ile Lys Gly Lys Thr Tyr Ser Gly Trp Val Asp Ser Lys
    1040                1045                1050

Thr Gly Glu Pro Val Asp Asp Lys Asp Val Lys Ala Lys Tyr Glu
    1055                1060                1065

Lys Tyr Ile Leu Glu His Ser Gly Ile Arg Leu Ile Glu Pro Glu
    1070                1075                1080

Leu Phe Lys Gly Tyr Asp Pro Lys Lys Lys Gln Leu Leu Gln Glu
    1085                1090                1095

Ile Val Ile Glu Glu Asp Leu Glu Pro Phe Glu Ala Ser Lys Glu
    1100                1105                1110

Thr Ala Glu Glu Phe Lys Arg Glu His Gly Glu Lys Val Glu Ile
    1115                1120                1125

Phe Glu Val Leu Glu Ser Gly Glu Tyr Thr Val Arg Leu Lys Lys
    1130                1135                1140

Gly Ala Thr Leu Leu Ile Pro Lys Ala Leu Gln Phe Asp Arg Leu
    1145                1150                1155

Val Ala Gly Gln Val Pro Thr Gly Trp Asp Ala Arg Arg Tyr Gly
    1160                1165                1170

Ile Pro Glu Asp Ile Ile Glu Gln Val Asp Pro Val Thr Leu Phe
    1175                1180                1185

Val Leu Val Cys Thr Ala Glu Ala Met Leu Ser Ala Gly Val Thr
    1190                1195                1200

Asp Pro Tyr Glu Phe Tyr Lys Tyr Val His Leu Ser Glu Val Gly
    1205                1210                1215

Asn Cys Ile Gly Ser Gly Ile Gly Gly Thr His Ala Leu Arg Gly
    1220                1225                1230

Met Tyr Lys Asp Arg Tyr Leu Asp Lys Pro Leu Gln Lys Asp Ile
    1235                1240                1245

Leu Gln Glu Ser Phe Ile Asn Thr Met Ser Ala Trp Val Asn Met
    1250                1255                1260
```

```
Leu Leu Leu Ser Ser Thr Gly Pro Ile Lys Thr Pro Val Gly Ala
    1265            1270            1275

Cys Ala Thr Ala Val Glu Ser Val Asp Ile Gly Tyr Glu Thr Ile
    1280            1285            1290

Val Glu Gly Lys Ala Arg Val Cys Phe Val Gly Gly Phe Asp Asp
    1295            1300            1305

Phe Gln Glu Glu Gly Ser Tyr Glu Phe Ala Asn Met Lys Ala Thr
    1310            1315            1320

Ser Asn Ala Glu Asp Glu Phe Ala His Gly Arg Thr Pro Gln Glu
    1325            1330            1335

Met Ser Arg Pro Thr Thr Thr Arg Ala Gly Phe Met Glu Ser
    1340            1345            1350

Gln Gly Cys Gly Met Gln Leu Ile Met Ser Ala Gln Leu Ala Leu
    1355            1360            1365

Asp Met Gly Val Pro Ile Tyr Gly Ile Ile Ala Leu Thr Thr Thr
    1370            1375            1380

Ala Thr Asp Lys Ile Gly Arg Ser Val Pro Ala Pro Gly Gln Gly
    1385            1390            1395

Val Leu Thr Thr Ala Arg Glu Asn Pro Gly Lys Phe Pro Ser Pro
    1400            1405            1410

Leu Leu Asp Ile Lys Tyr Arg Arg Arg Gln Leu Glu Leu Arg Lys
    1415            1420            1425

Arg Gln Ile Arg Glu Trp Gln Glu Ser Glu Leu Leu Tyr Leu Gln
    1430            1435            1440

Glu Glu Ala Glu Ala Ile Lys Ala Gln Asn Pro Ala Asp Phe Val
    1445            1450            1455

Val Glu Glu Tyr Leu Gln Glu Arg Ala Gln His Ile Asn Arg Glu
    1460            1465            1470

Ala Ile Arg Gln Glu Lys Asp Ala Gln Phe Ser Leu Gly Asn Asn
    1475            1480            1485

Phe Trp Lys Gln Asp Ser Arg Ile Ala Pro Leu Arg Gly Ala Leu
    1490            1495            1500

Ala Thr Trp Gly Leu Thr Val Asp Glu Ile Gly Val Ala Ser Phe
    1505            1510            1515

His Gly Thr Ser Thr Val Ala Asn Asp Lys Asn Glu Ser Asp Val
    1520            1525            1530

Ile Cys Gln Gln Met Lys His Leu Gly Arg Lys Gly Asn Ala
    1535            1540            1545

Leu Leu Gly Ile Phe Gln Lys Tyr Leu Thr Gly His Pro Lys Gly
    1550            1555            1560

Ala Ala Gly Ala Trp Met Phe Asn Gly Cys Leu Gln Val Leu Asp
    1565            1570            1575

Ser Gly Leu Val Pro Gly Asn Arg Asn Ala Asp Asn Val Asp Lys
    1580            1585            1590

Val Met Glu Lys Phe Asp Tyr Ile Val Tyr Pro Ser Arg Ser Ile
    1595            1600            1605

Gln Thr Asp Gly Ile Lys Ala Phe Ser Val Thr Ser Phe Gly Phe
    1610            1615            1620

Gly Gln Lys Gly Ala Gln Val Ile Gly Ile His Pro Lys Tyr Leu
    1625            1630            1635

Tyr Ala Thr Leu Asp Arg Ala Gln Phe Glu Ala Tyr Arg Ala Lys
    1640            1645            1650
```

-continued

```
Val Glu Thr Arg Gln Lys Lys Ala Tyr Arg Tyr Phe His Asn Gly
    1655                1660                1665

Leu Val Asn Asn Ser Ile Phe Val Ala Lys Asn Lys Ala Pro Tyr
    1670                1675                1680

Glu Asp Glu Leu Gln Ser Lys Val Phe Leu Asn Pro Asp Tyr Arg
    1685                1690                1695

Val Ala Ala Asp Lys Lys Thr Ser Glu Leu Lys Tyr Pro Pro Lys
    1700                1705                1710

Pro Pro Val Ala Thr Asp Ala Gly Ser Glu Ser Thr Lys Ala Val
    1715                1720                1725

Ile Glu Ser Leu Ala Lys Ala His Ala Thr Glu Asn Ser Lys Ile
    1730                1735                1740

Gly Val Asp Val Glu Ser Ile Asp Ser Ile Asn Ile Ser Asn Glu
    1745                1750                1755

Thr Phe Ile Glu Arg Ile Leu Pro Ala Ser Glu Gln Gln Tyr Cys
    1760                1765                1770

Gln Asn Ala Pro Ser Pro Gln Ser Ser Phe Ala Gly Arg Trp Ser
    1775                1780                1785

Ala Lys Glu Ala Val Phe Lys Ser Leu Gly Val Cys Ser Lys Gly
    1790                1795                1800

Ala Gly Ala Pro Leu Lys Asp Ile Glu Ile Glu Asn Asp Ser Asn
    1805                1810                1815

Gly Ala Pro Thr Leu His Gly Val Ala Glu Ala Ala Lys Glu
    1820                1825                1830

Ala Gly Val Lys His Ile Ser Val Ser Ile Ser His Ser Asp Met
    1835                1840                1845

Gln Ala Val Ala Val Ala Ile Ser Gln Phe
    1850                1855

<210> SEQ ID NO 21
<211> LENGTH: 2091
<212> TYPE: PRT
<213> ORGANISM: Yarrowia lipolytica

<400> SEQUENCE: 21

Met Tyr Gly Thr Ser Thr Gly Pro Gln Thr Gly Ile Asn Thr Pro Arg
1               5                   10                  15

Ser Ser Gln Ser Leu Arg Pro Leu Ile Leu Ser His Gly Ser Leu Glu
                20                  25                  30

Phe Ser Phe Leu Val Pro Thr Ser Leu His Phe His Ala Ser Gln Leu
            35                  40                  45

Lys Asp Thr Phe Thr Ala Ser Leu Pro Glu Pro Thr Asp Glu Leu Ala
    50                  55                  60

Gln Asp Asp Glu Pro Ser Ser Val Ala Glu Leu Val Ala Arg Tyr Ile
65                  70                  75                  80

Gly His Val Ala His Glu Val Glu Glu Gly Glu Asp Ala His Gly
                85                  90                  95

Thr Asn Gln Asp Val Leu Lys Leu Thr Leu Asn Glu Phe Glu Arg Ala
            100                 105                 110

Phe Met Arg Gly Asn Asp Val His Ala Val Ala Ala Thr Leu Pro Gly
        115                 120                 125

Ile Thr Ala Lys Lys Val Leu Val Val Glu Ala Tyr Tyr Ala Gly Arg
    130                 135                 140

Ala Ala Ala Gly Arg Pro Thr Lys Pro Tyr Asp Ser Ala Leu Phe Arg
145                 150                 155                 160
```

Ala Ala Ser Asp Glu Lys Ala Arg Ile Tyr Ser Val Leu Gly Gly Gln
                165                 170                 175

Gly Asn Ile Glu Glu Tyr Phe Asp Glu Leu Arg Glu Val Tyr Asn Thr
            180                 185                 190

Tyr Thr Ser Phe Val Asp Asp Leu Ile Ser Ser Ala Glu Leu Leu
        195                 200                 205

Gln Ser Leu Ser Arg Glu Pro Asp Ala Asn Lys Leu Tyr Pro Lys Gly
    210                 215                 220

Leu Asn Val Met Gln Trp Leu Arg Glu Pro Asp Thr Gln Pro Asp Val
225                 230                 235                 240

Asp Tyr Leu Val Ser Ala Pro Val Ser Leu Pro Leu Ile Gly Leu Val
                245                 250                 255

Gln Leu Ala His Phe Ala Val Thr Cys Arg Val Leu Gly Lys Glu Pro
            260                 265                 270

Gly Glu Ile Leu Glu Arg Phe Ser Gly Thr Thr Gly His Ser Gln Gly
        275                 280                 285

Ile Val Thr Ala Ala Ala Ile Ala Thr Ala Thr Thr Trp Glu Ser Phe
    290                 295                 300

His Lys Ala Val Ala Asn Ala Leu Thr Met Leu Phe Trp Ile Gly Leu
305                 310                 315                 320

Arg Ser Gln Gln Ala Tyr Pro Arg Thr Ser Ile Ala Pro Ser Val Leu
                325                 330                 335

Gln Asp Ser Ile Glu Asn Gly Glu Gly Thr Pro Thr Pro Met Leu Ser
            340                 345                 350

Ile Arg Asp Leu Pro Arg Thr Ala Val Gln Glu His Ile Asp Met Thr
        355                 360                 365

Asn Gln His Leu Pro Glu Asp Arg His Ile Ser Ile Ser Leu Val Asn
    370                 375                 380

Ser Ala Arg Asn Phe Val Val Thr Gly Pro Pro Leu Ser Leu Tyr Gly
385                 390                 395                 400

Leu Asn Leu Arg Leu Arg Lys Val Lys Ala Pro Thr Gly Leu Asp Gln
                405                 410                 415

Asn Arg Val Pro Phe Thr Gln Arg Lys Val Arg Phe Val Asn Arg Phe
            420                 425                 430

Leu Pro Ile Thr Ala Pro Phe His Ser Gln Tyr Leu Tyr Ser Ala Phe
        435                 440                 445

Asp Arg Ile Met Glu Asp Leu Glu Asp Val Glu Ile Ser Pro Lys Ser
    450                 455                 460

Leu Thr Ile Pro Val Tyr Gly Thr Lys Thr Gly Asp Asp Leu Arg Ala
465                 470                 475                 480

Ile Ser Asp Ala Asn Val Val Pro Ala Leu Val Arg Met Ile Thr His
                485                 490                 495

Asp Pro Val Asn Trp Glu Gln Thr Thr Ala Phe Pro Asn Ala Thr His
            500                 505                 510

Ile Val Asp Phe Gly Pro Gly Gly Ile Ser Gly Leu Gly Val Leu Thr
        515                 520                 525

Asn Arg Asn Lys Asp Gly Thr Gly Val Arg Val Ile Leu Ala Gly Ser
    530                 535                 540

Met Asp Gly Thr Asn Ala Glu Val Gly Tyr Lys Pro Glu Leu Phe Asp
545                 550                 555                 560

Arg Asp Glu His Ser Val Lys Tyr Ala Ile Asp Trp Val Lys Glu Tyr
                565                 570                 575

-continued

Gly Pro Arg Leu Val Lys Asn Ala Thr Gly Gln Thr Phe Val Asp Thr
            580                 585                 590

Lys Met Ser Arg Leu Leu Gly Ile Pro Pro Ile Met Val Ala Gly Met
        595                 600                 605

Thr Pro Thr Thr Val Pro Trp Asp Phe Val Ala Ala Thr Met Asn Ala
    610                 615                 620

Gly Tyr His Ile Glu Leu Ala Gly Gly Tyr Tyr Asn Ala Lys Thr
625                 630                 635                 640

Met Thr Glu Ala Ile Thr Lys Ile Glu Lys Ala Ile Pro Pro Gly Arg
                645                 650                 655

Gly Ile Thr Val Asn Leu Ile Tyr Val Asn Pro Arg Ala Met Gly Trp
            660                 665                 670

Gln Ile Pro Leu Ile Gly Lys Leu Arg Ala Asp Gly Val Pro Ile Glu
        675                 680                 685

Gly Leu Thr Ile Gly Ala Gly Val Pro Ser Ile Glu Val Ala Asn Glu
    690                 695                 700

Tyr Ile Glu Thr Leu Gly Ile Lys His Ile Ala Phe Lys Pro Gly Ser
705                 710                 715                 720

Val Asp Ala Ile Gln Gln Val Ile Asn Ile Ala Lys Ala Asn Pro Lys
                725                 730                 735

Phe Pro Val Ile Leu Gln Trp Thr Gly Gly Arg Gly Gly His His
            740                 745                 750

Ser Phe Glu Asp Phe His Gln Pro Ile Leu Gln Met Tyr Ser Arg Ile
        755                 760                 765

Arg Arg His Glu Asn Ile Ile Leu Val Ala Gly Ser Gly Phe Gly Gly
    770                 775                 780

Ala Glu Asp Thr Tyr Pro Tyr Leu Ser Gly Asn Trp Ser Ser Arg Phe
785                 790                 795                 800

Gly Tyr Pro Pro Met Pro Phe Asp Gly Cys Leu Phe Gly Ser Arg Met
                805                 810                 815

Met Thr Ala Lys Glu Ala His Thr Ser Lys Asn Ala Lys Gln Ala Ile
            820                 825                 830

Val Asp Ala Pro Gly Leu Asp Asp Gln Asp Trp Glu Lys Thr Tyr Lys
        835                 840                 845

Gly Ala Ala Gly Gly Val Val Thr Val Leu Ser Glu Met Gly Glu Pro
850                 855                 860

Ile His Lys Leu Ala Thr Arg Gly Val Leu Phe Trp His Glu Met Asp
865                 870                 875                 880

Gln Lys Ile Phe Lys Leu Asp Lys Ala Lys Arg Val Pro Glu Leu Lys
                885                 890                 895

Lys Gln Arg Asp Tyr Ile Ile Lys Lys Leu Asn Asp Asp Phe Gln Lys
            900                 905                 910

Val Trp Phe Gly Arg Asn Ser Ala Gly Glu Thr Val Asp Leu Glu Asp
        915                 920                 925

Met Thr Tyr Ala Glu Val Val His Arg Met Val Asp Leu Met Tyr Val
    930                 935                 940

Lys His Glu Gly Arg Trp Ile Asp Asp Ser Leu Lys Lys Leu Thr Gly
945                 950                 955                 960

Asp Phe Ile Arg Arg Val Glu Glu Arg Phe Thr Ala Glu Gly Gln
                965                 970                 975

Ala Ser Leu Leu Gln Asn Tyr Ser Glu Leu Asn Val Pro Tyr Pro Ala
            980                 985                 990

Val Asp Asn Ile Leu Ala Ala Tyr  Pro Glu Ala Ala Thr  Gln Leu Ile

-continued

```
                995                 1000                1005
    Asn Ala Gln Asp Val Gln His Phe Leu Leu Cys Gln Arg Arg
        1010            1015                1020

Gly Gln Lys Pro Val Pro Phe Val Pro Ser Leu Asp Glu Asn Phe
        1025            1030                1035

Glu Tyr Trp Phe Lys Lys Asp Ser Leu Trp Gln Ser Glu Asp Leu
        1040            1045                1050

Glu Ala Val Val Gly Gln Asp Val Gly Arg Thr Cys Ile Leu Gln
        1055            1060                1065

Gly Pro Met Ala Ala Lys Phe Ser Thr Val Ile Asp Glu Pro Val
        1070            1075                1080

Gly Asp Ile Leu Asn Ser Ile His Gln Gly His Ile Lys Ser Leu
        1085            1090                1095

Ile Lys Asp Met Tyr Asn Gly Asp Glu Thr Thr Ile Pro Ile Thr
        1100            1105                1110

Glu Tyr Phe Gly Gly Arg Leu Ser Glu Ala Gln Glu Asp Ile Glu
        1115            1120                1125

Met Asp Gly Leu Thr Ile Ser Glu Asp Ala Asn Lys Ile Ser Tyr
        1130            1135                1140

Arg Leu Ser Ser Ser Ala Ala Asp Leu Pro Glu Val Asn Arg Trp
        1145            1150                1155

Cys Arg Leu Leu Ala Gly Arg Ser Tyr Ser Trp Arg His Ala Leu
        1160            1165                1170

Phe Ser Ala Asp Val Phe Val Gln Gly His Arg Phe Gln Thr Asn
        1175            1180                1185

Pro Leu Lys Arg Val Leu Ala Pro Ser Thr Gly Met Tyr Val Glu
        1190            1195                1200

Ile Ala Asn Pro Glu Asp Ala Pro Lys Thr Val Ile Ser Val Arg
        1205            1210                1215

Glu Pro Tyr Gln Ser Gly Lys Leu Val Lys Thr Val Asp Ile Lys
        1220            1225                1230

Leu Asn Glu Lys Gly Pro Ile Ala Leu Thr Leu Tyr Glu Gly Arg
        1235            1240                1245

Thr Ala Glu Asn Gly Val Val Pro Leu Thr Phe Leu Phe Thr Tyr
        1250            1255                1260

His Pro Asp Thr Gly Tyr Ala Pro Ile Arg Glu Val Met Asp Ser
        1265            1270                1275

Arg Asn Asp Arg Ile Lys Glu Phe Tyr Tyr Arg Ile Trp Phe Gly
        1280            1285                1290

Asn Lys Asp Val Pro Phe Tyr Thr Pro Thr Thr Ala Thr Phe Asn
        1295            1300                1305

Gly Gly Arg Glu Thr Ile Thr Ser Gln Ala Val Ala Asp Phe Val
        1310            1315                1320

His Ala Val Gly Asn Thr Gly Glu Ala Phe Val Glu Arg Pro Gly
        1325            1330                1335

Lys Glu Val Phe Ala Pro Met Asp Phe Ala Ile Val Ala Gly Trp
        1340            1345                1350

Lys Ala Ile Thr Lys Pro Ile Phe Pro Arg Thr Ile Asp Gly Asp
        1355            1360                1365

Leu Leu Lys Leu Val His Leu Ser Asn Gly Phe Lys Met Val Pro
        1370            1375                1380

Gly Ala Gln Pro Leu Lys Val Gly Asp Val Leu Asp Thr Thr Ala
        1385            1390                1395
```

Gln Ile Asn Ser Ile Ile Asn Glu Glu Ser Gly Lys Ile Val Glu
    1400                1405                1410

Val Cys Gly Thr Ile Arg Arg Asp Gly Lys Pro Ile Met His Val
    1415                1420                1425

Thr Ser Gln Phe Leu Tyr Arg Gly Ala Tyr Thr Asp Phe Glu Asn
    1430                1435                1440

Thr Phe Gln Arg Lys Asp Glu Val Pro Met Gln Val His Leu Ala
    1445                1450                1455

Ser Ser Arg Asp Val Ala Ile Leu Arg Ser Lys Glu Trp Phe Arg
    1460                1465                1470

Leu Asp Met Asp Val Glu Leu Leu Gly Gln Thr Leu Thr Phe
    1475                1480                1485

Arg Leu Gln Ser Leu Ile Arg Phe Lys Asn Lys Asn Val Phe Ser
    1490                1495                1500

Gln Val Gln Thr Met Gly Gln Val Leu Leu Glu Leu Pro Thr Lys
    1505                1510                1515

Glu Val Ile Gln Val Ala Ser Val Asp Tyr Glu Ala Gly Thr Ser
    1520                1525                1530

His Gly Asn Pro Val Ile Asp Tyr Leu Gln Arg Asn Gly Thr Ser
    1535                1540                1545

Ile Glu Gln Pro Val Tyr Phe Glu Asn Pro Ile Pro Leu Ser Gly
    1550                1555                1560

Lys Thr Pro Leu Val Leu Arg Ala Pro Ala Ser Asn Glu Thr Tyr
    1565                1570                1575

Ala Arg Val Ser Gly Asp Tyr Asn Pro Ile His Val Ser Arg Val
    1580                1585                1590

Phe Ser Ser Tyr Ala Asn Leu Pro Gly Thr Ile Thr His Gly Met
    1595                1600                1605

Tyr Thr Ser Ala Ala Val Arg Ser Leu Val Glu Thr Trp Ala Ala
    1610                1615                1620

Glu Asn Asn Ile Gly Arg Val Arg Gly Phe His Val Ser Leu Val
    1625                1630                1635

Asp Met Val Leu Pro Asn Asp Leu Ile Thr Val Arg Leu Gln His
    1640                1645                1650

Val Gly Met Ile Ala Gly Arg Lys Ile Ile Lys Val Glu Ala Ser
    1655                1660                1665

Asn Lys Glu Thr Glu Asp Lys Val Leu Leu Gly Glu Ala Glu Val
    1670                1675                1680

Glu Gln Pro Val Thr Ala Tyr Val Phe Thr Gly Gln Gly Ser Gln
    1685                1690                1695

Glu Gln Gly Met Gly Met Glu Leu Tyr Ala Thr Ser Pro Val Ala
    1700                1705                1710

Lys Glu Val Trp Asp Arg Pro Ser Phe His Trp Asn Tyr Gly Leu
    1715                1720                1725

Ser Ile Ile Asp Ile Val Lys Asn Asn Pro Lys Glu Arg Thr Val
    1730                1735                1740

His Phe Gly Gly Pro Arg Gly Lys Ala Ile Arg Gln Asn Tyr Met
    1745                1750                1755

Ser Met Thr Phe Glu Thr Val Asn Ala Asp Gly Thr Ile Lys Ser
    1760                1765                1770

Glu Lys Ile Phe Lys Glu Ile Asp Glu Thr Thr Thr Ser Tyr Thr
    1775                1780                1785

-continued

Tyr Arg Ser Pro Thr Gly Leu Leu Ser Ala Thr Gln Phe Thr Gln
    1790            1795                1800

Pro Ala Leu Thr Leu Met Glu Lys Ala Ser Phe Glu Asp Met Arg
    1805            1810                1815

Ser Lys Gly Leu Val Gln Arg Asp Ser Ser Phe Ala Gly His Ser
    1820            1825                1830

Leu Gly Glu Tyr Ser Ala Leu Ala Asp Leu Ala Asp Val Met Leu
    1835            1840                1845

Ile Glu Ser Leu Val Ser Val Val Phe Tyr Arg Gly Leu Thr Met
    1850            1855                1860

Gln Val Ala Val Glu Arg Asp Glu Gln Gly Arg Ser Asn Tyr Ser
    1865            1870                1875

Met Cys Ala Val Asn Pro Ser Arg Ile Ser Lys Thr Phe Asn Glu
    1880            1885                1890

Gln Ala Leu Gln Tyr Val Val Gly Asn Ile Ser Glu Gln Thr Gly
    1895            1900                1905

Trp Leu Leu Glu Ile Val Asn Tyr Asn Val Ala Asn Met Gln Tyr
    1910            1915                1920

Val Ala Ala Gly Asp Leu Arg Ala Leu Asp Cys Leu Thr Asn Leu
    1925            1930                1935

Leu Asn Tyr Leu Lys Ala Gln Asn Ile Asp Ile Pro Ala Leu Met
    1940            1945                1950

Gln Ser Met Ser Leu Glu Asp Val Lys Ala His Leu Val Asn Ile
    1955            1960                1965

Ile His Glu Cys Val Lys Gln Thr Glu Ala Lys Pro Lys Pro Ile
    1970            1975                1980

Asn Leu Glu Arg Gly Phe Ala Thr Ile Pro Leu Lys Gly Ile Asp
    1985            1990                1995

Val Pro Phe His Ser Thr Phe Leu Arg Ser Gly Val Lys Pro Phe
    2000            2005                2010

Arg Ser Phe Leu Ile Lys Lys Ile Asn Lys Thr Thr Ile Asp Pro
    2015            2020                2025

Ser Lys Leu Val Gly Lys Tyr Ile Pro Asn Val Thr Ala Arg Pro
    2030            2035                2040

Phe Glu Ile Thr Lys Glu Tyr Phe Glu Asp Val Tyr Arg Leu Thr
    2045            2050                2055

Asn Ser Pro Arg Ile Ala His Ile Leu Ala Asn Trp Glu Lys Tyr
    2060            2065                2070

Glu Glu Gly Thr Glu Gly Gly Ser Arg His Gly Gly Thr Thr Ala
    2075            2080                2085

Ala Ser Ser
    2090

<210> SEQ ID NO 22
<211> LENGTH: 482
<212> TYPE: PRT
<213> ORGANISM: Yarrowia lipolytica

<400> SEQUENCE: 22

Met Val Lys Asn Val Asp Gln Val Asp Leu Ser Gln Val Asp Thr Ile
1               5                   10                  15

Ala Ser Gly Arg Asp Val Asn Tyr Lys Val Lys Tyr Thr Ser Gly Val
            20                  25                  30

Lys Met Ser Gln Gly Ala Tyr Asp Asp Lys Gly Arg His Ile Ser Glu
        35                  40                  45

```
Gln Pro Phe Thr Trp Ala Asn Trp His Gln His Ile Asn Trp Leu Asn
    50                  55                  60
Phe Ile Leu Val Ile Ala Leu Pro Leu Ser Ser Phe Ala Ala Ala Pro
65                  70                  75                  80
Phe Val Ser Phe Asn Trp Lys Thr Ala Ala Phe Ala Val Gly Tyr Tyr
                    85                  90                  95
Met Cys Thr Gly Leu Gly Ile Thr Ala Gly Tyr His Arg Met Trp Ala
                100                 105                 110
His Arg Ala Tyr Lys Ala Ala Leu Pro Val Arg Ile Ile Leu Ala Leu
            115                 120                 125
Phe Gly Gly Ala Val Glu Gly Ser Ile Arg Trp Trp Ala Ser Ser
    130                 135                 140
His Arg Val His His Arg Trp Thr Asp Ser Asn Lys Asp Pro Tyr Asp
145                 150                 155                 160
Ala Arg Lys Gly Phe Trp Phe Ser His Phe Gly Trp Met Leu Leu Val
                    165                 170                 175
Pro Asn Pro Lys Asn Lys Gly Arg Thr Asp Ile Ser Asp Leu Asn Asn
                180                 185                 190
Asp Trp Val Val Arg Leu Gln His Lys Tyr Tyr Val Tyr Val Leu Val
            195                 200                 205
Phe Met Ala Ile Val Leu Pro Thr Leu Val Cys Gly Phe Gly Trp Gly
    210                 215                 220
Asp Trp Lys Gly Gly Leu Val Tyr Ala Gly Ile Met Arg Tyr Thr Phe
225                 230                 235                 240
Val Gln Gln Val Thr Phe Cys Val Asn Ser Leu Ala His Trp Ile Gly
                    245                 250                 255
Glu Gln Pro Phe Asp Asp Arg Arg Thr Pro Arg Asp His Ala Leu Thr
                260                 265                 270
Ala Leu Val Thr Phe Gly Glu Gly Tyr His Asn Phe His His Glu Phe
            275                 280                 285
Pro Ser Asp Tyr Arg Asn Ala Leu Ile Trp Tyr Gln Tyr Asp Pro Thr
    290                 295                 300
Lys Trp Leu Ile Trp Thr Leu Lys Gln Val Gly Leu Ala Trp Asp Leu
305                 310                 315                 320
Gln Thr Phe Ser Gln Asn Ala Ile Glu Gln Gly Leu Val Gln Gln Arg
                    325                 330                 335
Gln Lys Lys Leu Asp Lys Trp Arg Asn Asn Leu Asn Trp Gly Ile Pro
                340                 345                 350
Ile Glu Gln Leu Pro Val Ile Glu Phe Glu Glu Phe Gln Glu Gln Ala
            355                 360                 365
Lys Thr Arg Asp Leu Val Leu Ile Ser Gly Ile Val His Asp Val Ser
    370                 375                 380
Ala Phe Val Glu His His Pro Gly Gly Lys Ala Leu Ile Met Ser Ala
385                 390                 395                 400
Val Gly Lys Asp Gly Thr Ala Val Phe Asn Gly Val Tyr Arg His
                    405                 410                 415
Ser Asn Ala Gly His Asn Leu Leu Ala Thr Met Arg Val Ser Val Ile
                420                 425                 430
Arg Gly Gly Met Glu Val Glu Val Trp Lys Thr Ala Gln Asn Glu Lys
            435                 440                 445
Lys Asp Gln Asn Ile Val Ser Asp Glu Ser Gly Asn Arg Ile His Arg
    450                 455                 460
```

```
Ala Gly Leu Gln Ala Thr Arg Val Glu Asn Pro Gly Met Ser Gly Met
465                 470                 475                 480

Ala Ala

<210> SEQ ID NO 23
<211> LENGTH: 2266
<212> TYPE: PRT
<213> ORGANISM: Yarrowia lipolytica

<400> SEQUENCE: 23

Met Arg Leu Gln Leu Arg Thr Leu Thr Arg Arg Phe Phe Ser Met Ala
1               5                   10                  15

Ser Gly Ser Ser Thr Pro Asp Val Ala Pro Leu Val Asp Pro Asn Ile
            20                  25                  30

His Lys Gly Leu Ala Ser His Phe Gly Leu Asn Ser Val His Thr
        35                  40                  45

Ala Lys Pro Ser Lys Val Lys Glu Phe Val Ala Ser His Gly Gly His
50                  55                  60

Thr Val Ile Asn Lys Val Leu Ile Ala Asn Asn Gly Ile Ala Ala Val
65                  70                  75                  80

Lys Glu Ile Arg Ser Val Arg Lys Trp Ala Tyr Glu Thr Phe Gly Asp
                85                  90                  95

Glu Arg Ala Ile Ser Phe Thr Val Met Ala Thr Pro Glu Asp Leu Ala
            100                 105                 110

Ala Asn Ala Asp Tyr Ile Arg Met Ala Asp Gln Tyr Val Glu Val Pro
        115                 120                 125

Gly Gly Thr Asn Asn Asn Tyr Ala Asn Val Glu Leu Ile Val Asp
130                 135                 140

Val Ala Glu Arg Phe Gly Val Asp Ala Val Trp Ala Gly Trp Gly His
145                 150                 155                 160

Ala Ser Glu Asn Pro Leu Leu Pro Glu Ser Leu Ala Ala Ser Pro Arg
                165                 170                 175

Lys Ile Val Phe Ile Gly Pro Pro Gly Ala Ala Met Arg Ser Leu Gly
            180                 185                 190

Asp Lys Ile Ser Ser Thr Ile Val Ala Gln His Ala Lys Val Pro Cys
        195                 200                 205

Ile Pro Trp Ser Gly Thr Gly Val Asp Glu Val Val Asp Lys Ser
210                 215                 220

Thr Asn Leu Val Ser Val Ser Glu Glu Val Tyr Thr Lys Gly Cys Thr
225                 230                 235                 240

Thr Gly Pro Lys Gln Gly Leu Glu Lys Ala Lys Gln Ile Gly Phe Pro
                245                 250                 255

Val Met Ile Lys Ala Ser Glu Gly Gly Gly Gly Lys Gly Ile Arg Lys
            260                 265                 270

Val Glu Arg Glu Glu Asp Phe Glu Ala Ala Tyr His Gln Val Glu Gly
        275                 280                 285

Glu Ile Pro Gly Ser Pro Ile Phe Ile Met Gln Leu Ala Gly Asn Ala
290                 295                 300

Arg His Leu Glu Val Gln Leu Leu Ala Asp Gln Tyr Gly Asn Asn Ile
305                 310                 315                 320

Ser Leu Phe Gly Arg Asp Cys Ser Val Gln Arg Arg His Gln Lys Ile
                325                 330                 335

Ile Glu Glu Ala Pro Val Thr Val Ala Gly Gln Gln Thr Phe Thr Ala
            340                 345                 350
```

```
Met Glu Lys Ala Ala Val Arg Leu Gly Lys Leu Val Gly Tyr Val Ser
            355                 360                 365
Ala Gly Thr Val Glu Tyr Leu Tyr Ser His Glu Asp Asp Lys Phe Tyr
        370                 375                 380
Phe Leu Glu Leu Asn Pro Arg Leu Gln Val Glu His Pro Thr Thr Glu
385                 390                 395                 400
Met Val Thr Gly Val Asn Leu Pro Ala Ala Gln Leu Gln Ile Ala Met
                405                 410                 415
Gly Ile Pro Leu Asp Arg Ile Lys Asp Ile Arg Leu Phe Tyr Gly Val
            420                 425                 430
Asn Pro His Thr Thr Thr Pro Ile Asp Phe Asp Phe Ser Gly Glu Asp
        435                 440                 445
Ala Asp Lys Thr Gln Arg Arg Pro Val Pro Arg Gly His Thr Thr Ala
    450                 455                 460
Cys Arg Ile Thr Ser Glu Asp Pro Gly Glu Gly Phe Lys Pro Ser Gly
465                 470                 475                 480
Gly Thr Met His Glu Leu Asn Phe Arg Ser Ser Asn Val Trp Gly
                485                 490                 495
Tyr Phe Ser Val Gly Asn Gln Gly Gly Ile His Ser Phe Ser Asp Ser
            500                 505                 510
Gln Phe Gly His Ile Phe Ala Phe Gly Glu Asn Arg Ser Ala Ser Arg
        515                 520                 525
Lys His Met Val Val Ala Leu Lys Glu Leu Ser Ile Arg Gly Asp Phe
    530                 535                 540
Arg Thr Thr Val Glu Tyr Leu Ile Lys Leu Leu Glu Thr Pro Asp Phe
545                 550                 555                 560
Glu Asp Asn Thr Ile Thr Thr Gly Trp Leu Asp Glu Leu Ile Ser Asn
                565                 570                 575
Lys Leu Thr Ala Glu Arg Pro Asp Ser Phe Leu Ala Val Val Cys Gly
            580                 585                 590
Ala Ala Thr Lys Ala His Arg Ala Ser Glu Asp Ser Ile Ala Thr Tyr
        595                 600                 605
Met Ala Ser Leu Glu Lys Gly Gln Val Pro Ala Arg Asp Ile Leu Lys
    610                 615                 620
Thr Leu Phe Pro Val Asp Phe Ile Tyr Glu Gly Gln Arg Tyr Lys Phe
625                 630                 635                 640
Thr Ala Thr Arg Ser Ser Glu Asp Ser Tyr Thr Leu Phe Ile Asn Gly
                645                 650                 655
Ser Arg Cys Asp Ile Gly Val Arg Pro Leu Ser Asp Gly Gly Ile Leu
            660                 665                 670
Cys Leu Val Gly Gly Arg Ser His Asn Val Tyr Trp Lys Glu Glu Val
        675                 680                 685
Gly Ala Thr Arg Leu Ser Val Asp Ser Lys Thr Cys Leu Leu Glu Val
    690                 695                 700
Glu Asn Asp Pro Thr Gln Leu Arg Ser Pro Ser Gly Lys Leu Val
705                 710                 715                 720
Lys Phe Leu Val Glu Asn Gly Asp His Val Arg Ala Asn Gln Pro Tyr
                725                 730                 735
Ala Glu Ile Glu Val Met Lys Met Tyr Met Thr Leu Thr Ala Gln Glu
            740                 745                 750
Asp Gly Ile Val Gln Leu Met Lys Gln Pro Gly Ser Thr Ile Glu Ala
        755                 760                 765
Gly Asp Ile Leu Gly Ile Leu Ala Leu Asp Asp Pro Ser Lys Val Lys
```

```
                770             775             780
His Ala Lys Pro Phe Glu Gly Gln Leu Pro Glu Leu Gly Pro Pro Thr
785                 790                 795                 800

Leu Ser Gly Asn Lys Pro His Gln Arg Tyr Glu His Cys Gln Asn Val
                805                 810                 815

Leu His Asn Ile Leu Leu Gly Phe Asp Asn Gln Val Val Met Lys Ser
                820                 825                 830

Thr Leu Gln Glu Met Val Gly Leu Leu Arg Asn Pro Glu Leu Pro Tyr
                835                 840                 845

Leu Gln Trp Ala His Gln Val Ser Ser Leu His Thr Arg Met Ser Ala
                850                 855                 860

Lys Leu Asp Ala Thr Leu Ala Gly Leu Ile Asp Lys Ala Lys Gln Arg
865                 870                 875                 880

Gly Gly Glu Phe Pro Ala Lys Gln Leu Leu Arg Ala Leu Glu Lys Glu
                885                 890                 895

Ala Ser Ser Gly Glu Val Asp Ala Leu Phe Gln Gln Thr Leu Ala Pro
                900                 905                 910

Leu Phe Asp Leu Ala Arg Glu Tyr Gln Asp Gly Leu Ala Ile His Glu
                915                 920                 925

Leu Gln Val Ala Ala Gly Leu Leu Gln Ala Tyr Tyr Asp Ser Glu Ala
                930                 935                 940

Arg Phe Cys Gly Pro Asn Val Arg Asp Glu Asp Val Ile Leu Lys Leu
945                 950                 955                 960

Arg Glu Glu Asn Arg Asp Ser Leu Arg Lys Val Val Met Ala Gln Leu
                965                 970                 975

Ser His Ser Arg Val Gly Ala Lys Asn Asn Leu Val Leu Ala Leu Leu
                980                 985                 990

Asp Glu Tyr Lys Val Ala Asp Gln Ala Gly Thr Asp Ser Pro Ala Ser
                995                 1000                1005

Asn Val His Val Ala Lys Tyr Leu Arg Pro Val Leu Arg Lys Ile
    1010                1015                1020

Val Glu Leu Glu Ser Arg Ala Ser Ala Lys Val Ser Leu Lys Ala
    1025                1030                1035

Arg Glu Ile Leu Ile Gln Cys Ala Leu Pro Ser Leu Lys Glu Arg
    1040                1045                1050

Thr Asp Gln Leu Glu His Ile Leu Arg Ser Ser Val Val Glu Ser
    1055                1060                1065

Arg Tyr Gly Glu Val Gly Leu Glu His Arg Thr Pro Arg Ala Asp
    1070                1075                1080

Ile Leu Lys Glu Val Val Asp Ser Lys Tyr Ile Val Phe Asp Val
    1085                1090                1095

Leu Ala Gln Phe Phe Ala His Asp Asp Pro Trp Ile Val Leu Ala
    1100                1105                1110

Ala Leu Glu Leu Tyr Ile Arg Arg Ala Cys Lys Ala Tyr Ser Ile
    1115                1120                1125

Leu Asp Ile Asn Tyr His Gln Asp Ser Asp Leu Pro Pro Val Ile
    1130                1135                1140

Ser Trp Arg Phe Arg Leu Pro Thr Met Ser Ser Ala Leu Tyr Asn
    1145                1150                1155

Ser Val Val Ser Ser Gly Ser Lys Thr Pro Thr Ser Pro Ser Val
    1160                1165                1170

Ser Arg Ala Asp Ser Val Ser Asp Phe Ser Tyr Thr Val Glu Arg
    1175                1180                1185
```

-continued

Asp Ser Ala Pro Ala Arg Thr Gly Ala Ile Val Ala Val Pro His
1190              1195                1200

Leu Asp Asp Leu Glu Asp Ala Leu Thr Arg Val Leu Glu Asn Leu
1205              1210                1215

Pro Lys Arg Gly Ala Gly Leu Ala Ile Ser Val Gly Ala Ser Asn
1220              1225                1230

Lys Ser Ala Ala Ala Ser Ala Arg Asp Ala Ala Ala Ala Ala Ala
1235              1240                1245

Ser Ser Val Asp Thr Gly Leu Ser Asn Ile Cys Asn Val Met Ile
1250              1255                1260

Gly Arg Val Asp Glu Ser Asp Asp Asp Thr Leu Ile Ala Arg
1265              1270                1275

Ile Ser Gln Val Ile Glu Asp Phe Lys Glu Asp Phe Glu Ala Cys
1280              1285                1290

Ser Leu Arg Arg Ile Thr Phe Ser Phe Gly Asn Ser Arg Gly Thr
1295              1300                1305

Tyr Pro Lys Tyr Phe Thr Phe Arg Gly Pro Ala Tyr Glu Glu Asp
1310              1315                1320

Pro Thr Ile Arg His Ile Glu Pro Ala Leu Ala Phe Gln Leu Glu
1325              1330                1335

Leu Ala Arg Leu Ser Asn Phe Asp Ile Lys Pro Val His Thr Asp
1340              1345                1350

Asn Arg Asn Ile His Val Tyr Glu Ala Thr Gly Lys Asn Ala Ala
1355              1360                1365

Ser Asp Lys Arg Phe Phe Thr Arg Gly Ile Val Arg Pro Gly Arg
1370              1375                1380

Leu Arg Glu Asn Ile Pro Thr Ser Glu Tyr Leu Ile Ser Glu Ala
1385              1390                1395

Asp Arg Leu Met Ser Asp Ile Leu Asp Ala Leu Glu Val Ile Gly
1400              1405                1410

Thr Thr Asn Ser Asp Leu Asn His Ile Phe Ile Asn Phe Ser Ala
1415              1420                1425

Val Phe Ala Leu Lys Pro Glu Glu Val Glu Ala Ala Phe Gly Gly
1430              1435                1440

Phe Leu Glu Arg Phe Gly Arg Arg Leu Trp Arg Leu Arg Val Thr
1445              1450                1455

Gly Ala Glu Ile Arg Met Met Val Ser Asp Pro Glu Thr Gly Ser
1460              1465                1470

Ala Phe Pro Leu Arg Ala Met Ile Asn Asn Val Ser Gly Tyr Val
1475              1480                1485

Val Gln Ser Glu Leu Tyr Ala Glu Ala Lys Asn Asp Lys Gly Gln
1490              1495                1500

Trp Ile Phe Lys Ser Leu Gly Lys Pro Gly Ser Met His Met Arg
1505              1510                1515

Ser Ile Asn Thr Pro Tyr Pro Thr Lys Glu Trp Leu Gln Pro Lys
1520              1525                1530

Arg Tyr Lys Ala His Leu Met Gly Thr Thr Tyr Cys Tyr Asp Phe
1535              1540                1545

Pro Glu Leu Phe Arg Gln Ser Ile Glu Ser Asp Trp Lys Lys Tyr
1550              1555                1560

Asp Gly Lys Ala Pro Asp Asp Leu Met Thr Cys Asn Glu Leu Ile
1565              1570                1575

```
Leu Asp Glu Asp Ser Gly Glu Leu Gln Glu Val Asn Arg Glu Pro
    1580            1585            1590

Gly Ala Asn Asn Val Gly Met Val Ala Trp Lys Phe Glu Ala Lys
    1595            1600            1605

Thr Pro Glu Tyr Pro Arg Gly Arg Ser Phe Ile Val Val Ala Asn
    1610            1615            1620

Asp Ile Thr Phe Gln Ile Gly Ser Phe Gly Pro Ala Glu Asp Gln
    1625            1630            1635

Phe Phe Phe Lys Val Thr Glu Leu Ala Arg Lys Leu Gly Ile Pro
    1640            1645            1650

Arg Ile Tyr Leu Ser Ala Asn Ser Gly Ala Arg Ile Gly Ile Ala
    1655            1660            1665

Asp Glu Leu Val Gly Lys Tyr Lys Val Ala Trp Asn Asp Glu Thr
    1670            1675            1680

Asp Pro Ser Lys Gly Phe Lys Tyr Leu Tyr Phe Thr Pro Glu Ser
    1685            1690            1695

Leu Ala Thr Leu Lys Pro Asp Thr Val Val Thr Thr Glu Ile Glu
    1700            1705            1710

Glu Glu Gly Pro Asn Gly Val Glu Lys Arg His Val Ile Asp Tyr
    1715            1720            1725

Ile Val Gly Glu Lys Asp Gly Leu Gly Val Glu Cys Leu Arg Gly
    1730            1735            1740

Ser Gly Leu Ile Ala Gly Ala Thr Ser Arg Ala Tyr Lys Asp Ile
    1745            1750            1755

Phe Thr Leu Thr Leu Val Thr Cys Arg Ser Val Gly Ile Gly Ala
    1760            1765            1770

Tyr Leu Val Arg Leu Gly Gln Arg Ala Ile Gln Ile Glu Gly Gln
    1775            1780            1785

Pro Ile Ile Leu Thr Gly Ala Pro Ala Ile Asn Lys Leu Leu Gly
    1790            1795            1800

Arg Glu Val Tyr Ser Ser Asn Leu Gln Leu Gly Gly Thr Gln Ile
    1805            1810            1815

Met Tyr Asn Asn Gly Val Ser His Leu Thr Ala Arg Asp Asp Leu
    1820            1825            1830

Asn Gly Val His Lys Ile Met Gln Trp Leu Ser Tyr Ile Pro Ala
    1835            1840            1845

Ser Arg Gly Leu Pro Val Pro Val Leu Pro His Lys Thr Asp Val
    1850            1855            1860

Trp Asp Arg Asp Val Thr Phe Gln Pro Val Arg Gly Glu Gln Tyr
    1865            1870            1875

Asp Val Arg Trp Leu Ile Ser Gly Arg Thr Leu Glu Asp Gly Ala
    1880            1885            1890

Phe Glu Ser Gly Leu Phe Asp Lys Asp Ser Phe Gln Glu Thr Leu
    1895            1900            1905

Ser Gly Trp Ala Lys Gly Val Val Val Gly Arg Ala Arg Leu Gly
    1910            1915            1920

Gly Ile Pro Phe Gly Val Ile Gly Val Glu Thr Ala Thr Val Asp
    1925            1930            1935

Asn Thr Thr Pro Ala Asp Pro Ala Asn Pro Asp Ser Ile Glu Met
    1940            1945            1950

Ser Thr Ser Glu Ala Gly Gln Val Trp Tyr Pro Asn Ser Ala Phe
    1955            1960            1965

Lys Thr Ser Gln Ala Ile Asn Asp Phe Asn His Gly Glu Ala Leu
```

```
                1970                1975                1980

Pro Leu Met Ile Leu Ala Asn Trp Arg Gly Phe Ser Gly Gly Gln
            1985                1990                1995

Arg Asp Met Tyr Asn Glu Val Leu Lys Tyr Gly Ser Phe Ile Val
            2000                2005                2010

Asp Ala Leu Val Asp Tyr Lys Gln Pro Ile Met Val Tyr Ile Pro
            2015                2020                2025

Pro Thr Gly Glu Leu Arg Gly Gly Ser Trp Val Val Asp Pro
            2030                2035                2040

Thr Ile Asn Ser Asp Met Met Glu Met Tyr Ala Asp Val Glu Ser
            2045                2050                2055

Arg Gly Gly Val Leu Glu Pro Glu Gly Met Val Gly Ile Lys Tyr
            2060                2065                2070

Arg Arg Asp Lys Leu Leu Asp Thr Met Ala Arg Leu Asp Pro Glu
            2075                2080                2085

Tyr Ser Ser Leu Lys Lys Gln Leu Glu Glu Ser Pro Asp Ser Glu
            2090                2095                2100

Glu Leu Lys Val Lys Leu Ser Val Arg Glu Lys Ser Leu Met Pro
            2105                2110                2115

Ile Tyr Gln Gln Ile Ser Val Gln Phe Ala Asp Leu His Asp Arg
            2120                2125                2130

Ala Gly Arg Met Glu Ala Lys Gly Val Ile Arg Glu Ala Leu Val
            2135                2140                2145

Trp Lys Asp Ala Arg Arg Phe Phe Phe Trp Arg Ile Arg Arg Arg
            2150                2155                2160

Leu Val Glu Glu Tyr Leu Ile Thr Lys Ile Asn Ser Ile Leu Pro
            2165                2170                2175

Ser Cys Thr Arg Leu Glu Cys Leu Ala Arg Ile Lys Ser Trp Lys
            2180                2185                2190

Pro Ala Thr Leu Asp Gln Gly Ser Asp Arg Gly Val Ala Glu Trp
            2195                2200                2205

Phe Asp Glu Asn Ser Asp Ala Val Ser Ala Arg Leu Ser Glu Leu
            2210                2215                2220

Lys Lys Asp Ala Ser Ala Gln Ser Phe Ala Ser Gln Leu Arg Lys
            2225                2230                2235

Asp Arg Gln Gly Thr Leu Gly Gly Met Lys Gln Ala Leu Ala Ser
            2240                2245                2250

Leu Ser Glu Ala Glu Arg Ala Glu Leu Leu Lys Gly Leu
            2255                2260                2265

<210> SEQ ID NO 24
<211> LENGTH: 514
<212> TYPE: PRT
<213> ORGANISM: Yarrowia lipolytica

<400> SEQUENCE: 24

Met Thr Ile Asp Ser Gln Tyr Tyr Lys Ser Arg Asp Lys Asn Asp Thr
1               5                   10                  15

Ala Pro Lys Ile Ala Gly Ile Arg Tyr Ala Pro Leu Ser Thr Pro Leu
            20                  25                  30

Leu Asn Arg Cys Glu Thr Phe Ser Leu Val Trp His Ile Phe Ser Ile
        35                  40                  45

Pro Thr Phe Leu Thr Ile Phe Met Leu Cys Cys Ala Ile Pro Leu Leu
    50                  55                  60
```

-continued

```
Trp Pro Phe Val Ile Ala Tyr Val Val Tyr Ala Val Lys Asp Asp Ser
 65                  70                  75                  80

Pro Ser Asn Gly Gly Val Val Lys Arg Tyr Ser Pro Ile Ser Arg Asn
             85                  90                  95

Phe Phe Ile Trp Lys Leu Phe Gly Arg Tyr Phe Pro Ile Thr Leu His
            100                 105                 110

Lys Thr Val Asp Leu Glu Pro Thr His Thr Tyr Pro Leu Asp Val
        115                 120                 125

Gln Glu Tyr His Leu Ile Ala Glu Arg Tyr Trp Pro Gln Asn Lys Tyr
        130                 135                 140

Leu Arg Ala Ile Ile Ser Thr Ile Glu Tyr Phe Leu Pro Ala Phe Met
145                 150                 155                 160

Lys Arg Ser Leu Ser Ile Asn Glu Gln Glu Gln Pro Ala Glu Arg Asp
            165                 170                 175

Pro Leu Leu Ser Pro Val Ser Pro Ser Pro Gly Ser Gln Pro Asp
            180                 185                 190

Lys Trp Ile Asn His Asp Ser Arg Tyr Ser Arg Gly Glu Ser Ser Gly
            195                 200                 205

Ser Asn Gly His Ala Ser Gly Ser Glu Leu Asn Gly Asn Gly Asn Asn
210                 215                 220

Gly Thr Thr Asn Arg Arg Pro Leu Ser Ser Ala Ser Ala Gly Ser Thr
225                 230                 235                 240

Ala Ser Asp Ser Thr Leu Leu Asn Gly Ser Leu Asn Ser Tyr Ala Asn
                245                 250                 255

Gln Ile Ile Gly Glu Asn Asp Pro Gln Leu Ser Pro Thr Lys Leu Lys
            260                 265                 270

Pro Thr Gly Arg Lys Tyr Ile Phe Gly Tyr His Pro His Gly Ile Ile
            275                 280                 285

Gly Met Gly Ala Phe Gly Gly Ile Ala Thr Glu Gly Ala Gly Trp Ser
            290                 295                 300

Lys Leu Phe Pro Gly Ile Pro Val Ser Leu Met Thr Leu Thr Asn Asn
305                 310                 315                 320

Phe Arg Val Pro Leu Tyr Arg Glu Tyr Leu Met Ser Leu Gly Val Ala
                325                 330                 335

Ser Val Ser Lys Lys Ser Cys Lys Ala Leu Leu Lys Arg Asn Gln Ser
            340                 345                 350

Ile Cys Ile Val Val Gly Gly Ala Gln Glu Ser Leu Leu Ala Arg Pro
            355                 360                 365

Gly Val Met Asp Leu Val Leu Leu Lys Arg Lys Gly Phe Val Arg Leu
            370                 375                 380

Gly Met Glu Val Gly Asn Val Ala Leu Val Pro Ile Met Ala Phe Gly
385                 390                 395                 400

Glu Asn Asp Leu Tyr Asp Gln Val Ser Asn Asp Lys Ser Ser Lys Leu
                405                 410                 415

Tyr Arg Phe Gln Gln Phe Val Lys Asn Phe Leu Gly Phe Thr Leu Pro
            420                 425                 430

Leu Met His Ala Arg Gly Val Phe Asn Tyr Asp Val Gly Leu Val Pro
            435                 440                 445

Tyr Arg Arg Pro Val Asn Ile Val Gly Ser Pro Ile Asp Leu Pro
            450                 455                 460

Tyr Leu Pro His Pro Thr Asp Glu Glu Val Ser Glu Tyr His Asp Arg
465                 470                 475                 480

Tyr Ile Ala Glu Leu Gln Arg Ile Tyr Asn Glu His Lys Asp Glu Tyr
```

-continued

```
                485                 490                 495
Phe Ile Asp Trp Thr Glu Glu Gly Lys Gly Ala Pro Glu Phe Arg Met
            500                 505                 510
Ile Glu
```

PRODUCTION OF CANNABINOIDS IN YEAST

PRIORITY DOCUMENTS

The present application is a 5371 National Stage Application of PCT/US18/41890 filed on Jul. 12, 2018, which claims priority to U.S. Provisional Patent Application No. 62/531,827 filed on 12 Jul. 2017, the content of which are hereby incorporated by reference in its entirety.

TECHNICAL FIELD

The present disclosure relates to the production of cannabinoids in yeast.

BACKGROUND

Cannabinoids are a general class of chemicals that act on cannabinoid receptors and other target molecules to modulate a wide range of physiological behaviour such as neurotransmitter release. Cannabinoids are produced naturally in humans (called endocannabinoids) and by several plant species (called phytocannabinoids) including *Cannabis sativa*. Cannabinoids have been shown to have several beneficial medical/therapeutic effects and therefore they are an active area of investigation by the pharmaceutical industry for use as pharmaceutical products for various diseases.

Currently the production of cannabinoids for pharmaceutical or other use is done by chemical synthesis or through the extraction of cannabinoids from plants that are producing these cannabinoids, for example *C. sativa*. There are several drawbacks to the current methods of cannabinoid production. The chemical synthesis of various cannabinoids is a costly process when compared to the extraction of cannabinoids from naturally occurring plants. The chemical synthesis of cannabinoids also involves the use of chemicals that are not environmentally friendly, which can be considered as an additional cost to their production. Furthermore, the synthetic chemical production of various cannabinoids has been classified as less pharmacologically active as those extracted from plants such as *C. sativa*. Although there are drawbacks to chemically synthesized cannabinoids, the benefit of this production method is that the end product is a highly pure single cannabinoid. This level of purity is preferred for pharmaceutical use. The level of purity required by the pharmaceutical industry is reflected by the fact that no plant extract based cannabinoid production has received FDA approval yet and only synthetic compounds have been approved.

In contrast to the synthetic chemical production of cannabinoids, the other method that is currently used to produce cannabinoids is production of cannabinoids in plants that naturally produce these chemicals; the most used plant for this is *C. sativa*. In this method, the plant *C. sativa* is cultivated and during the flowering cycle various cannabinoids are produced naturally by the plant. The plant can be harvested and the cannabinoids can be ingested for pharmaceutical purposes in various methods directly from the plant itself or the cannabinoids can be extracted from the plant. There are multiple methods to extract the cannabinoids from the plant *C. sativa*. All of these methods typically involve placing the plant, *C. sativa* that contains the cannabinoids, into a chemical solution that selectively solubilizes the cannabinoids into this solution. There are various chemical solutions used to do this such as hexane, cold water extraction methods, $CO_2$ extraction methods, and others. This chemical solution, now containing all the different cannabinoids, can then be removed, leaving behind the excess plant material. The cannabinoid containing solution can then be further processed for use.

There are several drawbacks of the natural production and extraction of cannabinoids in plants such as *C. sativa*. Since there are numerous cannabinoids produced by *C. sativa* it is often difficult to reproduce identical cannabinoid profiles in plants using an extraction process. Furthermore, variations in plant growth will lead to different levels of cannabinoids in the plant itself making reproducible extraction difficult. Different cannabinoid profiles will have different pharmaceutical effects which are not desired for a pharmaceutical product. Furthermore, the extraction of cannabinoids from *C. sativa* extracts produces a mixture of cannabinoids and not a highly pure single pharmaceutical compound. Since many cannabinoids are similar in structure it is difficult to purify these mixtures to a high level resulting in cannabinoid contamination of the end product.

There is thus a need to provide an improved method of cannabinoid production.

SUMMARY

This Summary is provided to introduce a selection of concepts in a simplified form that are further described below in the Detailed Description. This Summary is not intended to identify key or essential features of the claimed subject matter, nor is it intended to be used to limit the scope of the claimed subject matter. Other features, details, utilities, and advantages of the claimed subject matter will be apparent from the following written Detailed Description including those aspects illustrated in the accompanying drawings and defined in the appended claims.

According to a first aspect of the present disclosure, there is provided a genetically modified yeast comprising:
(a) one or more GPP producing genes and optionally, one or more GPP pathway genes;
(b) two or more olivetolic acid producing genes;
(c) one or more cannabinoid precursor or cannabinoid producing genes;
(d) one or more Hexanoyl-CoA producing genes, and
(e) at least 5% dry weight of fatty acids or fats.

In certain embodiments, the one or more GPP producing gene comprises at least one of:
a) a mutated farnesyl diphosphate synthase;
b) a mutated *S. cerevisiae* ERG20 comprising a K197E substitution;
c) a double mutated *S. cerevisiae* ERG20 comprising F96W and N127W substitutions;
d) a mutated *Y. lipolytica* ERG20 comprising a K189E substitution;
e) a double mutated *Y. lipolytica* ERG20 comprising F88W and N119W substitutions;
f) a polynucleotide encoding a polypeptide that has at least 70%, 75%, 80%, 85%, 90%, 91%, 92%, 93%, 94%, 95%, 96%, 97%, 98%, 99% or 100% sequence identity to any one of SEQ ID NOS: 1-4;
g) a polypeptide that has at least 70%, 75%, 80%, 85%, 90%, 91%, 92%, 93%, 94%, 95%, 96%, 97%, 98%, 99% or 100% sequence identity to any one of SEQ ID NOS: 1-4; or
h) any combination of (a)-(g).

In certain embodiments, the one or more GPP producing genes is selected from a GPP pathway gene. In certain embodiments, the GPP pathway gene is selected from:
a) a hydroxymethylglutaryl-CoA reductase (HMGR);

b) a truncated hydroxymethylglutaryl-CoA reductase (tHMGR);
c) a polynucleotide encoding a polypeptide that has at least 70%, 75%, 80%, 85%, 90%, 91%, 92%, 93%, 94%, 95%, 96%, 97%, 98%, 99% or 100% sequence identity to any one of SEQ ID NOS: 5-6;
d) a polypeptide that has at least 70%, 75%, 80%, 85%, 90%, 91%, 92%, 93%, 94%, 95%, 96%, 97%, 98%, 99% or 100% sequence identity to any one of SEQ ID NOS: 5-6; or
e) any combination of (a)-(d)

In certain embodiments, the two or more olivetolic acid producing genes comprise: at least one of (a)-(d) and at least one of (e)-(h); wherein (a)-(d) comprise:
a) an olivetol synthase (OLS);
b) a polynucleotide encoding a polypeptide that has at least 70%, 75%, 80%, 85%, 90%, 91%, 92%, 93%, 94%, 95%, 96%, 97%, 98%, 99% or 100% sequence identity to SEQ ID NO: 7;
c) a polypeptide that has at least 70%, 75%, 80%, 85%, 90%, 91%, 92%, 93%, 94%, 95%, 96%, 97%, 98%, 99% or 100% sequence identity to SEQ ID NO: 7; or
d) any combination of (a)-(c);
and wherein (e)-(h) comprise:
e) an olivetolic acid cyclase (OAC);
f) a polynucleotide encoding a polypeptide that has at least 70%, 75%, 80%, 85%, 90%, 91%, 92%, 93%, 94%, 95%, 96%, 97%, 98%, 99% or 100% sequence identity to SEQ ID NO: 8;
g) a polypeptide that has at least 70%, 75%, 80%, 85%, 90%, 91%, 92%, 93%, 94%, 95%, 96%, 97%, 98%, 99% or 100% sequence identity to SEQ ID NO: 8; or
h) any combination of (e)-(g).

In certain embodiments, the one or more cannabinoid precursor or cannabinoid producing genes comprise at least one of:
a) a soluble aromatic prenyltransferase;
b) a cannabigerolic acid synthase (CBGAS);
c) a polynucleotide encoding a polypeptide that has at least 70%, 75%, 80%, 85%, 90%, 91%, 92%, 93%, 94%, 95%, 96%, 97%, 98%, 99% or 100% sequence identity to any one of SEQ ID NOS: 9-12;
d) a polypeptide that has at least 70%, 75%, 80%, 85%, 90%, 91%, 92%, 93%, 94%, 95%, 96%, 97%, 98%, 99% or 10% sequence identity to any one of SEQ ID NOS: 9-12; or
e) any combination of (a)-(e);
alone or in combination with at least one of:
f) a tetrahydrocannabinolic acid synthase (THCAS);
g) a cannabidiolic acid synthase (CBDAS);
h) a cannabichromenic acid synthase (CBCAS);
i) a polynucleotide encoding a polypeptide that has at least 70%, 75%, 80%, 85%, 90%, 91%, 92%, 93%, 94%, 95%, 96%, 97%, 98%, 99% or 100% sequence identity to any one of SEQ ID NOS: 13-15;
j) a polypeptide that has at least 70%, 75%, 80%, 85%, 90%, 91%, 92%, 93%, 94%, 95%, 96%, 97%, 98%, 99% or 100% sequence identity to any one of SEQ ID NOS: 13-15; or
k) any combination of (f)-(j).

In certain embodiments, the soluble aromatic prenyltransferase is NphB from *Streptomyces* sp. strain CL190.

In certain embodiments, the one or more Hexanoyl-CoA producing genes comprise at least one of:
a) a hexanoyl-CoA synthase;
b) HexA and HexB;
c) StcJ and StcK;
d) a mutated FAS1 and a mutated FAS2;
e) a polynucleotide encoding a polypeptide that has at least 70%, 75%, 80%, 85%, 90%, 91%, 92%, 93%, 94%, 95%, 96%, 97%, 98%, 99% or 100% sequence identity to SEQ ID NO: 16 and a polynucleotide encoding a polypeptide that has at least 70%, 75%, 80%, 85%, 90%, 91%, 92%, 93%, 94%, 95%, 96%, 97%, 98%, 99% or 100% sequence identity to SEQ ID NO: 17;
f) a polypeptide that has at least 70%, 75%, 80%, 85%, 90%, 91%, 92%, 93%, 94%, 95%, 96%, 97%, 98%, 99% or 100% sequence identity to SEQ ID NO: 16 and a polypeptide that has at least 70%, 75%, 80%, 85%, 90%, 91%, 92%, 93%, 94%, 95%, 96%, 97%, 98%, 99% or 100% sequence identity to SEQ ID NO: 17;
g) a polynucleotide encoding a polypeptide that has at least 70%, 75%, 80%, 85%, 90%, 91%, 92%, 93%, 94%, 95%, 96%, 97%, 98%, 99% or 100% sequence identity to SEQ ID NO: 18 and a polynucleotide encoding a polypeptide that has at least 70%, 75%, 80%, 85%, 90%, 91%, 92%, 93%, 94%, 95%, 96%, 97%, 98%, 99% or 100% sequence identity to SEQ ID NO: 19;
h) a polypeptide that has at least 70%, 75%, 80%, 85%, 90%, 91%, 92%, 93%, 94%, 95%, 96%, 97%, 98%, 99% or 100% sequence identity to SEQ ID NO: 18 and a polypeptide that has at least 70%, 75%, 80%, 85%, 90%, 91%, 92%, 93%, 94%, 95%, 96%, 97%, 98%, 99% or 100% sequence identity to SEQ ID NO: 19;
i) a polynucleotide encoding a polypeptide that has at least 70%, 75%, 80%, 85%, 90%, 91%, 92%, 93%, 94%, 95%, 96%, 97%, 98%, 99% or 100% sequence identity to SEQ ID NO: 20 and a polynucleotide encoding a polypeptide that has at least 70%, 75%, 80%, 85%, 90%, 91%, 92%, 93%, 94%, 95%, 96%, 97%, 98%, 99% or 100% sequence identity to SEQ ID NO: 21;
j) a polypeptide that has at least 70%, 75%, 80%, 85%, 90%, 91%, 92%, 93%, 94%, 95%, 96%, 97%, 98%, 99% or 100% sequence identity to SEQ ID NO: 20 and a polypeptide that has at least 70%, 75%, 80%, 85%, 90%, 91%, 92%, 93%, 94%, 95%, 96%, 97%, 98%, 99% or 100% sequence identity to SEQ ID NO: 21; or
k) any combination of (a)-(j).

In certain embodiments, the mutated FAS1 and FAS2 genes comprise the genetic modifications selected from: FAS1 I306A and FAS2 G1250S; FAS1 I306A, M1251W and FAS2 G1250S; or FAS1 I306A, R1834K and FAS2 G1250S.

In certain embodiments, the yeast comprises at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, or at least 25% dry weight of fatty acids or fats.

In certain embodiments, the yeast is genetically modified to produce at least 5%, at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, or at least 25% dry weight of fatty acids or fats In certain embodiments, the yeast further comprises genetic modifications that increase the production of fatty acids or fats. In certain embodiments, the genetic modifications that increase the production of fatty acids or fats comprise at least one of:
a) delta-9 stearoyl-CoA desaturase (SCD);
b) a polynucleotide encoding a polypeptide that has at least 70%, 75%, 80%, 85%, 90%, 91%, 92%, 93%, 94%, 95%, 96%, 97%, 98%, 99% or 100% sequence identity to SEQ ID NO: 22;

c) a polypeptide that has at least 70%, 75%, 80%, 85%, 90%, 91%, 92%, 93%, 94%, 95%, 96%, 97%, 98%, 99% or 100% sequence identity to SEQ ID NO: 22;

d) Acetyl-CoA carboxylase (ACC1);

e) a polynucleotide encoding a polypeptide that has at least 70%, 75%, 80%, 85%, 90%, 91%, 92%, 93%, 94%, 95%, 96%, 97%, 98%, 99% or 100% sequence identity to SEQ ID NO: 23;

f) a polypeptide that has at least 70%, 75%, 80%, 85%, 90%, 91%, 92%, 93%, 94%, 95%, 96%, 97%, 98%, 99% or 100% sequence identity to SEQ ID NO: 23 g) Diacylglyceride acyl-transferase (DGA1);

h) a polynucleotide encoding a polypeptide that has at least 70%, 75%, 80%, 85%, 90%, 91%, 92%, 93%, 94%, 95%, 96%, 97%, 98%, 99% or 100% sequence identity to SEQ ID NO: 24;

i) a polypeptide that has at least 70%, 75%, 80%, 85%, 90%, 91%, 92%, 93%, 94%, 95%, 96%, 97%, 98%, 99% or 100% sequence identity to SEQ ID NO: 24; or j) any combination of (a)-(i).

In certain embodiments, the yeast is oleaginous. In certain embodiments, the yeast is selected from the genera *Rhodosporidium, Rhodotorula, Yarrowia, Cryptococcus, Candida, Lipomyces* and *Trichosporon*. The yeast of any one of the preceding claims, wherein the yeast is a *Yarrowia lipolytica*, a *Lipomyces starkey*, a *Rhodosporidium toruloides*, a *Rhodotorula glutinis*, a *Trichosporon fermentans* or a *Cryptococcus curvatus*.

According to a second aspect of the present disclosure, there is provided a method of producing at least one cannabinoid or cannabinoid precursor comprising contacting the yeast of the disclosure with a carbohydrate source under culture conditions and for a time sufficient to produce the at least one cannabinoid or cannabinoid precursor.

In certain embodiments, the at least one cannabinoid or cannabinoid precursor comprises CBGA, THCA, CBDA or CBCA.

According to a second aspect of the present disclosure, there is provided a cannabinoid precursor, cannabinoid or a combination thereof produced using the method of claim 17 or 18.

BRIEF DESCRIPTION OF DRAWINGS

Embodiments of the present disclosure will be discussed with reference to the accompanying drawings wherein.

DESCRIPTION OF EMBODIMENTS

Definitions

Figure 1:
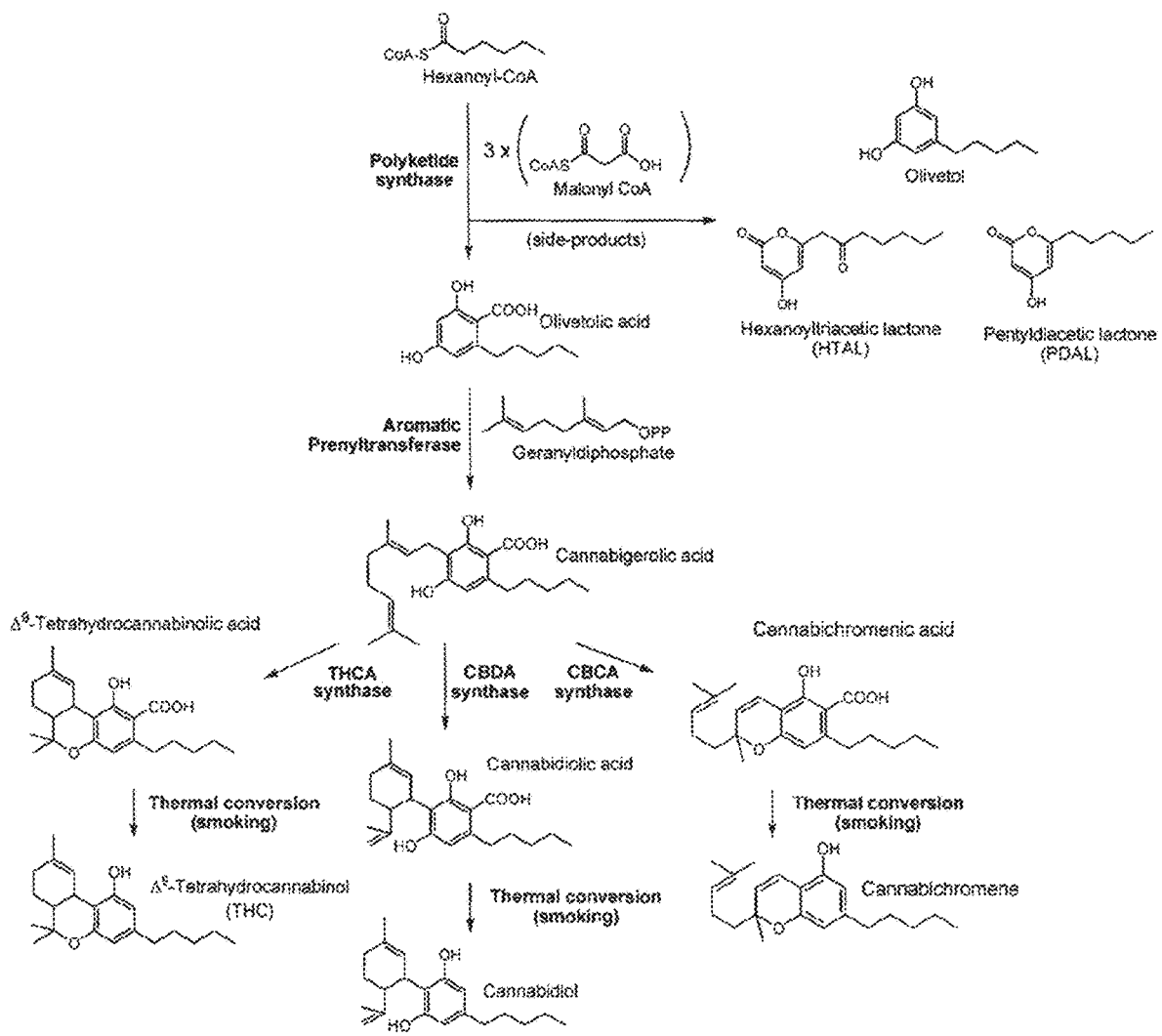
FIG. 1 is diagram of a cannabinoid synthesis pathway.

The following definitions are provided for specific terms which are used in the following written description.

As used in the specification and claims, the singular form "a", "an" and "the" include plural references unless the context clearly dictates otherwise. For example, the term "a cannabinoid precursor" includes a plurality of precursors, including mixtures thereof. The term "a polynucleotide" includes a plurality of polynucleotides.

As used herein, the term "comprising" is intended to mean that the compositions and methods include the recited elements, but do not exclude other elements. "Consisting essentially of" shall mean excluding other elements of any essential significance to the combination. Thus, compositions consisting essentially of produced cannabinoids would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for produced cannabinoids. Embodiments defined by each of these transition terms are within the scope of this invention.

The term "about" or "approximately" means within an acceptable range for the particular value as determined by one of ordinary skill in the art, which will depend in part on how the value is measured or determined, e.g., the limitations of the measurement system. For example, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5 fold, and more preferably within 2 fold, of a value. Unless otherwise stated, the term 'about' means within an acceptable error range for the particular value, such as ±1-20%, preferably ±1-10% and more preferably ±1-5%.

Where a range of values is provided, it is understood that each intervening value, between the upper and lower limit of that range and any other stated or intervening value in that stated range is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either both of those included limits are also included in the invention.

As used herein, the terms "polynucleotide" and "nucleic acid molecule" are used interchangeably to refer to polymeric forms of nucleotides of any length. The polynucleotides may contain deoxyribonucleotides, ribonucleotides, and/or their analogs. Nucleotides may have any three-dimensional structure, and may perform any function, known or unknown. The term "polynucleotide" includes, for example, single-, double-stranded and triple helical molecules, a gene or gene fragment, exons, introns, mRNA, tRNA, rRNA, ribozymes, antisense molecules, cDNA, recombinant polynucleotides, branched polynucleotides, aptamers, plasmids, vectors, isolated DNA of any sequence, isolated RNA of any sequence, nucleic acid probes, and primers. A nucleic acid molecule may also comprise modified nucleic acid molecules (e.g., comprising modified bases, sugars, and/or internucleotide linkers).

As used herein, the term "peptide" refers to a compound of two or more subunit amino acids, amino acid analogs, or peptidomimetics. The subunits may be linked by peptide bonds or by other bonds (e.g., as esters, ethers, and the like).

As used herein, the term "amino acid" refers to either natural and/or unnatural or synthetic amino acids, including glycine and both D or L optical isomers, and amino acid analogs and peptidomimetics. A peptide of three or more amino acids is commonly called an oligopeptide if the peptide chain is short. If the peptide chain is long (e.g., greater than about 10 amino acids), the peptide is commonly called a polypeptide or a protein. While the term "protein" encompasses the term "polypeptide", a "polypeptide" may be a less than full-length protein.

As used herein, "expression" refers to the process by which polynucleotides are transcribed into mRNA and/or translated into peptides, polypeptides, or proteins. If the polynucleotide is derived from genomic DNA, expression may include splicing of the mRNA transcribed from the genomic DNA.

As used herein, "under transcriptional control" or "operably linked" refers to expression (e.g., transcription or translation) of a polynucleotide sequence which is controlled by an appropriate juxtaposition of an expression control element and a coding sequence. In one aspect, a DNA sequence is "operatively linked" to an expression control sequence when the expression control sequence controls and regulates the transcription of that DNA sequence.

As used herein, "coding sequence" is a sequence which is transcribed and translated into a polypeptide when placed under the control of appropriate expression control sequences. The boundaries of a coding sequence are determined by a start codon at the 5' (amino) terminus and a translation stop codon at the 3' (carboxyl) terminus. A coding sequence can include, but is not limited to, a prokaryotic sequence, cDNA from eukaryotic mRNA, a genomic DNA sequence from eukaryotic (e.g., yeast, or mammalian) DNA, and even synthetic DNA sequences. A polyadenylation signal and transcription termination sequence will usually be located 3' to the coding sequence.

As used herein, two coding sequences "correspond" to each other if the sequences or their complementary sequences encode the same amino acid sequences.

As used herein, "signal sequence" denotes the endoplasmic reticulum translocation sequence. This sequence encodes a signal peptide that communicates to a cell to direct a polypeptide to which it is linked (e.g., via a chemical bond) to an endoplasmic reticulum vesicular compartment, to enter an exocytic/endocytic organelle, to be delivered either to a cellular vesicular compartment, the cell surface or to secrete the polypeptide. This signal sequence is sometimes clipped off by the cell in the maturation of a protein. Signal sequences can be found associated with a variety of proteins native to prokaryotes and eukaryotes.

As used herein, "hybridization" refers to a reaction in which one or more polynucleotides react to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. A hybridization reaction may constitute a step in a more extensive process, such as the initiation of a PCR reaction, or the enzymatic cleavage of a polynucleotide by a ribozyme.

As used herein, a polynucleotide or polynucleotide region (or a polypeptide or polypeptide region) which has a certain percentage (for example, at least about 50%, at least about 60%, at least about 70%, at least about 80%, at least about 85%, at least about 90%, at least about 95%, at least about 99%) of "sequence identity" to another sequence means that, when maximally aligned, using software programs routine in the art, that percentage of bases (or amino acids) are the same in comparing the two sequences.

Two sequences are "substantially homologous" or "substantially similar" when at least about 50%, at least about 60%, at least about 70%, at least about 75%, and preferably at least about 80%, and most preferably at least about 90 or 95% of the nucleotides match over the defined length of the DNA sequences. Similarly, two polypeptide sequences are "substantially homologous" or "substantially similar" when at least about 50%, at least about 60%, at least about 66%, at least about 70%, at least about 75%, and preferably at least about 80%, and most preferably at least about 90 or 95% of the amino acid residues of the polypeptide match over a defined length of the polypeptide sequence. Sequences that are substantially homologous can be identified by comparing the sequences using standard software available in sequence data banks. Substantially homologous nucleic acid sequences also can be identified in a Southern hybridization experiment under, for example, stringent conditions as defined for that particular system. Defining appropriate hybridization conditions is within the skill of the art. For example, stringent conditions can be: hybridization at 5×SSC and 50% formamide at 42° C., and washing at 0.1×SSC and 0.1% sodium dodecyl sulfate at 60° C. Further examples of stringent hybridization conditions include: incubation temperatures of about 25 degrees C. to about 37 degrees C.; hybridization buffer concentrations of about 6×SSC to about 10×SSC; formamide concentrations of about 0% to about 25%; and wash solutions of about 6×SSC. Examples of moderate hybridization conditions include: incubation temperatures of about 40 degrees C. to about 50 degrees C.; buffer concentrations of about 9×SSC to about 2×SSC; formamide concentrations of about 30% to about 50%; and wash solutions of about 5×SSC to about 2×SSC. Examples of high stringency conditions include: incubation temperatures of about 55 degrees C. to about 68 degrees C.; buffer concentrations of about 1×SSC to about 0.1×SSC; formamide concentrations of about 55% to about 75%; and wash solutions of about 1×SSC, 0.1×SSC, or deionized water. In general, hybridization incubation times are from 5 minutes to 24 hours, with 1, 2, or more washing steps, and wash incubation times are about 1, 2, or 15 minutes. SSC is 0.15 M NaCl and 15 mM citrate buffer. It is understood that equivalents of SSC using other buffer systems can be employed. Similarity can be verified by sequencing, but preferably, is also or alternatively, verified by function (e.g., ability to traffic to an endosomal compartment, and the like), using assays suitable for the particular domain in question.

The terms "percent (%) sequence similarity", "percent (%) sequence identity", and the like, generally refer to the degree of identity or correspondence between different nucleotide sequences of nucleic acid molecules or amino acid sequences of polypeptides that may or may not share a common evolutionary origin (see Reeck et al., supra). Sequence identity can be determined using any of a number of publicly available sequence comparison algorithms, such as BLAST, FASTA, DNA Strider, GCG (Genetics Computer Group, Program Manual for the GCG Package, Version 7, Madison, Wis.), etc.

To determine the percent identity between two amino acid sequences or two nucleic acid molecules, the sequences are aligned for optimal comparison purposes. The percent identity between the two sequences is a function of the number of identical positions shared by the sequences (i.e., percent identity=number of identical positions/total number of positions (e.g., overlapping positions)×100). In one embodiment, the two sequences are, or are about, of the same length. The percent identity between two sequences can be determined using techniques similar to those described below, with or without allowing gaps. In calculating percent sequence identity, typically exact matches are counted.

The determination of percent identity between two sequences can be accomplished using a mathematical algorithm. A non-limiting example of a mathematical algorithm utilized for the comparison of two sequences is the algorithm of Karlin and Altschul, Proc. Natl. Acad. Sci. USA 1990, 87:2264, modified as in Karlin and Altschul, Proc. Natl. Acad. Sci. USA 1993, 90:5873-5877. Such an algorithm is incorporated into the NBLAST and XBLAST programs of Altschul et al, J. Mol. Biol. 1990; 215: 403. BLAST nucleotide searches can be performed with the NBLAST program, score=100, wordlength=12, to obtain nucleotide sequences homologous to sequences of the invention. BLAST protein searches can be performed with the XBLAST program, score=50, wordlength=3, to obtain amino acid sequences homologous to protein sequences of the invention. To obtain gapped alignments for comparison purposes, Gapped BLAST can be utilized as described in Altschul et al, Nucleic Acids Res. 1997, 25:3389. Alternatively, PSI-Blast can be used to perform an iterated search that detects distant relationship between molecules. See Altschul et al. (1997) supra. When utilizing BLAST, Gapped BLAST, and PSI-Blast programs, the default parameters of the respective programs (e.g., XBLAST and NBLAST) can be used.

Another non-limiting example of a mathematical algorithm utilized for the comparison of sequences is the algorithm of Myers and Miller, CABIOS 1988; 4:11-17. Such an algorithm is incorporated into the ALIGN program (version 2.0), which is part of the GCG sequence alignment software package. When utilizing the ALIGN program for comparing amino acid sequences, a PAM120 weight residue table, a gap length penalty of 12, and a gap penalty of 4 can be used.

In a preferred embodiment, the percent identity between two amino acid sequences is determined using the algorithm of Needleman and Wunsch (J. Mol. Biol. 1970, 48:444-453), which has been incorporated into the GAP program in the GCG software package (Accelrys, Burlington, Mass.; available at accelrys.com on the WorldWideWeb), using either a Blossum 62 matrix or a PAM250 matrix, a gap weight of 16, 14, 12, 10, 8, 6, or 4, and a length weight of 1, 2, 3, 4, 5, or 6. In yet another preferred embodiment, the percent identity between two nucleotide sequences is determined using the GAP program in the GCG software package using a NWSgapdna.CMP matrix, a gap weight of 40, 50, 60, 70, or 80, and a length weight of 1, 2, 3, 4, 5, or 6. A particularly preferred set of parameters (and the one that can be used if the practitioner is uncertain about what parameters should be applied to determine if a molecule is a sequence identity or homology limitation of the invention) is using a Blossum 62 scoring matrix with a gap open penalty of 12, a gap extend penalty of 4, and a frameshift gap penalty of 5.

Another non-limiting example of how percent identity can be determined is by using software programs such as those described in Current Protocols In Molecular Biology (F. M. Ausubel et al., eds., 1987) Supplement 30, section 7.7.18, Table 7.7.1. Preferably, default parameters are used for alignment. A preferred alignment program is BLAST, using default parameters. In particular, preferred programs are BLASTN and BLASTP, using the following default parameters: Genetic code=standard; filter=none; strand=both; cut-off=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR.

Statistical analysis of the properties described herein may be carried out by standard tests, for example, t-tests, ANOVA, or Chi squared tests. Typically, statistical significance will be measured to a level of $p=0.05$ (5%), more preferably $p=0.01$, $p=0.001$, $p=0.0001$, $p=0.000001$ "Conservatively modified variants" of domain sequences also can be provided. With respect to particular nucleic acid sequences, conservatively modified variants refer to those nucleic acids which encode identical or essentially identical amino acid sequences, or where the nucleic acid does not encode an amino acid sequence, to essentially identical sequences. Specifically, degenerate codon substitutions can be achieved by generating sequences in which the third position of one or more selected (or all) codons is substituted with mixed-base and/or deoxyinosine residues (Batzer, et al., 1991, Nucleic Acid Res. 19: 5081; Ohtsuka, et al., 1985, J. Biol. Chem. 260: 2605-2608; Rossolini et al., 1994, Mol. Cell. Probes 8: 91-98).

The term "biologically active fragment", "biologically active form", "biologically active equivalent" of and "functional derivative" of a wild-type protein, possesses a biological activity that is at least substantially equal (e.g., not significantly different from) the biological activity of the wild type protein as measured using an assay suitable for detecting the activity.

As used herein, the term "isolated" or "purified" means separated (or substantially free) from constituents, cellular and otherwise, in which the polynucleotide, peptide, polypeptide, protein, antibody, or fragments thereof, are normally associated with in nature. As is apparent to those of skill in the art, a non-naturally occurring polynucleotide, peptide, polypeptide, protein, antibody, or fragments thereof, does not require "isolation" to distinguish it from its naturally occurring counterpart. By substantially free or substantially purified, it is meant at least 50% of the population, preferably at least 70%, more preferably at least 80%, and even more preferably at least 900%, are free of the components with which they are associated in nature.

A cell has been "transformed", "transduced", or "transfected" when nucleic acids have been introduced inside the cell. Transforming DNA may or may not be integrated (covalently linked) with chromosomal DNA making up the genome of the cell. For example, the polynucleotide may be maintained on an episomal element, such as a plasmid or a stably transformed cell is one in which the polynucleotide has become integrated into a chromosome so that it is inherited by daughter cells through chromosome replication. This stability is demonstrated by the ability of the cell to establish cell lines or clones comprised of a population of daughter cells containing the transformed polynucleotide. A "clone" is a population of cells derived from a single cell or common ancestor by mitosis. A "cell line" is a clone of a primary cell that is capable of stable growth in vitro for many generations (e.g., at least about 10).

A "vector" includes plasmids and viruses and any DNA or RNA molecule, whether self-replicating or not, which can be used to transform or transfect a cell.

As used herein, a "genetic modification" refers to any addition, deletion or disruption to a cell's normal nucleotides and/or additional of heterologous sequences into the yeast. Any method which can achieve the genetic modification are within the spirit and scope of this invention. Art recognized methods include viral mediated gene transfer, liposome mediated transfer, transformation, transfection and transduction The practice of the present invention employs, unless otherwise indicated, conventional molecular biology, microbiology, and recombinant DNA techniques within the skill of the art. Such techniques are explained fully in the literature. See, e.g., Maniatis, Fritsch & Sambrook, In Molecular Cloning: A Laboratory Manual (1982); DNA Cloning: A Practical Approach, Volumes I and II (D. N. Glover, ed., 1985); Oligonucleotide Synthesis (M. J. Gait, ed., 1984); Nucleic Acid Hybridization (B. D. Hames & S. J. Higgins, eds., 1985); Transcription and Translation (B. D. Hames & S. I. Higgins, eds., 1984); Animal Cell Culture (R. I. Freshney, ed., 1986); Immobilized Cells and Enzymes (IRL Press, 1986); B. Perbal, A Practical Guide to Molecular Cloning (1984).

Unless defined otherwise, all technical and scientific terms used herein have the same meaning as commonly understood by one of ordinary skill in the art to which this invention belongs. All publications mentioned herein are incorporated by reference for the purpose of describing and disclosing devices, formulations and methodologies that may be used in connection with the presently described invention.

Genetically Modified Yeast Strains

Disclosed herein are genetically modified yeasts comprising one or more genetic modifications that result in the production of at least one cannabinoid or cannabinoid precursor and methods for their creation. The disclosed yeast may produce various cannabinoids from a simple sugar source, for example, where the main carbon source available to the yeast is a sugar (glucose, galactose, fructose, sucrose, honey, molasses, raw sugar, etc.). Genetic engineering of the yeast involves inserting various genes that produce the appropriate enzymes and/or altering the natural metabolic pathway in the yeast to achieve the production of a desired compound. Through genetic engineering of yeast, these metabolic pathways can be introduced into these yeast and the same metabolic products that are produced in the plant C. sativa can be produced by the yeast. The benefit of this method is that once the yeast is engineered, the production of the cannabinoid is low cost and reliable, and only a specific cannabinoid is produced or a subset is produced, depending on the organism and the genetic manipulation. The purification of the cannabinoid is straightforward since there is only a single cannabinoid or a selected few cannabinoids present in the yeast. The process is a sustainable process which is more environmentally friendly than synthetic production.

A high level biosynthetic route for the production of Cannabinoids is shown in FIG. 1. The pathway begins with the conversion of Hexanoyl-CoA to olivetolic acid (OA), a polyketide, by the action of polyketide synthase (OLS) and olivtolic acid cyclase (OAC). OA is then prenylated with the monoterpene geranyl diphosphate (GPP) to cannabigerolic acid (CBGA) by an aromatic prenyltransferase. Finally, cannabidiolic acid (CBDA) is produced by cyclizing CBGA via cannabidiolic acid synthase (CBDAS), or tettrahydrocannabinolic acid (THCA) is produced from CBGA by tetrahydrocannabinolic acid synthase (THCAS), or cannabichromenic acid (CBCA) is produced from CBGA by cannabichromenic acid synthase (CBCAS).

Figure 2:
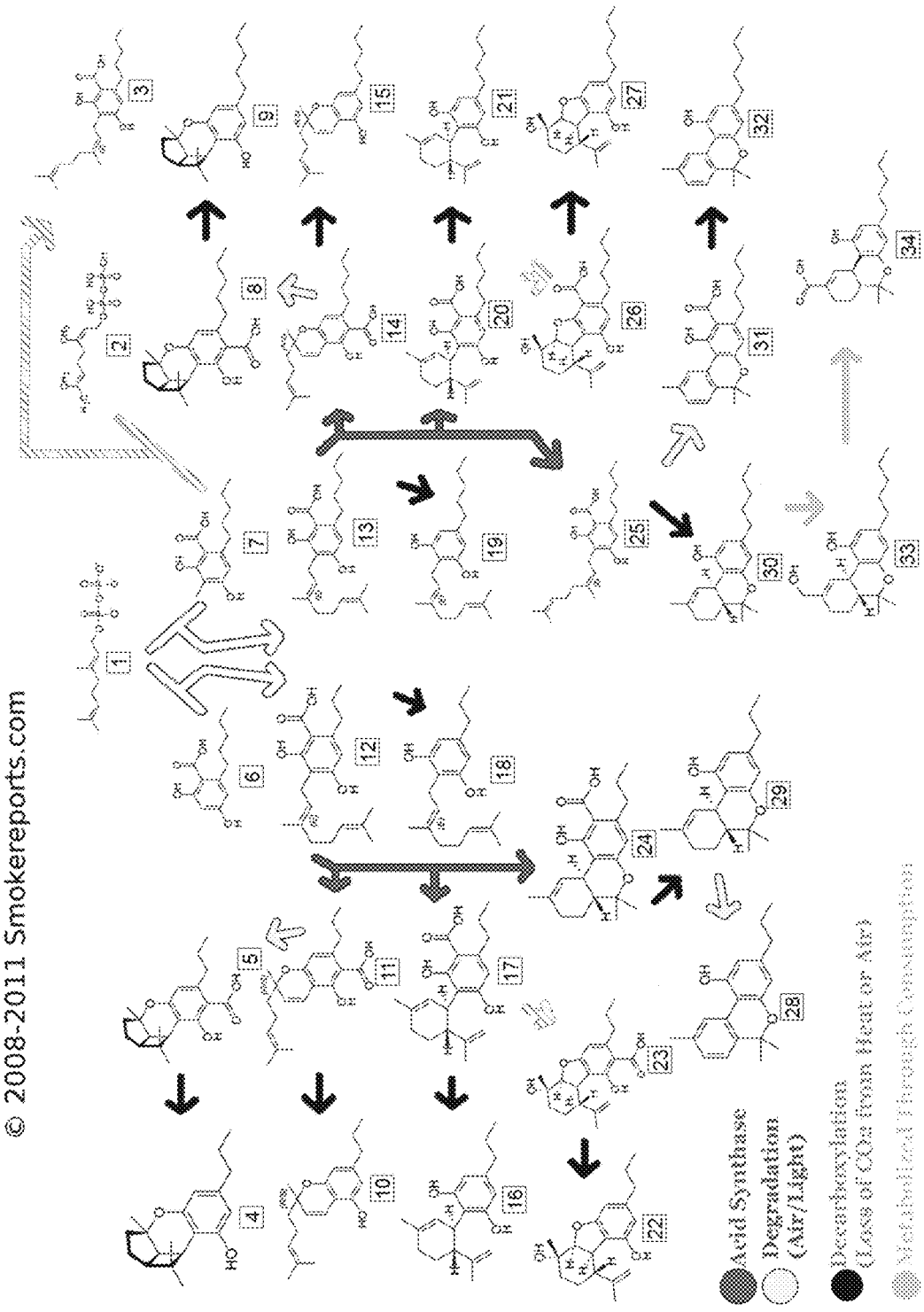
FIG. 2 is diagram of a cannabinoid synthesis pathway including nonenzymatic steps.

The production pathways for non-enzymatic modifications are demonstrated on FIG. 2.

In the past, there have been multiple attempts to produce cannabinoids in yeasts. At present, no one has been able reach a reasonable price for production due to extremely low yield. We have identified how the yield can be increased.

We have established a link between oil production in yeast and theoretical maximum cannabinoid production. Based on this unexpected link: (1) instead of producing cannabinoids in traditional yeasts, we propose using yeast having at least 5% dry weight of fatty acids or fats, such as oily yeasts, for example, Y. lipolytica; (2) we also propose making additional genetic modifications that will increase oil production level in the engineered yeast; (3) add additional genes from the cannabinoid production pathway in combination with genes from alternative pathways that produce cannabinoid intermediates, such as for example NphB; (4) increase production of GPP by, for example, genetically mutating ERG20 and/or by using equivalent genes from alternative pathways; (5) increase production of compounds from fatty acid pathway for use in the cannabinoid production pathway, for example, increase the production of malonyl-CoA by overexpressing ACC1.

Cannabinoids have a limited solubility in water solutions. Yet, they have a high solubility in hydrophobic liquids like lipids, oils or fats. If hydrophobic media is limited or completely removed than CBGA will not be solubilized and will have limited availability to following cannabinoid synthetases. As an example, in the paper (Zirpel et al. 2015) it was shown that purified THCA synthase is almost unable to convert CBGA into THCA. In the same paper the authors demonstrated that unpurified yeast lysate converts CBGA much more efficiently. The authors also demonstrated that CBGA was dissolved in the lipid fraction. In another paper (Lange et al. 2016) the authors made the next step in improving a cell free process. They used a two-phase reaction with an organic, hydrophobic phase and aquatic phase. The authors demonstrated a high yield of THCA from CBGA. They found that CBGA was dissolved in organic phase. They also demonstrated that THCA was moved back to the organic phase. We can therefore conclude that a hydrophobic phase is required for successful synthesis and that cannabinoids are mostly present in the organic phase.

Figure 3:
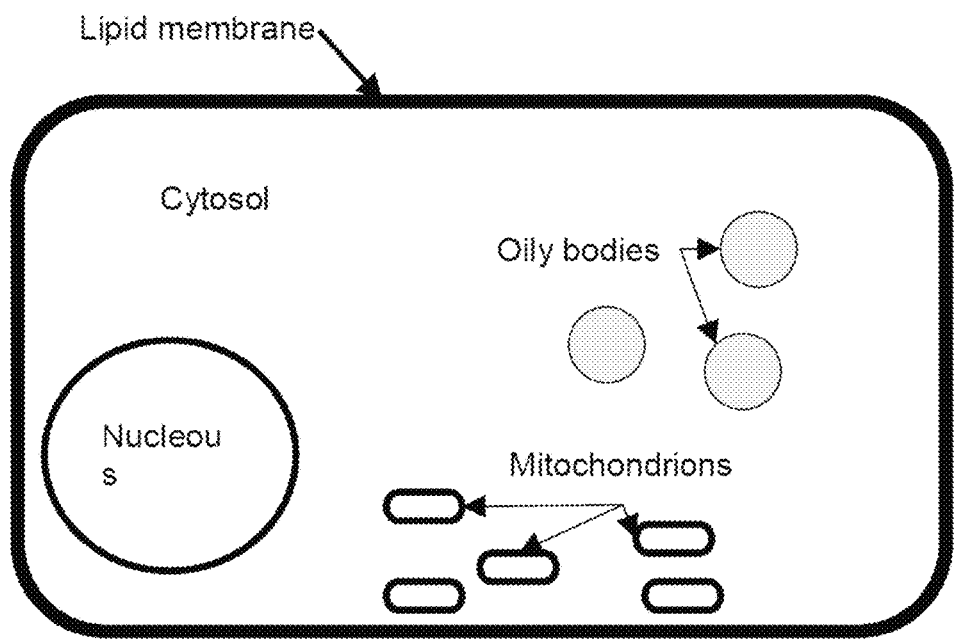
FIG. 3 is a high level scheme of yeast cell organisation.

A high level scheme of a yeast cell is shown in FIG. 3. The main mass of lipids in traditional yeasts like S. cerevisiae, K. phaffii, K. marxianus are deposited in the lipid membrane. These types of yeast almost have no oily bodies. In such a case, any cannabinoids that are produced will be dissolved in this membrane. Too many cannabinoids will destabilize a membrane which will cause cell death. It was reported that in the best conditions, with high sugar content and without nitrogen supply, these yeasts can have a maximum of 2-3% dry weight of oils (i.e. fats and fatty acids).

Figure 4:
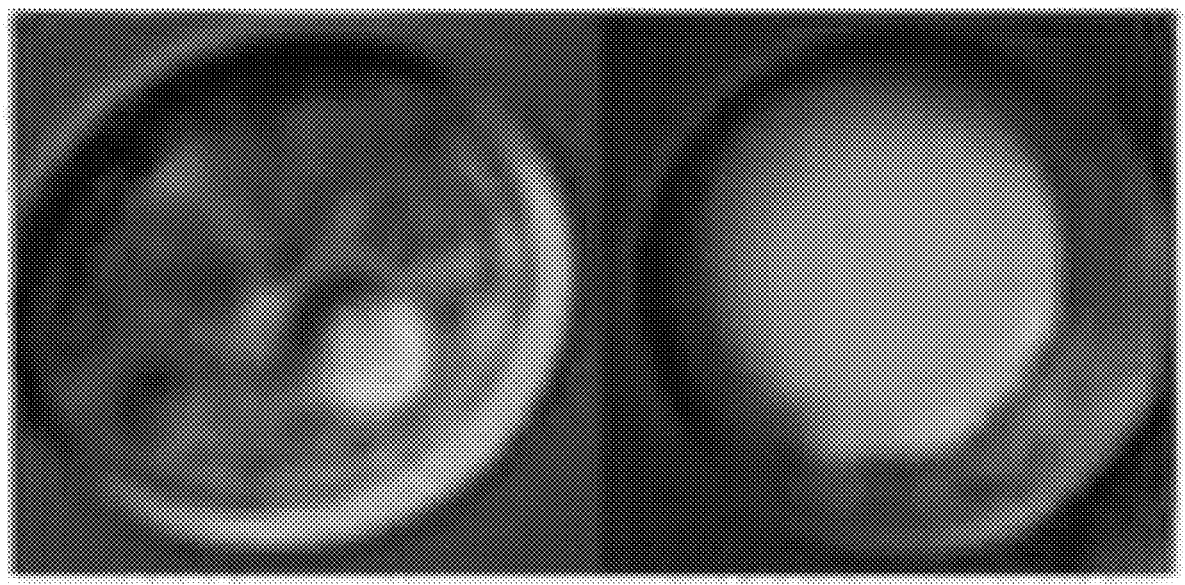
FIG. 4. *Y. Lipolytica* oil content before and after modification. The pale circular regions indicate oils on the picture (see arrows). The ad9 mutant (right image) accumulates more oil than wild type *Yarrowia lipolytica* (left image).

There are several non-traditional yeasts, like Y. lipolytica. The natural form of Y. lipolytica can have up to 17% dry weight of oils. The main mass of oil is located in oily bodies. Cannabinoids dissolved in such bodies will not cause membrane instability. As a result, Y. lipolytica can have a much higher cannabinoid production level. Several works have demonstrated modifications for Y. lipolytica which can bring the lipid content above 80% of dry mass (Qiao et al. 2015). FIG. 4. is taken from Qiao et al. 2015 and demonstrates the difference in oil content in modified vs wild type Y. lipolytica. A minimal set of 3 gene modifications were used.

Therefore, we propose that cannabinoids can be produced to some percentage of the oil content in yeast. This gives a correlation—more oil means more cannabinoid production.

A review paper (Ângela et al. 2017) analysed different types of yeast as a potential producers for cannabinoids. TABLE 1 is adapted from the summary table in Ângela et al. 2017, in which the authors compared 4 yeasts types by different parameters. Yet, they completely ignored oil content, theoretical maximal limit of production and minimal cost of goods for production. The far right two columns show maximum oil amount as a percentage of dry weight, and the production cost if there is only 1% of cannabinoid in the oil. The bottom row shows an embodiment of a modified Yarrowia lipolytica of the present disclosure. Finally, the authors in Ângela et al. 2017 considered that acetyl-CoA pool engineering had optimization potential; +. However, we have found that YL has large concentration of acetyl-CoA without modifications.

Therefore, we are proposing to use oily yeasts as a backbone for production.

TABLE 1

COMPARISON OF DIFFERENT MICROBIAL EXPRESSION HOSTS REGARDING THEIR CAPACITY OF HETEROOGOUS CANNABINOID BIOSYNTHESIS

|  | Genetic tools available | Strains, promoters, vectors | plant protein expression capacity | Post-translational modifications | GPP engineering | Hexanoic acid engineering | acetyl-CoA pool engineering | Maximal oil amount % of dry weight | Production cost with only 1% of cannabinoids from oils |
|---|---|---|---|---|---|---|---|---|---|
| *E. coli* | +++ | +++ | + | − | ++ | + | + | 2% | $12.50 |
| *S. cerevisiae* | +++ | +++ | ++ | ++ | +++ | ++ | +++ | 2% | $12.50 |
| *P. Pastoris* | + | ++ | +++ | ++ | + | ++ |  | 3% | $8.33 |
| *K. marxianus* | ++ | + | ++ | ++ |  |  |  | 3% | $8.33 |
| *Y. Lipolica* | + | + | ++ | ++ | + | ++ | +, YL has large concentration of ac-CoA without modifications | 17% | $1.47 |
| Y. L. modified | + | + | ++ | ++ | + | ++ | +, YL has large concentration of ac-CoA without modifications | 80% | $0.31 |

* maximal oil % means how much oils can be produced in a best cultivation conditions. % calculated from dried mass.
Table 1 adapted from Carvalho, Ângela, et al. "Designing microorganisms for heterologous biosynthesis of cannabinoids." FEMS yeast research 17.4 (2017). 1. +++, many publications available, well established; ++, publications available, optimization potential; +, first publications available, not yet established/not working; −, not possible; 'empty', not yet described.

The pathway of cannabinoids is described in multiple publications. We can use all suggested modification from recent papers (Zirpel et al. 2017; Poulos and Farnia 2016; Ângela et al. 2017) and others. We can use modifications for a biosynthesis pathway like replacing CBGA synthase by NphB gene which already described (Zirpel et al. 2017).

As described in multiple papers for cannabinoid and terpenes production we also propose mutations that will increase production of GPP. For example, one way will use a mutated ERG20 gene to increase amount of GPP which is required in the cannabinoid synthesis pathway (Zhao et al. 2016; ZHUANG n.d.; Kampranis and Makris 2012).

There are a few key differences between plant polyketide and terpene biosynthesis when compared to yeast. Yeast does not contain many of the enzymes and fatty acids required for the production of THCA. Moreover, yeast do not express high levels of geranyl diphosphate (GPP), a chemical required for the production of cannabigerolic acid, the precursor to THCA. Yet, through genetic engineering many of the required enzymes can be added and the production of GPP can be increased. In order to add the required enzymes for cannabinoid production in yeast, the inventors have transformed yeast with the essential genes in the cannabinoid biosynthetic pathway.

Accordingly, in a first aspect, there is provided a genetically modified yeast comprising: (a) one or more GPP producing genes and optionally, one or more GPP pathway genes; (b) two or more olivetolic acid producing genes; (c) one or more cannabinoid precursor or cannabinoid producing genes; (d) one or more Hexanoyl-CoA producing genes, and (e) at least 5% dry weight of fatty acids or fats.

The disclosed genes may be endogenous or heterologous and include homologs that retain the function of the disclosed genes. As would be appreciated by the person skilled in the art, homologs could be identified through nucleotide or amino acid sequence alignments. In certain embodiments, the genetically modified yeast comprises: polynucleotides encoding polypeptides that are at least 70%, at least 75%, at least 80%, at least 85%, at least 900%, at least 95%, at least 96%, at least 97%, at least 98%, at least 99%, or 100% identical to the disclosed SEQ ID NOS; polypeptides that are at least 70%, at least 75%, at least 80% at least 85%, at least 900%, at least 95%, at least 96%, at least 97%, at least 98%, at least 99%, or 100% identical to the disclosed SEQ ID NOS; or both. Variants of the common cannabinoid synthesising proteins, such as CBDAS, retain the ability to cyclize CBGA to produce CBDA. For example, a variant common cannabinoid synthesising protein, such as CBDAS, must retain the ability to cyclize CBGA to produce CBDA with at least about 50%, at least about 60%, at least about 70%, at least about 80%, at least about 900%, or at least about 100% efficacy compared to the original sequence. In preferred embodiments, a variant common cannabinoid protein, such as CBDAS, has improved activity over the sequence from which it is derived in that the improved variant common cannabinoid protein has more than 110%, 120%, 130%, 140%, or and 150% improved activity in cyclizing CBGA to produce CBDA, as compared to the sequence from which the improved variant is derived.

The disclosed genes may be under the control of any suitable promoter. Many native promoters are available, for example, for *Y. lipolytica*, native promoters are available from the genes for translational elongation factor EF-1 alpha, acyl-CoA: diacylglycerol acyltransferase, acetyl-CoA-carboxylase 1, ATP citrate lyase 2, fatty acid synthase subunit beta, fatty acid synthase subunit alpha, isocitrate lyase 1, POX4 fatty-acyl coenzyme A oxidase, ZWF1 glucose-6-phosphate dehydrogenase, gytosolic NADP-specific isocitrate dehydrogenase, glyceraldehyde 3-phosphate dehydrogenase and the TEF intron (Wong et al. 2017). Any suitable terminator may be used. Short synthetic terminators are particularly suitable and are readily available, see for example, MacPherson et al. 2016.

As would be appreciated by the person skilled in the art, increased expression of a gene may provide increased the activity of the gene product. In certain embodiments, overexpression of a gene can increase the activity of the gene product in yeast by about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 105%, about 110%, about 115%, about 120%, about 125%, about 130%, about 135%, about 140%, about 145%, about 150%, about 155%, about 160%, about 165%, about 170%, about 175%, about 180%, about 185%, about 190%, about 95%, or about 200%.

As described above, in certain embodiments, the yeast comprises at least 5% dry weight of fatty acids or fats. Accordingly, the yeast may be oleaginous. Any oleaginous yeast may be suitable, however, particularly suitable yeast may be selected from the genera *Rhodosporidium, Rhodotorula, Yarrowia, Cryptococcus, Candida, Lipomyces* and *Trichosporon*. In certain embodiments, the yeast is a *Yarrowia lipolytica*, a *Lipomyces starkey*, a *Rhodosporidium toruloides*, a *Rhodotorula glutinis*, a *Trichosporon fermentans* or a *Cryptococcus curvatus*. The yeast may be naturally oleaginous. Accordingly, in certain embodiments, the yeast comprises at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 30%, at least 35%, at least 40%, at least 45%, at least 50%, at least 55%, at least 60%, at least 65%, at least 70%, at least 75% or at least 80% dry weight of fatty acids or fats. The yeast may also be genetically modified to accumulate or produce more fatty acids or fats. Accordingly, in certain embodiments, the yeast is genetically modified to produce at least 5%, at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 30%, at least 35%, at least 40%, at least 45%, at least 50%, at least 55%, at least 60%, at least 65%, at least 70%, at least 75% or at least 80% dry weight of fatty acids or fats.

GPP Producing Genes

GPP may be produced in yeast by expressing mutated farnesyl diphosphate synthase. Normally in yeast, the farnesyl diphosphate synthase ERG20 condenses isopentenyl diphosphate (IPP) and dimethylallyl diphosphate (DMAP) to provide geranyl pyrophosphate (GPP) and then condenses two molecules of GPP to provide feranyl pyrophosphate (FPP). However, only a low level of GPP remains as ERG20 converts most of the GPP to FPP. More GPP is required for the commercial scale production of cannabinoids. Accordingly, mutated ERG20 that has a reduced or inability to produce FPP, may be used to increase the production of GPP. Two sets of mutations have been identified in *S. cerevisiae* that increase GPP production. The first mutation is a substitution of K197E and the second is a double substitution of F96W and N127W. As would be readily appreciated by the person skilled in the art, due to the high homology between ERG20 from *S. cerevisiae* and ERG20 from *Y. lypolytica*, equivalent mutations may be introduced into ERG20 from *Y. lipolytica*. In *Y. lipolytica* the first mutation is a substitution of K189E and the second is a double substitution of F88W and N119W. Introducing *Y. lipolytica* ERG20 (K189E) increases the production of GPP but growth is little bit slower compared to wild type yeast. Introducing *Y. lipolytica* ERG20 (F88W and N119W) produces fast growing clones with a high level of GPP. The sequences for the *Y. lipolytica* and *S. cerevisiae* genes are shown herein, however the skilled person would understand that homologous genes may also be suitable. Examples of ERG20 homologs as shown in Table 2. Accordingly, in certain embodiments, the one or more GPP producing genes comprise: a mutated farnesyl diphosphate synthase; a mutated *S. cerevisiae* ERG20 comprising a K197E substitution; a double mutated *S. cerevisiae* ERG20 comprising F96W and N127W substitutions; a mutated *Y. lipolytica* ERG20 comprising a K189E substitution; or a double mutated *Y. lipolytica* ERG20 comprising F88W and N119W substitutions; or a combination thereof. For the SEQ IDS described herein, mutations are shown with a solid underline. In certain embodiments, *S. cerevisiae* ERG20 (K197E) comprises a polynucleotide encoding a polypeptide that has at least 70%, 75%, 80%, 85%, 90%, 91%, 92%, 93%, 94%, 95%, 96%, 97%, 98%, 99% or 100% sequence identity to SEQ ID NO: 1. In certain embodiments, *S. cerevisiae* ERG20 (K197E) comprises a polypeptide that has at least 70%, 75%, 80%, 85%, 90%, 91%, 92%, 93%, 94%, 95%, 96%, 97%, 98%, 99% or 100% sequence identity to SEQ ID NO: 1. In certain embodiments, *S. cerevisiae* ERG20 (F96W and N127W) comprises a polynucleotide encoding a polypeptide that has at least 70%, 75%, 80%, 85%, 90%, 91%, 92%, 93%, 94%, 95%, 96%, 97%, 98%, 99% or 100% sequence identity to SEQ ID NO: 2. In certain embodiments, *S. cerevisiae* ERG20 (F96W and N127W) comprises a polypeptide that has at least 70%, 75%, 80%, 85%, 90%, 91%, 92%, 93%, 94%, 95%, 96%, 97%, 98%, 99% or 100% sequence identity to SEQ ID NO: 2. The equivalent *Y. lipolytica* amino acid sequences are shown in SEQ ID NOS: 3 and 4. In certain embodiments, *Y. lipolytica* ERG20 (K189E) comprises a polynucleotide encoding a polypeptide that has at least 70%, 75%, 80%, 85%, 90%, 91%, 92%, 93%, 94%, 95%, 96%, 97%, 98%, 99% or 100% sequence identity to SEQ ID NO: 3. In certain embodiments, *Y. lipolytica* ERG20 (K189E) comprises a polypeptide that has at least 70%, 75%, 80%, 85%, 90%, 91%, 92%, 93%, 94%, 95%, 96%, 97%, 98%, 99% or 100% sequence identity to SEQ ID NO: 3. In certain embodiments, *Y. lipolytica* ERG20 (F88W and N119W) comprises a polynucleotide encoding a polypeptide that has at least 70%, 75%, 80%, 85%, 90%, 91%, 92%, 93%, 94%, 95%, 96%, 97%, 98%, 99% or 100% sequence identity to SEQ ID NO: 4. In certain embodiments, *Y. lipolytica* ERG20 (F88W and N119W) comprises a polypeptide that has at least 70%, 75%, 80%, 85%, 90%, 91%, 92%, 93%, 94%, 95%, 96%, 97%, 98%, 99% or 100% sequence identity to SEQ ID NO: 4.

Variants of the GPP proteins, such as ERG20, retain the ability to, for example, condense isopentenyl diphosphate (IPP) and dimethylallyl diphosphate (DMAP) to geranyl pyrophosphate (GPP) and yet have reduced GPP to FPP activity. For example, a variant of a GPP protein, such as ERG20, retains the ability to condense isopentenyl diphosphate (IPP) and dimethylallyl diphosphate (DMAP) to geranyl pyrophosphate (GPP) with at least about at least about 80%, at least about 900%, or at least about 100% efficacy compared to the original sequence, while the ability to condense GPP to FPP is reduced by at least 10%, 20%, 30%, 40%, 50%, 60%, 70%, 80%, 90% or 100% (null mutation) as compared to the sequence from which it is derived.

ERG20 (K197E)
SEQ ID NO: 1
MASEKEIRRERFLNVFPKLVEELNASLLAYGMPKEACDWYAHSLNYNT
PGGKLNRGLSVVDTYAILSNKTVEQLGQEEYEKVAILGWCIELLQAYF
LVADDMMDKSITRRGQPCWYKVPEVGEIAINDAFMLEAAIYKLLKSHF
RNEKYYIDITELFHEVTFQTELGQLMDLITAPEDKVDLSKFSLKKHSF
IVTFETAYYSFYLPVALAMYVAGITDEKDLKQARDVLIPLGEYFQIQD
DYLDCFGTPEQIGKIGTDIQDNKCSWVINKALELASAEQRKTLDENYG
KKDSVAEAKCKKIFNDLKIEQLYHEYEESIAKDLKAKISQVDESRGFK
ADVLTAFLNKVYKRSK*

ERG20 (F96W and N127W)
SEQ ID NO: 2
MASEKEIRRERFLNVFPKLVEELNASLLAYGMPKEACDWYAHSLNYNT
PGGKLNRGLSVVDTYAILSNKTVEQLGQEEYEKVAILGWCIELLQAYW
LVADDMMDKSITRRGQPCWYKVPEVGEIAIWDAFMLEAAIYKLLKSHF
RNEKYYIDITELFHEVTFQTELGQLMDLITAPEDKVDLSKFSLKKHSF
IVTFKTAYYSFYLPVALAMYVAGITDEKDLKQARDVLIPLGEYFQIQD
DYLDCFGTPEQIGKIGTDIQDNKCSWVINKALELASAEQRKTLDENYG
KKDSVAEAKCKKIFNDLKIEQLYHEYEESIAKDLKAKISQVDESRGFK
ADVLTAFLNKVYKRSK*

Y. lipolytica ERG20 (K189E)
SEQ ID NO: 3
MSKAKFESVFPRISEELVQLLRDEGLPQDAVQWFSDSLQYNCVGGKLN
RGLSVVDTYQLLTGKKELDDEEYYRLALLGWLIELLQAFFLVSDDIMD
ESKTRRGQPCWYLKPKVGMIAINDAFMLESGIYILLKKHFRQEKYYID
LVELFHDISFKTELGQLVDLLTAPEDEVDLNRFSLDKHSFIVRYETAY
YSFYLPVVLAMYVAGITNPKDLQQAMDVLIPLGEYFQVQDDYLDNFGD
PEFIGKIGTDIQDNKCSWLVNKALQKATPEQRQILEDNYGVKDKSKEL
VIKKLYDDMKIEQDYLDYEEEVVGDIKKKIEQVDESRGFKKEVLNAFL
AKIYKRQK Y. lipolytica ERG20 (F88W and N119W)
SEQ ID NO: 4
ASKAKFESVFPRISEELVQLLRDEGLPQDAVQWFSDSLQYNCVGGKLN
RGLSVVDTYQLLTGKKELDDEEYYRLALLGWLIELLQAFWLVSDDIMD
ESKTRRGQPCWYLKPKVGMIAIWDAFMLESGIYILLKKHFRQEKYYID
LVELFHDISFKTELGQLVDLLTAPEDEVDLNRFSLDKHSFIVRYKTAY
YSFYLPVVLAMYVAGITNPKDLQQAMDVLIPLGEYFQVQDDYLDNFGD
PEFIGKIGTDIQDNKCSWLVNKALQKATPEQRQILEDNYGVKDKSKEL
VIKKLYDDMKIEQDYLDYEEEVVGDIKKKIEQVDESRGFKKEVLNAFL
AKIYKRQK

TABLE 2

ERG20 HOMOLOGS

| Description | Ident | Accession |
| --- | --- | --- |
| YALI0E05753p [*Yarrowia lipolytica* CLIB122] | 99% | XP_503599.1 |
| hypothetical protein [*Nadsonia fulvescens* var. *elongata* DSM 6958] | 71% | ODQ67901.1 |
| hypothetical protein [*Lipomyces starkeyi* NRRL Y-11557] | 70% | ODQ75043.1 |
| Farnesyl pyrophosphate synthetase [*Galactomyces candidus*] | 68% | CDO55796.1 |
| hypothetical protein [*Kazachstania naganishii* CBS 8797] | 68% | XP_022463460.1 |
| farnesyl pyrophosphate synthase [*Saitoella complicata* NRRL Y-17804] | 66% | XP_019025287.1 |
| hypothetical protein [*Tetrapisispora blattae* CBS 6284] | 67% | XP_004179894.1 |
| hypothetical protein [*Torulaspora delbrueckii*] | 67% | XP_003680478.1 |
| unnamed protein product [*Zymoseptoria tritici* ST99CH_1E4] | 66% | SMR57088.1 |
| ERG20 farnesyl diphosphate synthase [*Zymoseptoria tritici* IPO323] | 66% | XP_003850094.1 |
| LAFE_0G04434g1_1 [*Lachancea fermentati*] | 68% | SCW03167.1 |
| ERG20-like protein [*Saccharomyces kudriavzevii* IFO 1802] | 66% | EJT43164.1 |
| hypothetical protein [*Dactylellina haptotyla* CBS 200.50] | 66% | EPS37682.1 |
| CYFA0S07e04902g1_1 [*Cyberlindnera fabianii*] | 65% | CDR41679.1 |
| probable farnesyl pyrophosphate synthetase [*Ramularia collo-cygni*] | 65% | XP_023628194.1 |
| farnesyl pyrophosphate synthetase [*Kluyveromyces marxianus* DMKU3-1042] | 65% | XP_022673909.1 |
| polyprenyl synt-domain-containing protein [*Sphaerulina musiva* SO2202] | 67% | XP_016759989.1 |

High levels of GPP production are dependent on adequate mevalonate production. Hydroxymethylglutaryl-CoA reductase (HMGR) catalyses the production of mevalonate from HMG-CoA and NADPH. HMGR is a rate limiting step in the GPP pathway in yeast. Accordingly, overexpressing HMGR may increase flux through the pathway and increase the production of GPP. HMGR is a GPP pathway gene. Other GPP pathway genes include those genes that are involved in the GPP pathway, the products of which either directly produce GPP or produce intermediates in the GPP pathway, for example, ERG10, ERG13, ERG12, ERG8, ERG19, IDI1 or ERG20, The HMGR1 sequence from *Y. lipolytica* consists of 999 amino acids (aa) (SEQ ID NO: 5), of which the first 500 aa harbor multiple transmembrane domains and a response element for signal regulation. The remaining 499 C-terminal residues contain a catalytic domain and an NADPH-binding region. Truncated HMGR1 (tHmgR) has been generated by deleting the N-terminal 500 aa (Gao et al. 2017). tHMGR is able to avoid self-degradation mediated by its N-terminal domain and is thus stabilized in the cytoplasm, which increases flux through the GPP pathway. The N-terminal 500 aa are shown with a dashed underline in SEQ ID NO: 5. The N-terminal 500 aa are deleted in SEQ ID NO: 6. In certain embodiments, the one or more GPP pathway genes comprise a hydroxymethylglutaryl-CoA reductase (HMGR); a truncated hydroxymethylglutaryl-CoA reductase (tHMGR); or a combination thereof. The sequence for the *Y. lipolytica* gene are shown herein, however the skilled person would understand that homologous genes may also be suitable. Examples of HMGR homologs as shown in Table 3. In certain embodiments, HMGR comprises a polynucleotide encoding a polypeptide that has at least 70%, 75%, 80%, 85%, 90%, 91%, 92%, 93%, 94%, 95%, 96%, 97%, 98%, 99% or 100% sequence identity to SEQ ID NO: 5. In certain embodiments, HMGR comprises a polypeptide that has at least 70%, 75%, 80%, 85%, 90%, 91%, 92%, 93%, 94%, 95%, 96%, 97%, 98%, 99% or 100% sequence identity to SEQ ID NO: 5. In certain embodiments, tHmgR comprises a polynucleotide encoding a polypeptide that has at least 70%, 75%, 80%, 85%, 90%, 91%, 92%, 93%, 94%, 95%, 96%, 97%, 98%, 99% or 100% sequence identity to SEQ ID NO: 6. In certain embodiments, tHmgR comprises a polypeptide that has at least 70%, 75%, 80%, 85%, 90%, 91%, 92%, 93%, 94%, 95%, 96%, 97%, 98%, 99% or 100% sequence identity to SEQ ID NO: 6.

The GPP producing and GPP pathway genes may be expressed using, for example, a constitutive TEF intron promoter or native promoter (Wong et al. 2017) and synthesized short terminator (Curran et al. 2015). Increased production of GPP can be determined by overexpressing a single heterologous gene encoding linalool synthase and then determining the production of linalool using, for example, a colorimentric assay (Ghorai 2012). Increased production of GPP may be indicated by a linalool concentration of at least 0.5 mg/L, 0.7 mg/L, 0.9 mg/L or preferably at least about 1 mg/L.

HMGR1

SEQ ID NO: 5

MLQAAIGKIVGFAVNRPIHTVVLTSIVASTAYLAILDIAIPGFEGTQP

ISYYHPAAKSYDNPADWTHIAEADIPSDAYRLAFAQIRVSDVQGGEAP

TIPGAVAVSDLDHRIVMDYKQWAPWTASNEQIASENHIWKHSFKDHVA

FSWIKWFRWAYLRLSTLIQGADNFDIAVVALGYLAMHYTFFSLFRSMR

KVGSHFWLASMALVSSTFAFLLAVVASSSLGYRPSMITMSEGLPFLVV

AIGFDRKVNLASEVLTSKSSQLAPMVQVITKIASKALFEYSLEVAALF

AGAYTGVPRLSQFCFLSAWILIFDYMFLLTFYSAVLAIKFEINHIKRN

RMIQDALKEDGVSAAVAEKVADSSPDAKLDRKSDVSLFGASGAIAVFK

IFMVLGFLGLNLINLTAIPHLGKAAAAAQSVTPITLSPELLHAIPASV

PVVVTFVPSVVYEHSQLILQLEDALTTFLAACSKTIGDPVISKYIFLC

LMVSTALNVYLFGATREVVRTQSVKVVEKHVPIVIEKPSEKEEDTSSE

DSIELTVGKQPKPVTETRSLDDLEAIMKAGKTKLLEDHEVVKLSLEGK

LPLYALEKQLGDNTRAVGIRRSIISQQSNTKTLETSKLPYLHYDYDRV

FGACCENVIGYMPLPVGVAGPMNIDGKNYHIPMATTEGCLVASTMRGC

KAINAGGGVTTVLTQDGMTRGPCVSFPSLKRAGAAKIWLDSEEGLKSM

RKAFNSTSRFARLQSLHSTLAGNLLFIRFRTTTGDAMGMNMISKGVEH

SLAVMVKEYGFPDMDIVSVSGNYCTDKKPAAINWIEGRGKSVVAEATI

PAHIVKSVLKSEVDALVELNISKNLIGSAMAGSVGGFNAHAANLVTAI

YLATGQDPAQNVESSNCITLMSNVDGNLLISVSMPSIEVGTIGGGTIL

EPQGAMLEMLGVRGPHIETPGANAQQLARIIASGVLAAELSLCSALAA

GHLVQSHMTHNRSQAPTPAKQSQADLQRLQNGSNICIRS tHmgR

SEQ ID NO: 6

TQSVKVVEKHVPIVIEKPSEKEEDTSSEDSIELTVGKQPKPVTETRSL

DDLEAIMKAGKTKLLEDHEVVKLSLEGKLPLYALEKQLGDNTRAVGIR

RSIISQQSNTKTLETSKLPYLHYDYDRVFGACCENVIGYMPLPVGVAG

PMNIDGKNYHIPMATTEGCLVASTMRGCKAINAGGGVTTVLTQDGMTR

GPCVSFPSLKRAGAAKIWLDSEEGLKSMRKAFNSTSRFARLQSLHSTL

AGNLLFIRFRTTTGDAMGMNMISKGVEHSLAVMVKEYGFPDMDIVSVS

GNYCTDKKPAAINWIEGRGKSVVAEATIPAHIVKSVLKSEVDALVELN

ISKNLIGSAMAGSVGGFNAHAANLVTAIYLATGQDPAQNVESSNCITL

MSNVDGNLLISVSMPSIEVGTIGGGTILEPQGAMLEMLGVRGPHIETP

GANAQQLARIIASGVLAAELSLCSALAAGHLVQSHMTHNRSQAPTPAK

QSQADLQRLQNGSNICIRS

TABLE 3

HMGR HOMOLOGS

| Description | Ident | Accession |
|---|---|---|
| YALI0E04807p [*Yarrowia lipolytica* CLIB122] | 100% | XP_503558.1 |
| hypothetical protein [*Nadsonia fulvescens* var. *elongata* DSM 6958] | 75% | ODQ65159.1 |
| hypothtical protein [*Galactomyces candidum*] | 74% | CDO55526.1 |
| hypothetical protein [*Lipomyces starkeyi* NRRL Y-11557] | 74% | ODQ70929.1 |
| hypothetical protein [*Meyerozyma guilliermondii* ATCC 6260] | 76% | EDK40614.2 |
| HMG1 [*Sugiyamaella lignohabitans*] | 73% | XP_018736018.1 |
| hypothetical protein [*Meyerozyma guilliermondii* ATCC 6260] | 76% | XP_001482757.1 |
| hypothetical protein [*Babjeviella inositovora* NRRL Y-12698] | 76% | XP_018984841.1 |
| DEHA2D09372p [*Debaryomyces hansenii* CBS767] | 75% | XP_458872.2 |
| 3-hydroxy-3-methylglutaryl-coenzyme A reductase 1 [[*Candida*] *glabrata*] | 75% | KTB22480.1 |
| hypothetical protein [*Vanderwaltozyma polyspora* DSM 70294] | 72% | XP_001643950.1 |
| LAFE_0A01552g1_1 [*Lachancea fermentati*] | 76% | SCV99364.1 |
| hypothetical protein [*Debaryomyces fabryi*] | 75% | XP_015466829.1 |
| uncharacterized protein [*Kuraishia capsulata* CBS 1993] | 76% | XP_022457391.1 |
| uncharacterized protein [*Candida*] *glabrata*] | 75% | XP_449268.1 |

Olivetolic Acid Producing Genes

The production of Olivetolic acid (OA) requires the substrates hexanoyl-CoA and 3 malonyl-CoA molecules, with the malonyl-CoA molecule produced in yeast naturally by ACC1 from Acetyl-CoA. Olivetolic acid production requires two enzymes for the condensation and subsequent cyclization of malonyl-CoA with hexanoyl-CoA. This process requires the tetraketide synthase, olivetolic synthase (OS), and the polyketide cyclase, olivetolic acid cyclase (OAC). In certain embodiments, the two or more olivetolic acid producing genes comprise olivetol synthase (OLS) and olivetolic acid cyclase (OAC). The sequences for the *Cannabis sativa* genes are shown herein, however the skilled person would understand that homologous genes may also be suitable. In certain embodiments, OLS comprises a polynucleotide encoding a polypeptide that has at least 70%, 75%, 80%, 85%, 90%, 91%, 92%, 93%, 94%, 95%, 96%, 97%, 98%, 99% or 100% sequence identity to SEQ ID NO: 7. In certain embodiments, OLS comprises a polypeptide that has at least 70%, 75%, 80%, 85%, 90%, 91%, 92%, 93%, 94%, 95%, 96%, 97%, 98%, 99% or 100% sequence identity to SEQ ID NO: 7. In certain embodiments, OAC comprises a polynucleotide encoding a polypeptide that has at least 70%, 75%, 80%, 85%, 90%, 91%, 92%, 93%, 94%, 95%, 96%, 97%, 98%, 99% or 100% sequence identity to SEQ ID NO: 8. In certain embodiments, OAC comprises a polypeptide that has at least 70%, 75%, 80%, 85%, 90%, 91%, 92%, 93%, 94%, 95%, 96%, 97%, 98%, 99% or 100% sequence identity to SEQ ID NO: 8.

Variants of the OA proteins, such as OAC, retain the ability to, for example, catalyze the C2-C7 aldol cyclization of linear pentyl tetra-β-ketide CoA as the substrate, to generate OA. For example, a variant of a OA protein, such as OAC, must retain the ability to catalyze the C2-C7 aldol cyclization of linear pentyl tetra-β-ketide CoA as the substrate, to generate OA with at least about 50%, at least about 60%, at least about 70%, at least about 80%, at least about 90%, or at least about 100% efficacy compared to the original sequence. In preferred embodiments, a variant of a OA protein, such as OAC, has improved activity over the sequence from which it is derived in that the improved variant common cannabinoid protein has more than 110%, 120%, 130%, 140%, or and 150% improved activity in catalyzing the C2-C7 aldol cyclization of linear pentyl tetra-β-ketide CoA as the substrate, to generate OA, as compared to the sequence from which the improved variant is derived.

The OA producing genes OLS and OAC may be expressed using, for example, a constitutive TEF intron promoter or native promoter (Wong et al. 2017) and synthesized short terminator (Curran et al. 2015). Increased production of OA may be determined using high-performance liquid chromatography (HPLC) or Liquid chromatography-mass spectrometry (LC/MS). As yeast do not produce OA endogenously, the presence of OA indicates that OLS and OAS are functioning.

OLS
SEQ ID NO: 7

MNHLRAEGPASVLAIGTANPENILLQDEFPDYYFRVTKSEHMTQLKEK

FRKICDKSMIRKRNCFLNEEHLKQNPRLVEHEMQTLDARQDMLVVEVP

KLGKDACAKAIKEWGQPKSKITHLIFTSASTTDMPGADYHCAKLLGLS

PSVKRVMMYQLGCYGGGTVLRIAKDIAENNKGARVLAVCCDIMACLFR

GPSESDLELLVGQAIFGDGAAAVIVGAEPDESVGERPIFELVSTGQTI

LPNSEGTIGGHIREAGLIFDLHKDVPMLISNNIEKCLIEAFTPIGISD

WNSIFWITHPGGKAILDKVEEKLHLKSDKFVDSRHVLSEHGNMSSSTV

LFVMDELRKRSLEEGKSTTGDGFEWGVLFGFGPGLTVERVVVRSVPIK

Y

OAC
SEQ ID NO: 8

MAVKHLIVLKFKDEITEAQKEEFFKTYVNLVNIIPAMKDVYWGKDVTQ

KNKEEGYTHIVEVTFESVETIQDYIIHPAHVGFGDVYRSFWEKLLIFD

YTPRK

Cannabinoid Precursor or Cannabinoid Producing Genes

The production of the cannabinoids tetrahydrocannabinolic acid (THCA), cannabidiolic acid (CBDA) and cannabichromenic acid (CBCA) involves the prenylation of OA with GPP to CBGA by an aromatic prenyltransferase, and then CBDA, THCA or CBCA by CBDAS, THCAS or CBCAS, respectively.

Yeast do not naturally product CBGA, and therefore CBGA may be formed by heterologous expression of a CBGA synthase such as the membrane-bound CBGA synthase (CBGAS) from *C. sativa*. CBGAS is also known as geranylpyrophosphate olivetolate geranyltransferase, of which there are several forms, CsPT1, CsPT3 and CsPT4. In certain embodiments, the one or more cannabinoid precursor or cannabinoid producing genes comprise: a soluble aromatic prenyltransferase; a cannabigerolic acid synthase (CBGAS); or a combination thereof; either alone or in combination with the cannabinoid producing genes: tetrahydrocannabinolic acid synthase (THCAS); cannabidiolic acid synthase (CBDAS); cannabichromenic acid synthase (CBCAS); or any combination thereof. The sequences for the *Cannabis sativa* genes CBGAS, THCAS, CBDAS and CBCAS are shown herein, however the skilled person would understand that homologous genes may also be suitable.

In certain embodiments, CBGA synthase comprises a polynucleotide encoding a polypeptide that has at least 70%, 75%, 80%, 85%, 90%, 91%, 92%, 93%, 94%, 95%, 96%, 97%, 98%, 99% or 100% sequence identity to SEQ ID NO: 9. In certain embodiments, CBGA synthase comprises a polynucleotide encoding a polypeptide that has at least 70%, 75%, 80%, 85%, 90%, 91%, 92%, 93%, 94%, 95%, 96%, 97%, 98%, 99% or 100% sequence identity to SEQ ID NO: 10. In certain embodiments, CBGA synthase comprises a polynucleotide encoding a polypeptide that has at least 70%, 75%, 80%, 85%, 90%, 91%, 92%, 93%, 94%, 95%, 96%, 97%, 98%, 99% or 100% sequence identity to SEQ ID NO: 11. In certain embodiments, CBGA synthase comprises a polypeptide that has at least 70%, 75%, 80%, 85%, 90%, 91%, 92%, 93%, 94%, 95%, 96%, 97%, 98%, 99% or 100% sequence identity to SEQ ID NOS: 9, 10 or 11. CBGA may also be formed by heterologous expression of a soluble aromatic prenyltransferase. In certain embodiments, the soluble aromatic prenyltransferase is NphB from *Streptomyces* sp. strain CL190 (i.e. wild type NphB) (Bonitz et al., 2011; Kuzuyama et al., 2005; Zirpel et al., 2017). In certain embodiments, the soluble aromatic prenyltransferase is NphB, comprising a mutation of a Q161A substitution. NphB (Q161A) produces more CBGA that wild type NphB (Muntendam 2015). Wild type NphB produces 15% CBGA and 85% of another by-product. The sequence for the *Streptomyces* sp. strain CL190 gene NphB is shown herein, however the skilled person would understand that homologous genes may also be suitable. In certain embodiments, NphB comprises a polynucleotide encoding a polypeptide that has at least 70%, 75%, 80%, 85%, 90%, 91%, 92%, 93%, 94%, 95%, 96%, 97%, 98%, 99% or 100% sequence identity to SEQ ID NO: 12. In certain embodiments, NphB comprises a polypeptide that has at least 70%, 75%, 80%, 85%, 90%, 91%, 92%, 93%, 94%, 95%, 96%, 97%, 98%, 99% or 100% sequence identity to SEQ ID NO: 12.

Variants of the cannabinoid precursor or cannabinoid producing protein, such as NphB (Q161A), retains the ability to attach geranyl groups to aromatic substrates—such as converting OA and GPP to CBGA. For example, a variant Cannabinoid precursor or cannabinoid producing protein, such as NphB (Q161A), must retain the ability to attach geranyl groups to aromatic substrates, such as converting OA and GPP to CBGA, with at least about 50%, at least about 60%, at least about 70%, at least about 80%, at least about 900%, or at least about 100% efficacy compared to the original sequence. In preferred embodiments, a variant of a Cannabinoid precursor or cannabinoid producing protein, such as NphB (Q161A), has improved activity over the sequence from which it is derived in that the improved variant common cannabinoid protein has more than 110%, 120%, 130%, 140%, or and 150% improved activity in attach geranyl groups to aromatic substrates, such as converting OA and GPP to CBGA, as compared to the sequence from which the improved variant is derived.

The cannabinoid precursor or cannabinoid producing genes CBGAS, soluble aromatic prenyltransferase, CBGAS, THCAS, CBDAS and CBCAS may be expressed using, for example, a constitutive TEF intron promoter or native promoter (Wong et al. 2017) and synthesized short terminator (Curran et al. 2015). The production of one or more cannabinoid precursors or cannabinoids may be determined using a variety of methods. For example, if all of the precursors are available in the yeast cell, then the presence of the product, such as THCA, may be determined using HPLC or gas chromatography (GC). Alternatively, if only a portion of the cannabinoid synthesis pathway present, then cannabinoids will not be present and the activity of one or more genes can be checked by adding a gene and precursor. For example, to check CBGAS activity, OA and GPP are added to a crude cellular lysate. For checking CBCAS, THCAS or CBDAS activity, CBGA is added to a crude cellular lysate. A crude lysate or purified proteins may be used. Further, it may be necessary to use an aqueous/organic two-liquid phase setup in order to solubilize the hydrophobic substrate (e.g. CBGA) and to allow in situ product removal.

CsPT1

SEQ ID NO: 9

MGLSSVCTFSFQTNYHTLLNPHNNNPKTSLLCYRHPKTPIKYSYNNFP

SKHCSTKSFHLQNKCSESLSIAKNSIRAATTNQTEPPESDNHSVATKI

LNFGKACWKLQRPYTIIAFTSCACGLFGKELLHNTNLISWSLMFKAFF

FLVAILCIASFTTTINQIYDLHIDRINKPDLPLASGEISVNTAWIMSI

IVALFGLIITIKMKGGPLYIFGYCFGIFGGIVYSVPPFRWKQNPSTAF

LLNFLAHIITNFTFYYASRAALGLPFELRPSFTFLLAFMKSMGSALAL

IKDASDVEGDTKFGISTLASKYGSRNLTLFCSGIVLLSYVAAILAGII

WPQAFNSNVMLLSHAILAFWLILQTRDFALTNYDPEAGRRFYEFMWKL

YYAEYLVYVFI

CsPT3

SEQ ID NO: 10

MGLSLVCTFSFQTNYHTLLNPHNKNPKNSLLSYQHPKTPIIKSSYDNF

PSKYCLTKNFHLLGLNSHNRISSQSRSIRAGSDQIEGSPHHESDNSIA

TKILNFGHTCWKLQRPYVVKGMISIACGLFGRELFNNRHLFSWGLMWK

AFFALVPILSFNFFAAIMNQIYDVDIDRINKPDLPLVSGEMSIETAWI

LSIIVALTGLIVTIKLKSAPLFVFIYIFGIFAGFAYSVPPIRWKQYPF

TNFLITISSHVGLAFTSYSATTSALGLPFVWRPAFSFIIAFMTVMGMT

IAFAKDISDIEGDAKYGVSTVATKLGARNMTFVVSGVLLLNYLVSISI

GIIWPQVFKSNIMILSHAILAFCLIFQTRELALANYASAPSRQFFEFI

WLLYYAEYFVYVFI

CsPT4

SEQ ID NO: 11

MVFSSVCSFPSSLGTNFKLVPRSNFKASSSHYHEINNFINNKPIKFSY

FSSRLYCSAKPIVHRENKFTKSFSLSHLQRKSSIKAHGEIEADGSNGT

SEFNVMKSGNAIWRFVRPYAAKGVLFNSAAMFAKELVGNLNLFSWPLM

FKILSFTLVILCIFVSTSGINQIYDLDIDRLNKPNLPVASGEISVELA

WLLTIVCTISGLTLTIITNSGPFFPFLYSASIFFGFLYSAPPFRWKKN

PFTACFCNVMLYVGTSVGVYYACKASLGLPANWSPAFCLLFWFISLLS

-continued

IPISIAKDLSDIEGDRKFGIITFSTKFGAKPIAYICHGLMLLNYVSVM

AAAIIWPQFFNSSVILLSHAFMAIWVLYQAWILEKSNYATETCQKYYI

FLWIIFSLEHAFYLFM

NphB
SEQ ID NO: 12
MSEAADVERVYAAMEEAAGLLGVACARDKIYPLLSTFQDTLVEGGSVV

VFSMASGRHSTELDFSISVPTSHGDPYATVVEKGLFPATGHPVDDLLA

DTQKHLPVSMFAIDGEVTGGFKKTYAFFPTDNMPGVAELSAIPSMPPA

VAENAELFARYGLDKVAMTSMDYKKRQVNLYFSELSAQTLEAESVLAL

VRELGLHVPNELGLKFCKRSFSVYPTLNWETGKIDRLCFAVISNDPTL

VPSSDEGDIEKFHNYATKAPYAYVGEKRTLVYGLTLSPKEEYYKLGAY

YHITDVQRGLLKAFDSLED

Producing CBGA is an initial step in producing many cannabinoids from *C. sativa* in yeast. Once CBGA is produced a single additional enzymatic step is required to turn CBGA into many other cannabinoids (CBDA, THCA, CBCA, etc.). The acidic forms of the cannabinoids can be used as a pharmaceutical product or the acidic cannabinoids can be turned into their neutral form for use, for example Cannabidiol (CBD) is produced from CBDA through decarboxylation. The resulting cannabinoid products will be used in the pharmaceutical/nutraceutical industry to treat a wide range of health issues. The genes for tetrahydrocannabinolic acid synthase (THCAS), cannabidiolic acid synthase (CBDAS) and cannabichromenic acid synthase (CBCAS) may be derived from *C. sativa*, however, the skilled person would understand that homologous genes may also be suitable. In certain embodiments, THCAS comprises a polynucleotide encoding a polypeptide that has at least 70%, 75%, 80%, 85%, 90%, 91%, 92%, 93%, 94%, 95%, 96%, 97%, 98%, 99% or 100% sequence identity to SEQ ID NO: 13. In certain embodiments, THCAS comprises a polypeptide that has at least 70%, 75%, 80%, 85%, 90%, 91%, 92%, 93%, 94%, 95%, 96%, 97%, 98%, 99% or 100% sequence identity to SEQ ID NO: 13. In certain embodiments, CBDAS comprises a polynucleotide encoding a polypeptide that has at least 70%, 75%, 80%, 85%, 90%, 91%, 92%, 93%, 94%, 95%, 96%, 97%, 98%, 99% or 100% sequence identity to SEQ ID NO: 14. In certain embodiments, CBDAS comprises a polypeptide that has at least 70%, 75%, 80%, 85%, 90%, 91%, 92%, 93%, 94%, 95%, 96%, 97%, 98%, 99% or 10% sequence identity to SEQ ID NO: 14. In certain embodiments, CBCAS comprises a polynucleotide encoding a polypeptide that has at least 70%, 75%, 80%, 85%, 90%, 91%, 92%, 93%, 94%, 95%, 96%, 97%, 98%, 99% or 100% sequence identity to SEQ ID NO: 15. In certain embodiments, CBCAS comprises a polypeptide that has at least 70%, 75%, 80%, 85%, 90%, 91%, 92%, 93%, 94%, 95%, 96%, 97%, 98%, 99% or 100% sequence identity to SEQ ID NO: 15. Accordingly, in certain embodiments, the one or more cannabinoid precursor or cannabinoid producing genes comprise soluble aromatic prenyltransferase, cannabigerolic acid synthase (CBGAS), tetrahydrocannabinolic acid synthase (THCAS), cannabidiolic acid synthase (CBDAS) and cannabichromenic acid synthase (CBCAS).

THCAS
SEQ ID NO: 13
NPRENFLKCFSKHIPNNVANPKLVYTQHDQLYMSILNSTIQNLRFISD

TTPKPLVIVTPSNNSHIQATILCSKKVGLQIRTRSGGHDAEGMSYISQ

VPFVVVDLRNMHSIKIDVHSQTAWVEAGATLGEVYYWINEKNENLSFP

GGYCPTVGVGGHFSGGGYGALMRNYGLAADNIIDAHLVNVDGKVLDRK

SMGEDLFWAIRGGGGENFGIIAAWKIKLVAVPSKSTIFSVKKNMEIHG

LVKLFNKWQNIAYKYDKDLVLMTHFITKNITDNHGKNKTTVHGYFSSI

FHGGVDSLVDLMNKSFPELGIKKTDCKEFSWIDTTIFYSGVVNFNTAN

FKKEILLDRSAGKKTAFSIKLDYVKKPIPETAMVKILEKLYEEDVGAG

MYVLYPYGGIMEEISESAIPFPHRAGIMYELWYTASWEKQEDNEKHIN

WVRSVYNFTTPYVSQNPRLAYLNYRDLDLGKTNHASPNNYTQARIWGE

KYFGKNFNRLVKVKTKVDPNNFFRNEQSIPPLPPHHH

CBDAS
SEQ ID NO: 14
NPRENFLKCFSQYIPNNATNLKLVYTQNNPLYMSVLNSTIHNLRFTSD

TTPKPLVIVTPSHVSHIQGTILCSKKVGLQIRTRSGGHDSEGMSYISQ

VPFVIVDLRNMRSIKIDVHSQTAWVEAGATLGEVYYWVNEKNENLSLA

AGYCPTVCAGGHFGGGGYGPLMRNYGLAADNIIDAHLVNVHGKVLDRK

SMGEDLFWALRGGGAESFGIIVAWKIRLVAVPKSTMFSVKKIMEIHEL

VKLVNKWQNIAYKYDKDLLLMTHFITRNITDNQGKNKTAIHTYFSSVF

LGGVDSLVDLMNKSFPELGIKKTDCRQLSWIDTIIFYSGVVNYDTDNF

NKEILLDRSAGQNGAFKIKLDYVKKPIPESVFVQILEKLYEEDIGAGM

YALYPYGGIMDEISESAIPFPHRAGILYELWYICSWEKQEDNEKHLNW

IRNIYNFMTPYVSKNPRLAYLNYRDLDIGINDPKNPNNYTQARIWGEK

YFGKNFDRLVKVKTLVDPNNFFRNEQSIPPLPRHRH

CBCAS
SEQ ID NO: 15
NPQENFLKCFSEYIPNNPANPKFIYTQHDQLYMSVLNSTIQNLRFTSD

TTPKPLVIVTPSNVSHIQASILCSKKVGLQIRTRSGGHDAEGLSYISQ

VPFAIVDLRNMHTVKVDIHSQTAWVEAGATLGEVYYWINEMNENFSFP

GGYCPTVGVGGHFSGGGYGALMRNYGLAADNIIDAHLVNVDGKVLDRK

SMGEDLFWAIRGGGGENFGIIAAWKIKLVVVPSKATIFSVKKNMEIHG

LVKLFNKWQNIAYKYDKDLMLTTHFRTRNITDNHGKNKTTVHGYFSSI

FLGGVDSLVDLMNKSFPELGIKKTDCKELSWIDTTIFYSGVVNYNTAN

FKKEILLDRSAGKKTAFSIKLDYVKKLIPETAMVKILEKLYEEEVGVG

MYVLYPYGGIMDEISESAIPFPHRAGIMYELWYTATWEKQEDNEKHIN

WVRSVYNFTTPYVSQNPRLAYLNYRDLDLGKTNPESPNNYTQARIWGE

KYFGKNFNRLVKVKTKADPNNFFRNEQSIPPLPPRHH

Hexanoyl-CoA Producing Genes

A first step in the pathway for cannabinoid production in *C. sativa* begins with the conversion of hexanoic acid (a simple fatty acid) to hexanoyl-CoA by hexanoyl-CoA synthetase. For cannabinoid production in yeast, hexanoyl-CoA may be produced by expression of hexanoyl-CoA synthases HexA & HexB or StcJ & StcK, or mutated FAS1&2. Yeast do not naturally produce hexanoyl-CoA. The genes HexA &

HexB encode the alpha (hexA) and beta (hexB) subunits of the hexanoate synthase (HexS) from *Aspergillus parasiticus* SU-1 (Hitchman et al. 2001). The genes StcJ and StcK are from *Aspergillus nidulans* and encode yeast-like FAS proteins (Brown et al. 1996). As would be understood by the person skilled in the art, many fungi would have hexanoate synthase or fatty acid synthase genes, which could readily be identified by sequencing of the DNA and sequence alignments with the known genes disclosed herein. Similarly, the skilled person would understand that homologous genes in different organisms may also be suitable. Examples of HexA and HexB homologs as shown in Tables 4 and 5. Examples of FAS1 and FAS2 homologs as shown in Tables 6 and 7. The endogenous yeast genes FAS1 (Fatty acid synthase subunit beta) and FAS2 (Fatty acid synthase subunit alpha) form fatty acid synthase FAS which catalyses the formation of long-chain fatty acids from acetyl-CoA, malonyl-CoA and NADPH. Mutated FAS produces short-chain fatty acids, such as hexanoic acid. Several different combinations of mutations enable the production of hexanoic acid. The mutations include: FAS1 I306A and FAS2 G1250S; FAS1 I306A and FAS2 G1250S and M1251W; and FAS1 I306A, R1834K and FAS2 G1250S (Gajewski et al. 2017). Mutated FAS2 and FAS1 may be expressed under the control of any suitable promoter, including, but not limited to the alcohol dehydrogenase II promoter of *Y. lipolytica*. Alternatively, genomic FAS2 and FAS1 can be directly mutated using, for example, homologous recombination or CRISPR-Cas9 genome editing technology.

Accordingly, in certain embodiments, HexA comprises a polynucleotide encoding a polypeptide that has at least 70%, 75%, 80%, 85%, 90%, 91%, 92%, 93%, 94%, 95%, 96%, 97%, 98%, 99% or 100% sequence identity to SEQ ID NO: 16. In certain embodiments, HexA comprises a polypeptide that has at least 70%, 75%, 80%, 85%, 90%, 91%, 92%, 93%, 94%, 95%, 96%, 97%, 98%, 99% or 100% sequence identity to SEQ ID NO: 16. In certain embodiments, HexB comprises a polynucleotide encoding a polypeptide that has at least 70%, 75%, 80%, 85%, 90%, 91%, 92%, 93%, 94%, 95%, 96%, 97%, 98%, 99% or 100% sequence identity to SEQ ID NO: 17. In certain embodiments, HexB comprises a polypeptide that has at least 70%, 75%, 80%, 85%, 90%, 91%, 92%, 93%, 94%, 95%, 96%, 97%, 98%, 99% or 100% sequence identity to SEQ ID NO: 17. In certain embodiments, StcJ comprises a polynucleotide encoding a polypeptide that has at least 70%, 75%, 80%, 85%, 90%, 91%, 92%, 93%, 94%, 95%, 96%, 97%, 98%, 99% or 100% sequence identity to SEQ ID NO: 18. In certain embodiments, StcJ comprises a polypeptide that has at least 70%, 75%, 80%, 85%, 90%, 91%, 92%, 93%, 94%, 95%, 96%, 97%, 98%, 99% or 100% sequence identity to SEQ ID NO: 18. In certain embodiments, StcK comprises a polynucleotide encoding a polypeptide that has at least 70%, 75%, 80%, 85%, 90%, 91%, 92%, 93%, 94%, 95%, 96%, 97%, 98%, 99% or 100% sequence identity to SEQ ID NO: 19. In certain embodiments, StcK comprises a polypeptide that has at least 70%, 75%, 80%, 85%, 90%, 91%, 92%, 93%, 94%, 95%, 96%, 97%, 98%, 99% or 100% sequence identity to SEQ ID NO: 19. In certain embodiments, FAS2 comprises a polynucleotide encoding a polypeptide that has at least 70%, 75%, 80%, 85%, 90%, 91%, 92%, 93%, 94%, 95%, 96%, 97%, 98%, 99% or 100% sequence identity to SEQ ID NO: 20 and one of the combinations of mutations defined above. In certain embodiments, FAS2 comprises a polypeptide that has at least 70%, 75%, 80%, 85%, 90%, 91%, 92%, 93%, 94%, 95%, 96%, 97%, 98%, 99% or 100% sequence identity to SEQ ID NO: 20 and one of the combinations of mutations defined above. In certain embodiments, FAS1 comprises a polynucleotide encoding a polypeptide that has at least 70%, 75%, 80%, 85%, 90%, 91%, 92%, 93%, 94%, 95%, 96%, 97%, 98%, 99% or 100% sequence identity to SEQ ID NO: 21 and one of the combinations of mutations defined above. In certain embodiments, FAS1 comprises a polypeptide that has at least 70%, 75%, 80%, 85%, 90%, 91%, 92%, 93%, 94%, 95%, 96%, 97%, 98%, 99% or 100% sequence identity to SEQ ID NO: 21 and one of the combinations of mutations defined above.

Variants of the Hexanoyl-CoA producing proteins retain the ability to catalyse the formation of long-chain fatty acids from acetyl-CoA, malonyl-CoA and NADPH. For example, a variant of a Hexanoyl-CoA producing protein must retain the ability to catalyse the formation of long-chain fatty acids from acetyl-CoA, malonyl-CoA and NADPH with at least about 50%, at least about 60%, at least about 70%, at least about 80%, at least about 900%, or at least about 100% efficacy compared to the original sequence. In preferred embodiments, a variant of a Hexanoyl-CoA producing protein has improved activity over the sequence from which it is derived in that the improved variant common cannabinoid protein has more than 110%, 120%, 130%, 140%, or and 150% improved activity in catalysing the formation of long-chain fatty acids from acetyl-CoA, malonyl-CoA and NADPH, as compared to the sequence from which the improved variant is derived.

The hexanoyl-CoA synthases HexA & HexB, StcJ & StcK, or mutated FAS1&2 may be expressed using, for example, a constitutive TEF intron promoter or native promoter (Wong et al. 2017) and synthesized short terminator (Curran et al. 2015). The production of hexanoyl-CoA in yeast may be determined by directly measuring the concentration of hexanoyl-CoA extracted from yeast cells using LC-MS.

```
HexA
                                                          SEQ ID NO: 16
MVIQGKRLAASSIQLLASSLDAKKLCYEYDERQAPGVTQITEEAPTEQPPLSTPPSLPQTPNIS

PISASKIVIDDVALSRVQIVQALVARKLKTAIAQLPTSKSIKELSGGRSSLQNELVGDIHNEFS

SIPDAPEQILLRDFGDANPTVQLGKTSSAAVAKLISSKMPSDFNANAIRAHLANKWGLGPLRQT

AVLLYAIASEPPSRLASSSAAEEYWDNVSSMYAESCGITLRPRQDTMNEDAMASSAIDPAVVAE

FSKGHRRLGVQQFQALAEYLQIDLSGSQASQSDALVAELQQKVDLWTAEMTPEFLAGISPMLDV

KKSRRYGSWWNMARQDVLAFYRRPSYSEFVDDALAFKVFLNRLCNRADEALLNMVRSLSCDAYF

KQGSLPGYHAASRLLEQAITSTVADCPKARLILPAVGPHTTITKDGTIEYAEAPRQGVSGPTAY
```

-continued

```
IQSLRQGASFIGLKSADVDTQSNLTDALLDAMCLALHNGISFVGKTFLVTGAGQGSIGAGVVRL
LLEGGARVLVTTSREPATTSRYFQQMYDNHGAKFSELRVVPCNLASAQDCEGLIRHVYDPRGLN
WDLDAILPFAAASDYSTEMHDIRGQSELGHRLMLVNVFRVLGHIVHCKRDAGVDCHPTQVLLPL
SPNHGIFGGDGMYPESKLALESLFHRIRSESWSDQLSICGVRIGWTRSTGLMTAHDIIAETVEE
HGIRTFSVAEMALNIAMLLTPDFVAHCEDGPLDADFTGSLGTLGSIPGFLAQLHQKVQLAAEVI
RAVQAEDEHERFLSPGTKPTLQAPVAPMHPRSSLRVGYPRLPDYEQEIRPLSPRLERLQDPANA
VVVVGYSELGPWGSARLRWEIESQGQWTSAGYVELAWLMNLIRHVNDESYVGWVDTQTGKPVRD
GEIQALYGDHIDNHTGIRPIQSTSYNPERMEVLQEVAVEEDLPEFEVSQLTADAMRLRHGANVS
IRPSGNPDACHVKLKRGAVILVPKTVPFVWGSCAGELPKGWTPAKYGIPENLIHQVDPVTLYTI
CCVAEAFYSAGITHPLEVFRHIHLSELGNFIGSSMGGPTKTRQLYRDVYFDHEIPSDVLQDTYL
NTPAAWVNMLLLGCTGPIKTPVGACATGVESIDSGYESIMAGKTKMCLVGGYDDLQEEASYGFA
QLKATVNVEEEIACGRQPSEMSRPMAESRAGFVEAHGCGVQLLCRGDIALQMGLPIYAVIASSA
MAADKIGSSVPAPGQGILSFSRERARSSMISVTSRPSSRSSTSSEVSDKSSLTSITSISNPAPR
AQRARSTTDMAPLRAALATWGLTIDDLDVASLHGTSTRGNDLNEPEVIETQMRHLGRTPGRPLW
AICQKSVTGHPKAPAAAWMLNGCLQVLDSGLVPGNRNLDTLDEALRSASHLCFPTRTVQLREVK
AFLLTSFGFGQKGGQVVGVAPKYFFATLPRPEVEGYYRKVRVRTEAGDRAYAAAVMSQAVVKIQ
TQNPYDEPDAPRIFLDPLARISQDPSTGQYRFRSDATPALDDDALPPPGEPTELVKGISSAWIE
EKVRPHMSPGGTVGVDLVPLASFDAYKNAIFVERNYTVRERDWAEKSADVRAAYASRWCAKEAV
FKCLQTHSQGAGAAMKEIEIEHGGNGAPKVKLRGAAQTAARQRGLEGVQLSISYGDDAVIAVAL
GLMSGAS

HexB
                                                          SEQ ID NO: 17
MGSVSREHESIPIQAAQRGAARICAAFGGQGSNNLDVLKGLLELYKRYGPDLDELLDVASNTLS
QLASSPAAIDVHEPWGFDLRQWLTTPEVAPSKEILALPPRSFPLNTLLSLALYCATCRELELDP
GQFRSLLHSSTGHSQGILAAVAITQAESWPTFYDACRTVLQISFWIGLEAYLFTPSSAASDAMI
QDCIEHGEGLLSSMLSVSGLSRSQVERVIEHVNKGLGECNRWVHLALVNSHEKFVLAGPPQSLW
AVCLHVRRIRADNDLDQSRILFRNRKPIVDILFLPISAPFHTPYLDGVQDRVIEALSSASLALH
SIKIPLYHTGTGSNLQELQPHQLIPTLIRAITVDQLDWPLVCRGLNATHVLDFGPGQTCSLIQE
LTQGTGVSVIQLTTQSGPKPVGGHLAAVNWEAEFGLRLHANVHGAAKLHNRMTTLLGKPPVMVA
GMTPTTVRWDFVAAVAQAGYHVELAGGGYHAERQFEAEIRRLATAIPADHGITCNLLYAKPTTF
SWQISVIKDLVRQGVPVEGITIGAGIPSPEVVQECVQSIGLKHISFKPGSFEAIHQVIQIARTH
PNFLIGLQWTAGRGGGHHSWEDFHGPILATYAQIRSCPNILLVVGSGFGGGPDTFPYLTGQWAQ
AFGYPCMPFDGVLLGSRMMVAREAHTSAQAKRLIIDAQGVGDADWHKSFDEPTGGVVTVNSEFG
QPIHVLATRGVMLWKELDNRVFSIKDTSKRLEYLRNHRQEIVSRLNADFARPWFAVDGHGQNVE
LEDMTYLEVLRRLCDLTYVSHQKRWVDPSYRILLLDFVHLLRERFQCAIDNPGEYPLDIIVRVE
ESLKDKAYRTLYPEDVSLLMHLFSRRDIKPVPFIPRLDERFETWFKKDSLWQSEDVEAVIGQDV
QRIFIIQGPMAVQYSISDDESVKDILHNICNHYVEALQADSRETSIGDVHSITQKPLSAFPGLK
VTTNRVQGLYKFEKVGAVPEMDVLFEHIVGLSKSWARTCLMSKSVFRDGSRLHNPIRAALQLQR
GDTIEVLLTADSEIRKIRLISPTGDGGSTSKVVLEIVSNDGQRVFATLAPNIPLSPEPSVVFCF
KVDQKPNEWTLEEDASGRAERIKALYMSLWNLGFPNKASVLGLNSQFTGEELMITTDKIRDFER
VLRQTSPLQLQSWNPQGCVPIDYCVVIAWSALTKPLMVSSLKCDLLDLLHSAISFHYAPSVKPL
RVGDIVKTSSRILAVSVRPRGTMLTVSADIQRQGQHVVTVKSDFFLGGPVLACETPFELTEEPE
```

MVVHVDSEVRRAILHSRKWLMREDRALDLLGRQLLFRLKSEKLFRPDGQLALLQVTGSVFSYSP
DGSTTAFGRVYFESESCTGNVVMDFLHRYGAPRAQLLELQHPGWTGTSTVAVRGPRRSQSYARV
SLDHNPIHVCPAFARYAGLSGPIVHGMETSAMMRRIAEWAIGDADRSRFRSWHITLQAPVHPND
PLRVELQHKAMEDGEMVLKVQAFNERTEERVAEADAHVEQETTAYVFCGQGSQRQGMGMDLYVN
CPEAKALWARADKHLWEKYGFSILHIVQNNPPALTVHFGSQRGRRIRANYLRMMGQPPIDGRHP
PILKGLTRNSTSYTFSYSQGLLMSTQFAQPALALMEMAQFEWLKAQGVVQKGARFAGHSLGEYA
ALGACASFLSFEDLISLIFYRGLKMQNALPRDANGHTDYGMLAADPSRIGKGFEEASLKCLVHI
IQQETGWFVEVVNYNINSQQYVCAGHFRALWMLGKICDDLSCHPQPETVEGQELRAMVWKHVPT
VEQVPREDRMERGRATIPLPGIDIPYHSTMLRGEIEPYREYLSERIKVGDVKPCELVGRWIPNV
VGQPFSVDKSYVQLVHGITGSPRLHSLLQQMA

StcJ                                                SEQ ID NO: 18
MTQKTIQQVPRQGLELLASTQDLAQLCYIYGEPAEGEDSTADESIINTPQCSTIPEVAVEPEVQ
PIPDTPLTAIFIIRALVARKLRRSETEIDPSRSIKELCGGKSTLQNELIGELGNEFQTSLPDRA
EDVSLADLDAALGEVSLGPTSVSLLQRVFTAKMPARMTVSNVRERLAEIWGLGFHRQTAVLVAA
LAAEPHSRLTSLEAAYQYWDGLNEAYGQSLGLFLRKAISQQAARSDDQGAQAIAPADSLGSKDL
ARKQYEALREYLGIRTPTTKQDGLDLADLQQKLDCWTAEFSDDFLSQISRRFDARKTRWYRDWW
NSARQELLTICQNSNVQWTDKMREHFVQRAEEGLVEIARAHSLAKPLVPDLIQAISLPPVVRLG
RLATMMPRTVVTLKGEIQCEEHEREPSCFVEFFSSWIQANNIRCTIQSNGEDLTSVFINSLVHA
SQQGVSFPNHTYLITGAGPGSIGQHIVRRLLTGGARVIVTTSREPLPAAAFFKELYSKCGNRGS
QLHLVPFNQASVVDCERLIGYIYDDLGLDLDAILPFAATSQVGAEIDGLDASNEAAFRLMLVNV
LRLVGFVVSQKRRRGISCRPTQVVLPLSPNHGILGGDGLYAESKRGLETLIQRFHSESWKEELS
ICGVSIGWTRSTGLMAANDLVAETAEKQGRVLTFSVDEMGDLISLLLTPQLATRCEDAPVMADF
SGNLSCWRDASAQLAAARASLRERADTARALAQEDEREYRCRRAGSTQEPVDQRVSLHLGFPSL
PEYDPLLHPDLVPADAVVVVGFAELGPWGSARIRWEMESRGCLSPAGYVETAWLMNLIRHVDNV
NYVGWVDGEDGKPVADADIPKRYGERILSNAGIRSLPSDNREVFQEIVLEQDLPSFETTRENAE
ALQQRHGDMVQVSTLKNGLCLVQLQHGATIRVPKSIMSPPGVAGQLPTGWSPERYGIPAEIVQQ
VDPVALVLLCCVAEAFYSAGISDPMEIFEHIHLSELGNFVGSSMGGVVNTRALYHDVCLDKDVQ
SDALQETYLNTAPAWVNMLYLGAAGPIKTPVGACATALESVDSAVESIKAGQTKICLVGGYDDL
QPEESAGFARMKATVSVRDEQARGREPGEMSRPTAASRSGFVESQGCGVQLLCRGDVALAMGLP
IYGIIAGTGMASDGIGRSVPAPGQGILTFAQEDAQNPAPSRTALARWGLGIDDITVASLHATST
PANDTNEPLVIQREMTHLGRTSGRPLWAICQKFVTGHPKAPAAAWMLNGCLQVLDTGLVPGNRN
ADDVDPALRSFSHLCFPIRSIQTDGIKAFLLNSCGFGQKEAQLVGVHPRYFLGLLSEPEFEEYR
TRRQLRIAGAERAYISAMMTNSIVCVQSHPPFGPAEMHSILLDPSARICLDSSTNSYRVTKAST
PVYTGFQRPHDKREDPRPSTIGVDTVTLSSFNAHENAIFLQRNYTERERQSLQLQSHRSFRSAV
ASGWCAKEAVFKCLQTVSKGAGAAMSEIEIVRVQGAPSVLHGDALAAAQKAGLDNIQLSLSYGD
DCVVAVALGVRKWCLWPLASIIR

StcK                                                SEQ ID NO: 19
MTPSPFLDAVDAGLSRLYACFGGQGPSNWAGLDELVHLSHAYADCAPIQDLLDSSARRLESQQR
SHTDRHFLLGAGSNYRPGSTTLLHPHHLPEDLALSPYSFPINTLLSLLHYAITAYSLQLDPGQL
RQKLQGAIGHSQGVFVAAAIAISHTDHGWPSFYRAADLALQLSFWVGLESHHASPRSILCANEV

-continued

```
IDCLENGEGAPSHLLSVTGLDINHLERLVRKLNDQGGDSLYISLINGHNKFVLAGAPHALRGVC

IALRSVKASPELDQSRVPFPLRRSVVDVQFLPVSAPYHSSLLSSVELRVTDAIGGLRLRGNDLA

IPVYCQANGSLRNLQDYGTHDILLTLIQSVTVERVNWPALCWAMNDATHVLSFGPGAVGSLVQD

VLEGTGMNVVNLSGQSMASNLSLLNLSAFALPLGKDWGRKYRPRLRKAAEGSAHASIETKMTRL

LGTPHVMVAGMTPTTCSPELVAAIIQADYHVEFACGGYYNRATLETALRQLSRSIPPHRSITCN

VIYASPKALSWQTQVLRRLIMEEGLPIDGITVGAGIPSPEVVKEWIDMLAISHIWFKPGSVDAI

DRVLTIARQYPTLPVGIQWTGGRAGGHHSCEDFHLPILDCYARIRNCENVILVAGSGFGGAEDT

WPYMNGSWSCKLGYAPMPFDGILLGSRMMVAREAKTSFAVKQLIVEAPGVKDDGNDNGAWAKCE

HDAVGGVISVTSEMGQPIHVLATRAMRLWKEFDDRFFSIRDPKRLKAALKQHRVEIINRLNNDF

ARPWFAQTDSSKPTEIEELSYRQVLRRLCQLTYVQHQARWIDSSYLSLVHDFLRLAQGRLGSGS

EAELRFLSCNTPIELEASFDAAYGVQGDQILYPEDVSLLINLFRRQGQKPVPFIPRLDADFQTW

FKKDSLWQSEDVDAVVDQDAQRVCIIQGPVAVRHSRVCDEPVKDILDGITEAHLKMMLKEAASD

NGYTWANQRDEKGNRLPGIETSQEGSLCRYYLVGPTLPSTEAIVEHLVGECAWGYAALSQKKVV

FGQNRAPNPIRDAFKPDIGDVIEAKYMDGCLREITLYHSLRRQGDPRAIRAALGLIHLDGNKVS

VTLLTRSKGKRPALEFKMELLGGTMGPLILKMHRTDYLDSVRRLYTDLWIGRDLPSPTSVGLNS

EFTGDRVTITAEDVNTFLAIVGQAGPARCRAWGTRGPVVPIDYAVVIAWTALTKPILLEALDAD

PLRLLHQSASTRFVPGIRPLHVGDTVTTSSRITERTITTIGQRVEISAELLREGKPVVRLQTTF

IIQRRPEESVSQQQFRCVEEPDMVIRVDSHTKLRVLMSRKWFLLDGPCSDLIGKILIFQLHSQT

VFDAAGAPASLQVSGSVSLAPSDTSVVCVSSVGTRIGRVYMEEEGFGANPVMDFLNRHGAPRVQ

RQPLPRAGWTGDDAASISFTAPAQSEGYAMVSGDTNPIHVCPLFSRFAGLGQPVVHGLHLSATV

RRILEWIIGDNERTRFCSWAPSFDGLVRANDRLRMEIQHFAMADGCMVVHVRVLKESTGEQVMH

AEAVLEQAQTTYVFTGQGTQERGMGMALYDTNAAARAVWDRAERHFRSQYGISLLHIVRENPTS

LTVNFGSRRGRQIRDIYLSMSDSDPSMLPGLTRDSRSYTFNYPSGLLMSTQFAQPALAVMEIAE

YAHLQAQGVVQTQAIFAGHSLGEYSSLGACTTIMPFESLLSLILYRGLKMQNTLPRNANGRTDY

GMVAADPSRIRSDFTEDRLIELVRLVSQATGVLLEVVNYNVHSRQYVCAGHVRSLWVLSHACDD

LSRSTSPNSPQTMSECIAHHIPSSCSVTNETELSRGRATIPLAGVDIPFHSQMLRGHIDGYRQY

LRHHLRVSDIKPEELVGRWIPNVTGKPFALDAPYIRLVQGVTQSRPLLELLRRVEENR

FAS alpha | FAS2
                                                        SEQ ID NO: 20
MRPEIEQELAHTLLVELLAYQFASPVRWIETQDVILAEKRTERIVEIGPADTLGGMARRTLASK

YEAYDAATSVQRQILCYNKDAKEIYYDVDPVEEETESAPEAAAAPPTSAAPAAAVVAAPAPAAS

APSAGPAAPVEDAPVTALDIVRTLVAQKLKKALSDVPLNKAIKDLVGGKSTLQNEILGDLGKEF

GSTPEKPEDTPLDELGASMQATFNGQLGKQSSSLIARLVSSKMPGGFNITAVRKYLETRWGLGP

GRQDGVLLLALTMEPASRIGSEPDAKVFLDDVANKYAANSGISLNVPTASGDGGASAGGMLMDP

AAIDALTKDQRALFKQQLEIIARYLKMDLRDGQKAFVASQETQKTLQAQLDLWQAEHGDFYASG

IEPSFDPLKARVYDSSWNWARQDALSMYYDIIFGRLKVVDREIVSQCIRIMNRSNPLLLEFMQY

HIDNCPTERGETYQLAKELGEQLIENCKEVLGVSPVYKDVAVPTGPQTTIDARGNIEYQEVPRA

SARKLEHYVKQMAEGGPISEYSNRAKVQNDLRSVYKLIRRQHRLSKSSQLQFNALYKDVVRALS

MNENQIMPQENGSTKKPGRNGSVRNGSPRAGKVETIPFLHLKKKNEHGWDYSKKLTGIYLDVLE

SAARSGLTFQGKNVLMTGAGAGSIGAEVLQGLISGGAKVIVTTSRYSREVTEYYQAMYARYGAR

GSQLVVVPFNQGSKQDVEALVDYIYDTKKGLGWDLDFIVPFAAIPENGREIDSIDSKSELAHRI

MLTNLLRLLGSVKAQKQANGFETRPAQVILPLSPNHGTFGNDGLYSESKLALETLFNRWYSENW
```

-continued

SNYLTICGAVIGWTRGTGLMSGNNMVAEGVEKLGVRTFSQQEMAFNLLGLMAPAIVNLCQLDPV
WADLNGGLQFIPDLKDLMTRLRTEIMETSDVRRAVIKETAIENKVVNGEDSEVLYKKVIAEPRA
NIKFQFPNLPTWDEDIKPLNENLKGMVNLDKVVVVTGFSEVGPWGNSRTRWEMEASGKFSLEGC
VEMAWIMGLIRHHNGPIKGKTYSGWVDSKTGEPVDDKDVKAKYEKYILEHSGIRLIEPELFKGY
DPKKKQLLQEIVIEEDLEPFEASKETAEEFKREHGEKVEIFEVLESGEYTVRLKKGATLLIPKA
LQFDRLVAGQVPTGWDARRYGIPEDIIEQVDPVTLFVLVCTAEAMLSAGVTDPYEFYKYVHLSE
VGNCIGSGIGGTHALRGMYKDRYLDKPLQKDILQESFINTMSAWVNMLLLSSTGPIKTPVGACA
TAVESVDIGYETIVEGKARVCFVGGFDDFQEEGSYEFANMKATSNAEDEFAHGRTPQEMSRPTT
TTRAGFMESQGCGMQLIMSAQLALDMGVPIYGIIALTTTATDKIGRSVPAPGQGVLTTARENPG
KFPSPLLDIKYRRRQLELRKRQIREWQESELLYLQEEAEAIKAQNPADFVVEEYLQERAQHINR
EAIRQEKDAQFSLGNNFWKQDSRIAPLRGALATWGLTVDEIGVASFHGTSTVANDKNESDVICQ
QMKHLGRKKGNALLGIFQKYLTGHPKGAAGAWMFNGCLQVLDSGLVPGNRNADNVDKVMEKFDY
IVYPSRSIQTDGIKAFSVTSFGFGQKGAQVIGIHPKYLYATLDRAQFEAYRAKVETRQKKAYRY
FHNGLVNNSIFVAKNKAPYEDELQSKVFLNPDYRVAADKKTSELKYPPKPPVATDAGSESTKAV
IESLAKAHATENSKIGVDVESIDSINISNETFIERILPASEQQYCQNAPSPQSSFAGRWSAKEA
VFKSLGVCSKGAGAPLKDIEIENDSNGAPTLHGVAAEAAKEAGVKHISVSISHSDMQAVAVAIS
QF

FAS beta | FAS1
                                                          SEQ ID NO: 21
MYGTSTGPQTGINTPRSSQSLRPLILSHGSLEFSFLVPTSLHFHASQLKDTFTASLPEPTDELA
QDDEPSSVAELVARYIGHVAHEVEEGEDDAHGTNQDVLKLTLNEFERAFMRGNDVHAVAATLPG
ITAKKVLVVEAYYAGRAAAGRPTKPYDSALFRAASDEKARIYSVLGGQGNIEEYFDELREVYNT
YTSFVDDLISSSAELLQSLSREPDANKLYPKGLNVMQWLREPDTQPDVDYLVSAPVSLPLIGLV
QLAHFAVTCRVLGKEPGEILERFSGTTGHSQGIVTAAAIATATTWESFHKAVANALTMLFWIGL
RSQQAYPRTSIAPSVLQDSIENGEGTPTPMLSIRDLPRTAVQEHIDMTNQHLPEDRHISISLVN
SARNFVVTGPPLSLYGLNLRLRKVKAPTGLDQNRVPFTQRKVRFVNRFLPITAPFHSQYLYSAF
DRIMEDLEDVEISPKSLTIPVYGTKTGDDLRAISDANVVPALVRMITHDPVNWEQTTAFPNATH
IVDFGPGGISGLGVLTNRNKDGTGVRVILAGSMDGTNAEVGYKPELFDRDEHSVKYAIDWVKEY
GPRLVKNATGQTFVDTKMSRLLGIPPIMVAGMTPTTVPWDFVAATMNAGYHIELAGGGYYNAKT
MTEAITKIEKAIPPGRGITVNLIYVNPRAMGWQIPLIGKLRADGVPIEGLTIGAGVPSIEVANE
YIETLGIKHIAFKPGSVDAIQQVINIAKANPKFPVILQWTGGRGGGHHSFEDFHQPILQMYSRI
RRHENIILVAGSGFGGAEDTYPYLSGNWSSRFGYPPMPFDGCLFGSRMMTAKEAHTSKNAKQAI
VDAPGLDDQDWEKTYKGAAGGVVTVLSEMGEPIHKLATRGVLFWHEMDQKIFKLDKAKRVPELK
KQRDYIIKKLNDDFQKVWFGRNSAGETVDLEDMTYAEVVHRMVDLMYVKHEGRWIDDSLKKLTG
DFIRRVEERFTTAEGQASLLQNYSELNVPYPAVDNILAAYPEAATQLINAQDVQHFLLLCQRRG
QKPVPFVPSLDENFEYWFKKDSLWQSEDLEAVVGQDVGRTCILQGPMAAKFSTVIDEPVGDILN
SIHQGHIKSLIKDMYNGDETTIPITEYFGGRLSEAQEDIEMDGLTISEDANKISYRLSSSAADL
PEVNRWCRLLAGRSYSWRHALFSADVFVQGHRFQTNPLKRVLAPSTGMYVEIANPEDAPKTVIS
VREPYQSGKLVKTVDIKLNEKGPIALTLYEGRTAENGVVPLTFLFTYHPDTGYAPIREVMDSRN
DRIKEFYYRIWFGNKDVPFYTPTTATFNGGRETITSQAVADFVHAVGNTGEAFVERPGKEVFAP
MDFAIVAGWKAITKPIFPRTIDGDLLKLVHLSNGFKMVPGAQPLKVGDVLDTTAQINSIINEES -continued
GKIVEVCGTIRRDGKPIMHVTSQFLYRGAYTDFENTFQRKDEVPMQVHLASSRDVAILRSKEWF

RLDMDDVELLGQTLTFRLQSLIRFKNKNVFSQVQTMGQVLLELPTKEVIQVASVDYEAGTSHGN

PVIDYLQRNGTSIEQPVYFENPIPLSGKTPLVLRAPASNETYARVSGDYNPIHVSRVFSSYANL

PGTITHGMYTSAAVRSLVETWAAENNIGRVRGFHVSLVDMVLPNDLITVRLQHVGMIAGRKIIK

VEASNKETEDKVLLGEAEVEQPVTAYVFTGQGSQEQGMGMELYATSPVAKEVWDRPSFHWNYGL

SIIDIVKNNPKERTVHFGGPRGKAIRQNYMSMTFETVNADGTIKSEKIFKEIDETTTSYTYRSP

TGLLSATQFTQPALTLMEKASFEDMRSKGLVQRDSSFAGHSLGEYSALADLADVMLIESLVSVV

FYRGLTMQVAVERDEQGRSNYSMCAVNPSRISKTFNEQALQYVVGNISEQTGWLLEIVNYNVAN

MQYVAAGDLRALDCLTNLLNYLKAQNIDIPALMQSMSLEDVKAHLVNIIHECVKQTEAKPKPIN

LERGFATIPLKGIDVPFHSTFLRSGVKPFRSFLIKKINKTTIDPSKLVGKYIPNVTARPFEITK

EYFEDVYRLTNSPRIAHILANWEKYEEGTEGGSRHGGTTAASS

TABLE 4

HEXA HOMOLOGS

| Description | Ident | Accession |
|---|---|---|
| hypothetical protein [*Aspergillus parasiticus* SU-1] | 99% | KJK60794.1 |
| sterigmatocystin biosynthesis fatty acid synthase subunit alpha [*Aspergillus flavus* AF70] | 98% | KOC17633.1 |
| fatty acid synthase alpha subunit [*Aspergillus flavus* NRRL3357] | 98% | XP_002379948.1 |
| HexA [*Aspergillus flavus*] | 98% | AAS90024.1 |
| unnamed protein product [*Aspergillus oryzae* RIB40] | 98% | χP_001821514.3 |
| sterigmatocystin biosynthesis fatty acid synthase subunit alpha [*Aspergillus arachidicola*] | 97% | PIG79619.1 |
| sterigmatocystin biosynthesis fatty acid synthase subunit alpha [*Aspergillus bombycis*] | 92% | XP_022391210.1 |
| sterigmatocystin biosynthesis fatty acid synthase subunit alpha [*Aspergillus nomius* NRRL 13137] | 92% | XP_015404699.1 |

TABLE 5

HEXB HOMOLOGS

| Description | Ident | Accession |
|---|---|---|
| hypothetical protein [*Aspergillus parasiticus* SU-1] | 99% | KJK60796.1 |
| fatty acid synthase beta subunit [*Aspergillus flavus* NRRL3357] | 99% | XP_002379947.1 |
| HexB [*Aspergillus flavus*] | 99% | AAS90085.1 |
| unnamed protein product [*Aspergillus oryzae* RIB40] | 98% | XP_001821515.1 |
| fatty acid synthase beta subunit [*Aspergillus flavus* AF70] | 98% | KOC17632.1 |
| fatty acid synthase beta subunit [*Aspergillus arachidicola*] | 96% | PIG79622.1 |
| HexB [*Aspergillus flavus*] | 96% | AAS90002.1 |
| enoyl reductase domain of FAS1 [*Aspergillus oryzae* 3.042] | 98% | EIT81347.1 |
| fatty acid synthase beta subunit [*Aspergillus bombycis*] | 89% | XP_022391135.1 |
| HexB [*Aspergillus nomius*] | 90% | AAS90050.1 |
| fatty acid synthase beta subunit [*Aspergillus nomius* NRRL 13137] | 90% | XP_015404098.1 |

TABLE 6

FAS1 HOMOLOGS

| Description | Ident | Accession |
|---|---|---|
| fatty acid synthase, beta subunit [*Aspergillus nidulans*] | 100% | AAB41494.1 |
| hypothetical protein [*Aspergillus nidulans* FGSC A4] | 99% | XP_682677.1 |
| hypothetical protein [*Aspergillus sydowii* CBS 593.65] | 94% | OJJ52999.1 |

TABLE 6-continued

FAS1 HOMOLOGS

| Description | Ident | Accession |
|---|---|---|
| Putative Fatty acid synthase beta subunit dehydratase [*Aspergillus calidoustus*] | 94% | CEN62087.1 |
| hypothetical protein [*Aspergillus versicolor* CBS 583.65] | 93% | OJJ08968.1 |
| hypothetical protein [*Aspergillus rambellii*] | 91% | KKK18959.1 |
| hypothetical protein [*Aspergillus ochraceoroseus*] | 91% | KKK13726.1 |
| fatty acid synthase beta subunit dehydratase [*Aspergillus terreus* NIH2624] | 91% | XP_001213436.1 |
| hypothetical protein [*Aspergillus carbonarius* ITEM 5010] | 89% | OOF94457.1 |
| hypothetical protein [*Aspergillus turcosus*] | 90% | OXN14637.1 |
| fatty acid synthase beta subunit [*Aspergillus sclerotioniger* CBS 115572] | 89% | PWY96795.1 |
| fatty acid synthase beta subunit [*Aspergillus heteromorphus* CBS 117.55] | 89% | XP_025394299.1 |
| fatty acid synthase beta subunit [*Aspergillus sclerotiicarbonarius* CBS 121057] | 89% | PYI01270.1 |
| hypothetical protein [*Aspergillus thermomutatus*] | 90% | OXS11585.1 |

TABLE 7

FAS2 HOMOLOGS

| Description | Ident | Accession |
|---|---|---|
| RecName: Full = Fatty acid synthase subunit alpha; Includes: RecName: Full = Acyl carrier; Includes: RecName: Full = 3-oxoacyl-[acyl-carrier-protein] reductase; AltName: Full = Beta-ketoacyl reductase; Includes: RecName: Full = 3-oxoacyl-[acyl-carrier-protein] synthase; AltName: Full = Beta-ketoacyl synthase | 100% | P78615.1 |
| FAS2_PENPA Fatty acid synthase subunit alpha [*Aspergillus nidulans* FGSC A4] | 99% | XP_682676.1 |
| TPA: Fatty acid synthase, alpha subunit [Source: UniProtKB/TrEMBL; Acc: P78615] [*Aspergillus nidulans* FGSC A4] | 99% | CBF87553.1 |
| hypothetical protein ASPVEDRAFT_144895 [*Aspergillus versicolor* CBS 583.65] | 93% | OJJ08967.1 |
| Putative Fatty acid synthase subunit alpha reductase [*Aspergillus calidoustus*] | 93% | CEN62088.1 |
| hypothetical protein ASPSYDRAFT_564317 [*Aspergillus sydowii* CBS 593.65] | 93% | OJJ52998.1 |
| hypothetical protein BP01DRAFT_383520 [*Aspergillus saccharolyticus* JOP 1030-1] | 91% | XP_025430630.1 |
| putative fatty acid synthase alpha subunit FasA [*Aspergillus indologenus* CBS 114.80] | 91% | PYI32058.1 |
| hypothetical protein ASPCADRAFT_208136 [*Aspergillus carbonarius* ITEM 5010] | 90% | OOF94458.1 |
| hypothetical protein ASPACDRAFT_79663 [*Aspergillus aculeatus* ATCC 16872] | 90% | XP_020055233.1 |
| fatty acid synthase alpha subunit FasA [*Aspergillus kawachii* IFO 4308] | 91% | GAA92751.1 |
| putative fatty acid synthase alpha subunit FasA [*Aspergillus fijiensis* CBS 313.89] | 90% | RAK72625.1 |
| putative fatty acid synthase alpha subunit FasA [*Aspergillus aculeatinus* CBS 121060] | 90% | XP_025498650.1 |
| putative fatty acid synthase alpha subunit FasA [*Aspergillus violaceofuscus* CBS 115571] | 90% | PYI15679.1 |
| fatty acid synthase alpha subunit FasA [*Aspergillus piperis* CBS 112811] | 91% | XP_025520376.1 |
| fatty acid synthase alpha subunit FasA [*Aspergillus vadensis* CBS 113365] | 91% | PYH66515.1 |
| putative fatty acid synthase alpha subunit FasA [*Aspergillus brunneoviolaceus* CBS 621.78] | 90% | XP_025442388.1 |
| fatty acid synthase alpha subunit FasA [*Aspergillus neoniger* CBS 115656] | 91% | XP_025476115.1 |
| fatty acid synthase alpha subunit FasA [*Aspergillus costaricaensis* CBS 115574] | 91% | RAK83984.1 |

Fatty Acid and Fat Producing Genes

The production of fatty acids and fats in yeast may be increased by expressing rate limiting genes in the lipid biosynthesis pathway. *Y. lipolytica* naturally produces Acetyl-CoA. The overexpression of ACC1 increases the amount of Malonyl-CoA, which is the first step in fatty acid production. In certain embodiments, the one or more genetic modifications that result in increased production of fatty acids or fats comprise delta-9 stearoyl-CoA desaturase (SCD), Acetyl-CoA carboxylase (ACC1) and Diacylglyceride acyl-transferase (DGA1). The sequences for the native *Y. lipolytica* genes are shown herein, however the skilled person would understand that homologous genes may also be suitable. Examples of DGA1 homologs as shown in Table 8. In certain embodiments, SCD comprises a polynucleotide encoding a polypeptide that has at least 70%, 75%, 80%, 85%, 90%, 91%, 92%, 93%, 94%, 95%, 96%, 97%, 98%, 99% or 100% sequence identity to SEQ ID NO: 22. In certain embodiments, SCD comprises a polypeptide that has at least 70%, 75%, 80%, 85%, 90%, 91%, 92%, 93%, 94%, 95%, 96%, 97%, 98%, 99% or 100% sequence identity to SEQ ID NO: 22. In certain embodiments, ACC1 comprises a polynucleotide encoding a polypeptide that has at least 70%, 75%, 80%, 85%, 90%, 91%, 92%, 93%, 94%, 95%, 96%, 97%, 98%, 99% or 100% sequence identity to SEQ ID NO: 23. In certain embodiments, ACC1 comprises a polypeptide that has at least 70%, 75%, 80%, 85%, 90%, 91%, 92%, 93%, 94%, 95%, 96%, 97%, 98%, 99% or 100% sequence identity to SEQ ID NO: 23. In certain embodiments, DGA1 comprises a polynucleotide encoding a polypeptide that has at least 70%, 75%, 80%, 85%, 90%, 91%, 92%, 93%, 94%, 95%, 96%, 97%, 98%, 99% or 100% sequence identity to SEQ ID NO: 24. In certain embodiments, DGA1 comprises a polypeptide that has at least 70%, 75%, 80%, 85%, 90%, 91%, 92%, 93%, 94%, 95%, 96%, 97%, 98%, 99% or 100% sequence identity to SEQ ID NO: 24.

SCD, ACC1 and DGA1 may be overexpressed in yeast by adding extra copies of the genes driven by native or stronger promoters. Alternatively, native promoters may be substituted by stronger promoters such as TEFin, hp4d, hp8d and others, as would be appreciated by the person skilled in the art. The overexpression of SCD, ACC1 and DGA1 may be determined by quantitative PCR, Microarrays, or next generation sequencing technologies, such as RNA-seq. Alternatively, the product of increased enzyme levels will be increased production of fatty acids. Fatty acid production may be determined using chemical titration, thermometric titration, measurement of metal-fatty acid complexes using spectrophotometry, enzymatic methods or using a fatty acid binding protein.

Variants of the fatty acid and fat producing proteins, such as ACC1 retain the ability to produce malonyl-CoA from acetyl-CoA plus bicarbonate. For example, a variant of a fatty acid and fat producing protein, such as ACC1, must retain the ability to produce malonyl-CoA from acetyl-CoA plus bicarbonate with at least about 50%, at least about 60%, at least about 70%, at least about 80%, at least about 90%, or at least about 100% efficacy compared to the original sequence. In preferred embodiments, a variant of a fatty acid and fat producing protein, such as ACC1, has improved activity over the sequence from which it is derived in that the improved variant common cannabinoid protein has more than 110%, 120%, 130%, 140%, or and 150% improved activity in producing malonyl-CoA from acetyl-CoA plus bicarbonate, as compared to the sequence from which the improved variant is derived.

SCD

SEQ ID NO: 22

MVKNVDQVDLSQVDTIASGRDVNYKVKYTSGVKMSQGAYDDKGRHISE

QPFTWANWHQHINWLNFILVIALPLSSFAAAPFVSFNWKTAAFAVGYY

MCTGLGITAGYHRMWAHRAYKAALPVRIILALFGGGAVEGSIRWWASS

HRVHHRWTDSNKDPYDARKGFWFSHFGWMLLVPNPKNKGRTDISDLNN

DWVVRLQHKYYVYVLVFMAIVLPTLVCGFGWGDWKGGLVYAGIMRYTF

VQQVTFCVNSLAHWIGEQPFDDRRTPRDHALTALVTFGEGYHNFHHEF

PSDYRNALIWYQYDPTKWLIWTLKQVGLAWDLQTFSQNAIEQGLVQQR

QKKLDKWRNNLNWGIPIEQLPVIEFEEFQEQAKTRDLVLISGIVHDVS

AFVEHHPGGKALIMSAVGKDGTAVFNGGVYRHSNAGHNLLATMRVSVI

RGGMEVEVWKTAQNEKKDQNIVSDESGNRIHRAGLQATRVENPGMSGM

AA

ACC1

SEQ ID NO: 23

MRLQLRTLTRRFFSMASGSSTPDVAPLVDPNIHKGLASHFFGLNSVHT

AKPSKVKEFVASHGGHTVINKVLIANNGIAAVKEIRSVRKWAYETFGD

ERAISFTVMATPEDLAANADYIRMADQYVEVPGGTNNNNYANVELIVD

VAERFGVDAVWAGWGHASENPLLPESLAASPRKIVFIGPPGAAMRSLG

DKISSTIVAQHAKVPCIPWSGTGVDEVVVDKSTNLVSVSEEVYTKGCT

TGPKQGLEKAKQIGFPVMIKASEGGGGKGIRKVEREEDFEAAYHQVEG

EIPGSPIFIMQLAGNARHLEVQLLADQYGNNISLFGRDCSVQRRHQKI

IEEAPVTVAGQQTFTAMEKAAVRLGKLVGYVSAGTVEYLYSHEDDKFY

FLELNPRLQVEHPTTEMVTGVNLPAAQLQIAMGIPLDRIKDIRLFYGV

NPHTTTPIDFDFSGEDADKTQRRPVPRGHTTACRITSEDPGEGFKPSG

GTMHELNFRSSSNVWGYFSVGNQGGIHSFSDSQFGHIFAFGENRSASR

KHMVVALKELSIRGDFRTTVEYLIKLLETPDFEDNTITTGWLDELISN

KLTAERPDSFLAVVCGAATKAHRASEDSIATYMASLEKGQVPARDILK

TLFPVDFIYEGQRYKFTATRSSEDSYTLFINGSRCDIGVRPLSDGGIL

CLVGGRSHNVYWKEEVGATRLSVDSKTCLLEVENDPTQLRSPSPGKLV

KFLVENGDHVRANQPYAEIEVMKMYMTLTAQEDGIVQLMKQPGSTIEA

GDILGILALDDPSKVKHAKPFEGQLPELGPPTLSGNKPHQRYEHCQNV

LHNILLGFDNQVVMKSTLQEMVGLLRNPELPYLQWAHQVSSLHTRMSA

KLDATLAGLIDKAKQRGGEFPAKQLLRALEKEASSGEVDALFQQTLAP

LFDLAREYQDGLAIHELQVAAGLLQAYYDSEARFCGPNVRDEDVILKL

REENRDSLRKVVMAQLSHSRVGAKNNLVLALLDEYKVADQAGTDSPAS

NVHVAKYLRPVLRKIVELESRASAKVSLKAREILIQCALPSLKERTDQ

LEHILRSSVVESRYGEVGLEHRTPRADILKEVVDSKYIVFDVLAQFFA

HDDPWIVLAALELYIRRACKAYSILDINYHQDSDLPPVISWRFRLPTM

SSALYNSVVSSGSKTPTSPSVSRADSVSDFSYTVERDSAPARTGAIVA

VPHLDDLEDALTRVLENLPKRGAGLAISVGASNKSAAASARDAAAAAA

SSVDTGLSNICNVMIGRVDESDDDDTLIARISQVIEDFKEDFEACSLR

RITFSFGNSRGTYPKYFTFRGPAYEEDPTIRHIEPALAFQLELARLSN

FDIKPVHTDNRNIHVYEATGKNAASDKRFFTRGIVRPGRLRENIPTSE

YLISEADRLMSDILDALEVIGTTNSDLNHIFINFSAVFALKPEEVEAA

FGGFLERFGRRLWRLRVTGAEIRMMVSDPETGSAFPLRAMINNVSGYV

VQSELYAEAKNDKGQWIFKSLGKPGSMHMRSINTPYPTKEWLQPKRYK

AHLMGTTYCYDFPELFRQSIESDWKKYDGKAPDDLMTCNELILDEDSG

ELQEVNREPGANNVGMVAWKFEAKTPEYPRGRSFIVVANDITFQIGSF

GPAEDQFFFKVTELARKLGIPRIYLSANSGARIGIADELVGKYKVAWN

-continued

DETDPSKGFKYLYFTPESLATLKPDTVVTTEIEEEGPNGVEKRHVIDY

IVGEKDGLGVECLRGSGLIAGATSRAYKDIFTLTLVTCRSVGIGAYLV

RLGQRAIQIEGQPIILTGAPAINKLLGREVYSSNLQLGGTQIMYNNGV

SHLTARDDLNGVHKIMQWLSYIPASRGLPVPVLPHKTDVWDRDVTFQP

VRGEQYDVRWLISGRTLEDGAFESGLFDKDSFQETLSGWAKGVVVGRA

RLGGIPFGVIGVETATVDNTTPADPANPDSIEMSTSEAGQVWYPNSAF

KTSQAINDFNHGEALPLMILANWRGFSGGQRDMYNEVLKYGSFIVDAL

VDYKQPIMVYIPPTGELRGGSWVVVDPTINSDMMEMYADVESRGGVLE

PEGMVGIKYRRDKLLDTMARLDPEYSSLKKQLEESPDSEELKVKLSVR

EKSLMPIYQQISVQFADLHDRAGRMEAKGVIREALVWKDARRFFFWRI

RRRLVEEYLITKINSILPSCTRLECLARIKSWKPATLDQGSDRGVAEW

FDENSDAVSARLSELKKDASAQSFASQLRKDRQGTLQGMKQALASLSE

AERAELLKGL

DGA1
SEQ ID NO: 24
MTIDSQYYKSRDKNDTAPKIAGIRYAPLSTPLLNRCETFSLVWHIFSI

PTFLTIFMLCCAIPLLWPFVIAYVVYAVKDDSPSNGGVVKRYSPISRN

FFIWKLFGRYFPITLHKTVDLEPTHTYYPLDVQEYHLIAERYWPQNKY

LRAIISTIEYFLPAFMKRSLSINEQEQPAERDPLLSPVSPSSPGSQPD

KWINHDSRYSRGESSGSNGHASGSELNGNGNNGTTNRRPLSSASAGST

ASDSTLLNGSLNSYANQIIGENDPQLSPTKLKPTGRKYIFGYHPHGII

GMGAFGGIATEGAGWSKLFPGIPVSLMTLTNNFRVPLYREYLMSLGVA

SVSKKSCKALLKRNQSICIVVGGAQESLLARPGVMDLVLLKRKGFVRL

GMEVGNVALVPIMAFGENDLYDQVSNDKSSKLYRFQQFVKNFLGFTLP

LMHARGVFNYDVGLVPYRRPVNIVVGSPIDLPYLPHPTDEEVSEYHDR

YIAELQRIYNEHKDEYFIDWTEEGKGAPEFRMIE

Specifically, examples of the culture conditions for producing at least one cannabinoid or cannabinoid precursor include a batch process and a fed batch or repeated fed batch process in a continuous manner, but are not limited thereto. Carbon sources that may be used for producing at least one cannabinoid or cannabinoid precursor may include sugars and carbohydrates such as glucose, sucrose, lactose, fructose, maltose, starch, xylose and cellulose; oils and fats such as soybean oil, sunflower oil, castor oil, coconut oil, chicken fat and beef tallow; fatty acids such as palmitic acid, stearic acid, oleic acid and linoleic acid; alcohols such as glycerol and ethanol; and organic acids such as gluconic acid, acetic acid, malic acid and pyruvic acid, but these are not limited thereto. These substances may be used alone or in a mixture. Nitrogen sources that may be used in the present disclosure may include peptone, yeast extract, meat extract, malt extract, corn steep liquor, defatted soybean cake, and urea or inorganic compounds, such as ammonium sulfate, ammonium chloride, ammonium phosphate, ammonium carbonate, and ammonium nitrate, but these are not limited thereto. These nitrogen sources may also be used alone or in a mixture. Phosphorus sources that may be used in the present disclosure may include potassium dihydrogen phosphate or dipotassium hydrogen phosphate, or corresponding sodium-containing salts, but these are not limited thereto. In addition, the culture medium may contain a metal salt such as magnesium sulfate or iron sulfate, which is may be required for the growth. Lastly, in addition to the above-described substances, essential growth factors such as amino acids and vitamins may be used. Such a variety of culture methods is disclosed, for example, in the literature ("Biochemical Engineering" by James M. Lee, Prentice-Hall International Editions, pp 138-176).

Basic compounds such as sodium hydroxide, potassium hydroxide, or ammonia, or acidic compounds such as phosphoric acid or sulfuric acid may be added to the culture medium in a suitable manner to adjust the pH of the culture medium. In addition, an anti-foaming agent such as fatty acid polyglycol ester may be used to suppress the formation of bubbles. In certain embodiments, the culture medium is maintained in an aerobic state, accordingly, oxygen or oxygen-containing gas (e.g., air) may be injected into the

TABLE 8

DGA1 HOMOLOGS

| Description | Ident | Accession |
|---|---|---|
| YALI0E32769p [*Yarrowia lipolytica* CLIB122] | 100% | XP_504700.1 |
| Diacylglycerol acyltransferase [*Galactomyces candidus*] | 44% | CDO57007.1 |
| hypothetical protein [*Lipomyces starkeyi* NRRL Y-11557] | 60% | ODQ70106.1 |
| DAGAT-domain-containing protein [*Nadsonia fulvescens* var. *elongata* DSM 6958] | 60% | ODQ67305.1 |
| hypothetical protein [*Tortispora caseinolytica* NRRL Y-17796] | 65% | ODV90514.1 |
| diacylglycerol acyltransferase [*Saitoella complicata* NRRL Y-17804] | 60% | XP_019022950.1 |
| uncharacterized protein KUCA_T00002736001 [*Kuraishia capsulata* CBS 1993] | 51% | XP_022458761.1 |
| diacylglycerol O-acyltransferas-like protein 2B [*Meliniomyces bicolor* E] | 55% | XP_024728739.1 |
| Diacylglycerol O-acyltransferase 1 [*Hanseniaspora osmophila*] | 57% | OEJ83128.1 |
| DAGAT-domain-containing protein [*Ascoidea rubescens* DSM 1968] | 49% | XP_020048004.1 |

In a second aspect of the present disclosure, there is provided method of producing at least one cannabinoid or cannabinoid precursor comprising contacting the yeast of the disclosure with a carbohydrate source under culture conditions and for a time sufficient to produce the at least one cannabinoid or cannabinoid precursor.

culture medium. The temperature of the culture medium may be usually 20° C. to 35° C., preferably 25° C. to 32° C., but may be changed depending on conditions. The culture may be continued until the maximum amount of a desired cannabinoid precursor or cannabinoid is produced, and it may generally be achieved within 5 hours to 160 hours. The cannabinoid precursor or cannabinoid may be released into the culture medium or contained in the yeast cells.

The method of the present disclosure for producing at least one cannabinoid or cannabinoid precursor may include a step of recovering the at least one cannabinoid or cannabinoid precursor from the microorganism or the medium. Methods known in the art, such as centrifugation, filtration, anion-exchange chromatography, crystallization, HPLC, etc., may be used for the method for recovering at least one cannabinoid or cannabinoid precursor from the microorganism or the culture, but the method is not limited thereto. The step of recovering may include a purification process. Specifically, following an overnight culture, 1 L cultures are pelleted by centrifugation, resuspended, washed in PBS and pelleted. The cells are lysed by either chemical or mechanical methods or a combination of methods. Mechanical methods can include a French Press or glass bead milling or other standard methods. Chemical methods can include enzymatic cell lysis, solvent cell lysis, or detergent based cell lysis. A liquid-liquid extraction of the cannabinoids is performed using the appropriate chemical solvent in which the cannabinoids are highly soluble and the solvent is not miscible in water. Examples include hexane, ethyl acetate, and cyclohexane, preferably solvents with straight or branched alkane chains (C5-C8) or mixtures thereof.

In certain embodiments, the at least one cannabinoid or cannabinoid precursor comprises CBGA, THCA, CBDA or CBCA. The production of one or more cannabinoid precursors or cannabinoids may be determined using a variety of methods as described herein. An example protocol for analysing CBDA is as follows:
1. Remove solvent from samples under vacuum.
2. Re-suspend dry samples in either 100 uL of dry hexane or dry ethyl acetate
3. Add 20 uL of N-Methyl-N-(trimethylsilyl)trifluoroacetamide (MSTFA)
4. Briefly mix
5. Heat solution to 60° C. for 10-15 minutes
6. GC-MS Method
    a. Instrument Agilent 6890-5975 GC-MS (Model Number: Agilent 19091S-433)
    b. Column HP-5MS 5% Phenyl Methyl Siloxane
    c. OVEN:
        i. Initial temp: too ° C. (On) Maximum temp: 300° C.
        ii. Initial time: 3.00 min Equilibration time: 0.50 min
        iii. Ramps:
            # Rate Final temp Final time
            1—30.00 280 1.00
            2—70.00 300 5.00
            3—0.0 (Off)
        iv. Post temp: 0° C.
        v. Post time: 0.00 min
        vi. Run time: 15.29 min In a third aspect of the present disclosure, there is provided a cannabinoid precursor, cannabinoid or a combination thereof produced using the method of the second aspect. In certain embodiments, the at least one cannabinoid or cannabinoid precursor comprises CBGA, THCA, CBDA or CBCA.

EXAMPLES

Example 1: Vector Construction and Transformation

*Y. lipolytica* episomal plasmids comprise a centromere, origin and bacteria replicative backbone. Fragments for these regions were synthesized by Twist Bioscience and cloned to make an episomal parent vector pBM-pa. Plasmids were constructed by Gibson Assembly, Golden gate assembly, ligation or sequence- and ligation-independent cloning (SLIC). Genomic DNA isolation from bacteria (*E. coli*) and yeast (*Yarrowia lipolytica*) were performed using Wizard Genomic DNA purification kit according to manufacturer's protocol (Promega, USA). Synthetic genes were codon-optimized using GeneGenie or Genscript (USA) and assembled from gene fragments purchased from TwistBioscience. All the engineered *Y. lipolytica* strains were constructed by transforming the corresponding plasmids. All gene expression cassettes were constructed using a TEF intron promoter and synthesized short terminator. Up to six expression cassettes were cloned into episomal expression vectors through SLIC.

*E. coli* minipreps were performed using the Zyppy Plasmid Miniprep Kit (Zymo Research Corporation). Transformation of *E. coli* strains was performed using Mix & Go Competent Cells (Zymo research, USA). Transformation of *Y. lipolytica* with episomal expression plasmids was performed using the Zymogen Frozen EZ Yeast Transformation Kit II (Zymo Research Corporation), and spread on selective plates. Transformation of *Y. lipolytica* with linearized cassettes was performed using LiOAc method. Briefly, *Y. lipolytica* strains were inoculated from glycerol stocks directly into 10 ml YPD media, grown overnight and harvested at an OD600 between 9 and 15 by centrifugation at 1,000 g for 3 min. Cells were washed twice in sterile water. Cells were dispensed into separate microcentrifuge tubes for each transformation, spun down and resuspended in 1.0 ml 100 mM LiOAc. Cells were incubated with shaking at 30° C. for 60 min, spun down, resuspended in 90 µl 100 mM LiOAc and placed on ice. Linearized DNA (1-5 mg) was added to each transformation mixture in a total volume of 10 ul, followed by 25 ul of 50 mg/ml boiled salmon sperm DNA. Cells were incubated at 30° C. for 15 min with shaking, before adding 720 µl PEG buffer (50% PEG8000, 100 mM LiOAc, pH=6.0) and 45 µl 2 M Dithiothreitol. Cells were incubated at 30° C. with shaking for 60 min, heat-shocked for 10 min in a 39° C. water bath, spun down and resuspended in 1 ml sterile water. Cells (200 µl) were plated on appropriate selection plates.

Example 2: Yeast Culture Conditions

*E. coli* strain DH10B was used for cloning and plasmid propagation. DH10B was grown at 37° C. with constant shaking in Luria-Bertani Broth supplemented with 100 mg/L of ampicillin for plasmid propagation. *Y. lipolytica* strains W29 was used as the base strain for all experiments. *Y. lipolytica* was cultivated at 30° C. with constant agitation. Cultures (2 ml) of *Y. lipolytica* used in large-scale screens were grown in a shaking incubator at speed 250 rpm for 1 to 3 days, and larger culture volumes were shaken in 50 ml flasks or fermented in a bioreactor.

For colony screening and cell propagation, *Y. lipolytica* grew on YPD liquid media contained 10 g/L yeast extract, 20 g/L peptone and 20 g/L glucose, or YPD agar plate with addition of 20 g/L of agar. Medium was often supplemented with 150 to 300 mg/L Hygromycin B or 250 to 500 mg/L nourseothricin for selection, as appropriate. For cannabinoid producing strains, modified YPD media with 0.1 to 1 g/L yeast extract was used for promoting lipid accumulation and often supplemented with 0.2 g/L and 5 g/L ammonium sulphate as alternative nitrogen source.

Example 3: Cannabinoid Isolation

*Y. lipolytica* culture from the shaking flask experiment or bioreactor are pelleted and homogenized in acetonitrile followed by incubation on ice for 15 min. Supernatants are filtered (0.45 µm, Nylon) after centrifugation (13,100 g, 4° C., 20 min) and analyzed by HPLC-DAD. Quantification of products are based on integrated peak areas of the UV-chromatograms at 225 nm. Standard curves are generated for CBGA and THCA. The identity of all compounds can be confirmed by comparing mass and tandem mass spectra of each sample with coeluting standards analysed by Bruker Compact™ ESI-Q-TOF using positive ionization mode.

Example 4: Gene Combinations

Embodiment 1: *Y. lipolytica* ERG20 comprising F88W and N119W substitutions; tHMGR; OLS: OAC; CBGAS; THCAS; HexA and HexB.

Embodiment 2: *Y. lipolytica* ERG20 comprising F88W and N119W substitutions; HMGR; OLS: OAC; NphB Q161A; THCAS; FAS1 I306A, M1251W and FAS2 G1250S.

Embodiment 3: *S. cerevisiae* ERG20 comprising a K197E substitution; OLS: OAC; NphB Q161A; CBDAS; StcJ and StcK.

Embodiment 4: *Y. lipolytica* ERG20 comprising a K189E substitution; HMGR; OLS: OAC; CBGAS; CBCAS; HexA and HexB.

Embodiment 5: *Y. lipolytica* ERG20 comprising a K189E substitution; tHMGR; OLS: OAC; CBGAS; CBDAS; StcJ and StcK.

The genetically modified yeast of the present disclosure enable the production of cannabinoid precursors and cannabinoids. The accumulation of fatty acids or fats in the yeast of at least 5% dry weight provides a storage location for the cannabinoid precursors and cannabinoids removed from the plasma membrane. This reduces the accumulation of cannabinoid precursors and cannabinoids in the plasma membrane, reducing membrane destabilisation and reducing the chances of cell death. Oily yeast such as *Y. lipolytica* can be engineered to have a fatty acid or fat (e.g. lipid) content above 80% dry weight, compared to 2-3% for yeast such as *S. cerevisiae*. Accordingly, cannabinoid precursor and cannabinoid production can be much higher in oily yeast, particularly oily yeast engineered to have a high fatty acid or fat (eg lipid) content.

Throughout the specification and the claims that follow, unless the context requires otherwise, the words "comprise" and "include" and variations such as "comprising" and "including" will be understood to imply the inclusion of a stated integer or group of integers, but not the exclusion of any other integer or group of integers.

The reference to any prior art in this specification is not, and should not be taken as, an acknowledgement of any form of suggestion that such prior art forms part of the common general knowledge.

It will be appreciated by those skilled in the art that the disclosure is not restricted in its use to the particular application described. Neither is the present disclosure restricted in its preferred embodiment with regard to the particular elements and/or features described or depicted herein. It will be appreciated that the disclosure is not limited to the embodiment or embodiments disclosed, but is capable of numerous rearrangements, modifications and substitutions without departing from the scope of the disclosure as set forth and defined by the following claims.

REFERENCES

Angela, C., Hansen, E. H., Kayser, O., Carlsen, S. and Stehle, F. 2017. Microorganism design for heterologous biosynthesis of cannabinoids. *FEMS Yeast Research*.

Bonitz, T., Alva, V., Saleh, O., Lupas, A. N. and Heide, L., 2011. Evolutionary relationships of microbial aromatic prenyltransferases. *PloS one*, 6(11), p.e27336.

Brown, D. W., Adams, T. H. and Keller, N. P., 1996. *Aspergillus* has distinct fatty acid synthases for primary and secondary metabolism. *Proceedings of the National Academy of Sciences*, 93(25), pp. 14873-14877.

Curran, K. A., Morse, N.J., Markham, K. A., Wagman, A. M., Gupta, A. and Alper, H. S., 2015. Short synthetic terminators for improved heterologous gene expression in yeast. *ACS synthetic biology*, 4(7), pp. 824-832.

Gao, S., Tong, Y., Zhu, L., Ge, M., Zhang, Y., Chen, D., Jiang, Y. and Yang, S., 2017. Iterative integration of multiple-copy pathway genes in *Yarrowia lipolytica* for heterologous β-carotene production. *Metabolic engineering*, 41, pp. 192-201.

Gajewski, J., Pavlovic, R., Fischer, M., Boles, E. and Grininger, M., 2017. Engineering fungal de novo fatty acid synthesis for short chain fatty acid production. *Nature Communications*, 8, p. 14650.

Ghorai, N., Chakraborty, S., Gucchait, S., Saha, S. K. and Biswas, S., 2012. Estimation of total Terpenoids concentration in plant tissues using a monoterpene, Linalool as standard reagent. *Protocol Exchange*, 5.

Hitchman, T. S., Schmidt, E. W., Trail, F., Rarick, M. D., Linz, J. E. and Townsend, C. A., 2001. Hexanoate synthase, a specialized type I fatty acid synthase in aflatoxin B1 biosynthesis. *Bioorganic chemistry*, 29(5), pp. 293-307.

Kampranis, S. C. and Makris, A. M. 2012. Developing a yeast cell factory for the production of terpenoids. *Computational and structural biotechnology journal* 3, p. e201210006.

Kuzuyama, T., Noel, J. P. and Richard, S. B., 2005. Structural basis for the promiscuous biosynthetic prenylation of aromatic natural products. *Nature*, 435(7044), p. 983.

Lange, K., Schmid, A. and Julsing, M. K. 2016. Δ9-Tetrahydrocannabinolic acid synthase: The application of a plant secondary metabolite enzyme in biocatalytic chemical synthesis. *Journal of Biotechnology* 233, pp. 42-48.

MacPherson, M. and Saka, Y., 2016. Short synthetic terminators for assembly of transcription units in vitro and stable chromosomal integration in yeast *S. cerevisiae*. *ACS synthetic biology*, 6(1), pp. 130-138.

Muntendam, R. (2015). Metabolomics and bioanalysis of terpenoid derived secondary metabolites: Analysis of *Cannabis sativa* L. metabolite production and prenylases for cannabinoid production [Groningen].

Poulos, J. L. and Farnia, A. 2016. Patent US20160010126— Production of cannabinoids in yeast.

Qiao, K., Imam Abidi, S. H., Liu, H., Zhang, H., Chakraborty, S., Watson, N., Kumaran Ajikumar, P. and Stephanopoulos, G. 2015. Engineering lipid overproduction in the oleaginous yeast *Yarrowia lipolytica*. *Metabolic Engineering* 29, pp. 56-65.

Zhao, J., Bao, X., Li, C., Shen, Y. and Hou, J. 2016. Improving monoterpene geraniol production through geranyl diphosphate synthesis regulation in *Saccharomyces cerevisiae*. *Applied Microbiology and Biotechnology* 100(10), pp. 4561-4571.

Zhuang, X. U. N. Engineering Novel Terpene Production Platforms In The Yeast *Saccharomyces Cerevisiae*.

Zirpel, B., Degenhardt, F., Martin, C., Kayser, O. and Stehle, F. 2017. Engineering yeasts as platform organisms for cannabinoid biosynthesis. *Journal of Biotechnology*.

Zirpel, B., Stehle, F. and Kayser, O. 2015. Production of Δ9-tetrahydrocannabinolic acid from cannabigerolic acid by whole cells of *Pichia* (Komagataella) *pastoris* expressing Δ9-tetrahydrocannabinolic acid synthase from *Cannabis sativa* L. *Biotechnology Letters* 37(9), PP. 1869-1875.

---

The invention claimed is:

1. A genetically modified yeast comprising:
  (a) a first polynucleotide encoding a first polypeptide having at least 70% amino acid sequence identity to SEQ ID NO:23, wherein said first polypeptide has Acetyl-CoA Carboxylase 1 (ACC1) activity;
  (b) a second polynucleotide encoding a second polypeptide having at least 70% amino acid sequence identity to SEQ ID NO:4, wherein said second polypeptide has farnesyl diphosphate synthase activity;
  (c) a third polynucleotide encoding a third polypeptide having at least 70% amino acid sequence identity to SEQ ID NO:6, wherein said third polypeptide has hydroxymethylglutaryl-CoA reductase (HMGR) activity;
  (d) a fourth polynucleotide encoding a fourth polypeptide having at least 70% amino acid sequence identity to SEQ ID NO:7, wherein said fourth polypeptide has olivetol synthase (OLS) activity;
  (e) a fifth polynucleotide encoding a fifth polypeptide having at least 70% amino acid sequence identity to SEQ ID NO:8, wherein said fifth polypeptide has olivetolic acid cyclase (OAC) activity;
  (f) a sixth polynucleotide encoding a sixth polypeptide having at least 70% amino acid sequence identity to SEQ ID NO:11, wherein said sixth' polypeptide has CBGA synthase activity;
  (g) a seventh polynucleotide encoding a seventh polypeptide having at least 70% amino acid sequence identity to SEQ ID NO:16, wherein said seventh polypeptide has hexanoyl-CoA synthase (Hex) A activity, and an eighth polynucleotide encoding a eighth polypeptide having at least 70% amino acid sequence identity to SEQ ID NO:17, wherein said eighth polypeptide has HexB activity; and
  (h) a ninth polynucleotide encoding a ninth polypeptide having at least 70% amino acid sequence identity SEQ ID NO: 24, wherein said ninth polypeptide has diacylglyceride acyl-transferase (DGA) activity.

2. The genetically modified yeast of claim 1, wherein said yeast comprises at least 5% dry weight of fatty acids or fats.

3. The genetically modified yeast of claim 1, wherein said first polypeptide comprises SEQ ID NO:23.

4. The genetically modified yeast of claim 1, wherein said second polypeptide comprises a K189E substitution, a F88W substitution, and/or a N119W substitution.

5. The genetically modified yeast of claim 4, wherein said second polypeptide comprises SEQ ID NO:4.

6. The genetically modified yeast of claim 1, wherein said third polypeptide comprises SEQ ID NO:6.

7. The genetically modified yeast of claim 1, wherein said fourth polypeptide comprises SEQ ID NO:7.

8. The genetically modified yeast of claim 1, wherein said fifth polypeptide comprises SEQ ID NO:8.

9. The genetically modified yeast of claim 1, wherein said sixth polypeptide comprises SEQ ID NO:11.

10. The genetically modified yeast of claim 1, wherein said seventh polypeptide comprises SEQ ID NO:16.

11. The genetically modified yeast of claim 1, wherein said eighth polypeptide comprises SEQ ID NO:17.

12. A genetically modified yeast comprising:
  (a) a first polynucleotide encoding a first polypeptide having the amino acid sequence of SEQ ID NO:23;
  (b) a second polynucleotide encoding a second polypeptide having the amino acid sequence of SEQ ID NO:4;
  (c) a third polynucleotide encoding a third polypeptide having the amino acid sequence of SEQ ID NO:6;
  (d) a fourth polynucleotide encoding a fourth polypeptide having the amino acid sequence of SEQ ID NO:7;
  (e) a fifth polynucleotide encoding a fifth polypeptide having the amino acid sequence of SEQ ID NO:8;
  (f) a sixth polynucleotide encoding a sixth polypeptide having the amino acid sequence of SEQ ID NO:11;
  (g) a seventh polynucleotide encoding a seventh polypeptide having the amino acid sequence of SEQ ID NO:16 and an eighth polynucleotide encoding a eighth polypeptide having the amino acid sequence of SEQ ID NO:17; and
  (h) a ninth polynucleotide encoding a ninth polypeptide having the amino acid sequence of SEQ ID NO: 24.

13. The genetically modified yeast of claim 1, wherein the yeast is genetically modified to produce at least 5%, at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, or at least 25% dry weight of fatty acids or fats.

14. The genetically modified yeast of claim 1, wherein the yeast is oleaginous.

15. The genetically modified yeast of claim 14, wherein the yeast is selected from the genera Rhodosporidium, Rhodotorula, Yarrowia, Cryptococcus, Candida, Lipomyces and Trichosporon.

16. The genetically modified yeast of claim 1, wherein the yeast is a Yarrowia lipolytica, a Lipomyces starkey, a Rhodosporidium toruloides, a Rhodotorula glutinis, a Trichosporon fermentans or a Cryptococcus curvatus.

17. A method of producing at least one cannabinoid or cannabinoid precursor comprising contacting the yeast of claim 1 with a carbohydrate source under culture conditions and for a time sufficient to produce the at least one cannabinoid or cannabinoid precursor.

18. The method of claim 17, wherein the at least one cannabinoid or cannabinoid precursor comprises CBGA, THCA, CBDA or CBCA.

* * * * *